US009976138B2

(12) United States Patent
Prakash et al.

(10) Patent No.: US 9,976,138 B2
(45) Date of Patent: May 22, 2018

(54) METHODS AND COMPOUNDS USEFUL IN CONDITIONS RELATED TO REPEAT EXPANSION

(75) Inventors: Thazha P. Prakash, Carlsbad, CA (US); Eric E. Swayze, Encinitas, CA (US); David Corey, Dallas, TX (US); Dongbo Yu, Dallas, TX (US)

(73) Assignee: Ionis Pharmaceuticals, Inc., Carlsbad, CA (US)

( * ) Notice: Subject to any disclaimer, the term of this patent is extended or adjusted under 35 U.S.C. 154(b) by 596 days.

(21) Appl. No.: 14/342,176

(22) PCT Filed: Aug. 29, 2012

(86) PCT No.: PCT/US2012/052874
§ 371 (c)(1),
(2), (4) Date: Jun. 17, 2014

(87) PCT Pub. No.: WO2013/033223
PCT Pub. Date: Mar. 7, 2013

(65) Prior Publication Data
US 2014/0316121 A1    Oct. 23, 2014

Related U.S. Application Data

(60) Provisional application No. 61/528,719, filed on Aug. 29, 2011.

(51) Int. Cl.
*C07H 21/04* (2006.01)
*C12N 15/113* (2010.01)
*A61K 31/7088* (2006.01)

(52) U.S. Cl.
CPC ........ *C12N 15/113* (2013.01); *A61K 31/7088* (2013.01); *C12N 2310/113* (2013.01); *C12N 2310/315* (2013.01); *C12N 2310/321* (2013.01); *C12N 2310/322* (2013.01); *C12N 2310/323* (2013.01); *C12N 2310/3341* (2013.01); *C12N 2310/341* (2013.01); *C12N 2310/343* (2013.01); *C12N 2310/344* (2013.01); *C12N 2310/351* (2013.01); *C12N 2310/3521* (2013.01); *C12N 2310/3533* (2013.01); *C12N 2310/533* (2013.01); *C12N 2320/34* (2013.01)

(58) Field of Classification Search
CPC ..................................................... C12N 15/113
USPC ................................ 536/23.1, 24.5
See application file for complete search history.

(56) References Cited

U.S. PATENT DOCUMENTS

| | | |
|---|---|---|
| 3,687,808 A | 8/1972 | Merigan et al. |
| 4,845,205 A | 7/1989 | Huynh Dinh et al. |
| 5,130,302 A | 7/1992 | Spielvogel et al. |
| 5,134,066 A | 7/1992 | Rogers et al. |
| 5,175,273 A | 12/1992 | Bischofberger et al. |
| 5,367,066 A | 11/1994 | Urdea et al. |
| 5,432,272 A | 7/1995 | Benner |
| 5,457,187 A | 10/1995 | Gmelner et al. |
| 5,459,255 A | 10/1995 | Cook et al. |
| 5,484,908 A | 1/1996 | Froehler et al. |
| 5,502,177 A | 3/1996 | Matteucci et al. |
| 5,525,711 A | 6/1996 | Hawkins et al. |
| 5,552,540 A | 9/1996 | Haralambidis |
| 5,587,469 A | 12/1996 | Cook et al. |
| 5,594,121 A | 1/1997 | Froehler et al. |
| 5,596,091 A | 1/1997 | Switzer |
| 5,614,617 A | 3/1997 | Cook et al. |
| 5,645,985 A | 7/1997 | Froehler et al. |
| 5,681,941 A | 10/1997 | Cook et al. |
| 5,750,692 A | 5/1998 | Cook et al. |
| 5,763,588 A | 6/1998 | Matteucci et al. |
| 5,830,653 A | 11/1998 | Froehler et al. |
| 6,005,096 A | 12/1999 | Matteucci et al. |
| 6,268,490 B1 | 7/2001 | Imanishi et al. |
| 6,525,191 B1 | 2/2003 | Ramasamy |
| 6,670,461 B1 | 12/2003 | Wengel et al. |
| 6,770,748 B2 | 8/2004 | Imanishi et al. |
| 6,794,499 B2 | 9/2004 | Wengel et al. |
| 7,034,133 B2 | 4/2006 | Wengel et al. |
| 7,053,207 B2 | 5/2006 | Wengel |
| 7,399,845 B2 | 7/2008 | Seth et al. |
| 7,427,672 B2 | 9/2008 | Imanishi et al. |
| 7,741,457 B2 | 6/2010 | Swayze et al. |
| 8,501,805 B2 | 8/2013 | Seth et al. |
| 8,530,640 B2 | 9/2013 | Seth et al. |
| 8,546,556 B2 | 10/2013 | Seth et al. |
| 8,993,738 B2 * | 3/2015 | Prakash ............... C07H 19/067 435/455 |
| 2004/0171570 A1 | 9/2004 | Allerson et al. |

(Continued)

FOREIGN PATENT DOCUMENTS

| WO | WO 1999/014226 | 3/1999 |
|---|---|---|
| WO | WO 2004/106356 | 12/2004 |

(Continued)

OTHER PUBLICATIONS

Albaek et al., "Analogues of a Locked Nucleic Acid with Three-Carbon 2',4'-Linkages: Synthesis by Ring-Closing Metathesis and Influence of Nucleic Acid Duplex Stability" J. Org. Chem. (2006) 71:7731-7740.
Braasch et al., "Locked nucleic acid (LNA): fine-tuning the recognition of DNA and RNA" Chem. Biol. (2001) 8:1-7.
Brook et al., "Molecular basis of myotonic dystrophy: Expansion of a trinucleotide (CTG) repeat at the 3' end of a transcript encoding a protein kinase family member" Cell (1992) 68(4):799-808.
Cooper et al., "RNA and disease." Cell (2009) 136(4): 777-793.
Crooke et al., "Basic Principles of Antisense Therapeutics" Antisense Research and Application (1998) Chapter 1:1-50.
Crooke et al., "Pharmacokinetic Properties of Several Novel Oligonucleotide Analogs in mice" J. Pharmacol. Exp. Ther. (1996) 277: 923-937.

(Continued)

*Primary Examiner* — Jezia Riley
(74) *Attorney, Agent, or Firm* — Parker Highlander PLLC

(57) ABSTRACT

Described are compounds and methods useful for the treatment and investigation of diseases and disorders associated with expanded repeat-containing RNA molecules.

18 Claims, 11 Drawing Sheets

(56) References Cited

U.S. PATENT DOCUMENTS

| | | |
|---|---|---|
| 2005/0130923 A1 | 6/2005 | Bhat et al. |
| 2007/0287831 A1 | 12/2007 | Seth et al. |
| 2008/0039618 A1 | 2/2008 | Allerson et al. |
| 2010/0069472 A1 | 3/2010 | Hung et al. |
| 2013/0059902 A1 | 3/2013 | Corey et al. |

FOREIGN PATENT DOCUMENTS

| | | |
|---|---|---|
| WO | WO 2005/021570 | 3/2005 |
| WO | WO 2007/134181 | 11/2007 |
| WO | WO 2008/018795 | 2/2008 |
| WO | WO 2008/036406 | 3/2008 |
| WO | WO 2008/101157 | 8/2008 |
| WO | WO 2008/150729 | 12/2008 |
| WO | WO 2008/154401 | 12/2008 |
| WO | WO 2009/006478 | 1/2009 |
| WO | WO 2010/014592 | 2/2010 |
| WO | WO 2010/048549 | 4/2010 |
| WO | WO 2010/048585 | 4/2010 |
| WO | WO 2011/005860 | 1/2011 |
| WO | WO 2011/097388 | 8/2011 |
| WO | WO 2011/097614 | 8/2011 |
| WO | WO 2011/097641 | 8/2011 |
| WO | WO 2011/133871 | 10/2011 |
| WO | WO 2011/139699 | 11/2011 |
| WO | WO 2011/139702 | 11/2011 |
| WO | WO 2012/012443 | 1/2012 |

OTHER PUBLICATIONS

Davis et al., "Expansion of a CUG trinucleotide repeat in the 3' untranslated region of myotonic dystrophy protein kinase transcripts results in nuclear retention of transcripts" PNAS (1997) 94:7388-7393.
Elayadi et al., "Application of PNA and LNA oligomers to chemotherapy" Curr. Opinion Invens. Drugs (2001) 2: 558-561.
Englisch et al., "Chemically Modified Oligonucleotides as Probes and Inhibitors" Agnew Chem. Int. Ed. Engl. (1991) 30:613-629.
Freier et al., "The ups and downs of nucleic acid duplex stability: structure-stability studies on chemically-modified DNA:RNA duplexes" Nucleic Acids Research (1997) 25(22):4429-4443.
Frieden et al., "Expanding the design horizon of antisense oligonucleotides with alpha-L-LNA" Nucleic Acids Research (2003) 31(21):6365-6372.
Kabanov et al., "A new class of antivirals: antisense oligonucleotides combined with a hydrophobic substituent effectively inhibit influenza virus reproduction and synthesis of virus-specific proteins in MDCK cells" FEBS Lett. (1990) 259:327.
Koshkin et al., "LNA (locked nucleic acids): Synthesis of the adenine, cytosine, guanine, 5-methylcytosine, thymine and uracil bicyclonucleoside monomers, oligomerisation, and unprecedented nucleic acid recognition" Tetrahedron (1998) 54:3607-3630.
Krol et al., "Ribonuclease dicer cleaves triplet repeat hairpins into shorter repeats that silence specific targets" Molecular Cell (2007) 25:575-586.
Kroschwitz The Concise Encyclopedia of Polymer Science and Engineering, Kroschwitz, J.I., Ed., John Wiley & Sons, 1990, 858-859.
Kumar et al., "The first analogues of LNA (locked nucleic acids): phosphorothioate-LNA and 2'-thio-LNA" Bioorg Med Chem Lett. (1998) 8:2219-2222.
Letsinger et al., "Cholesteryl-conjugated oligonucleotides: Synthesis, properties, and activity as inhibitors of replication of human immunodeficiency virus in cell culture" PNAS (1989) 86:6553-6556.
Leumann, "DNA Analogues: From Supramolecular Principles to Biological Properties" Bioorg. & Med. Chem. (2002) 10:841-854.
Lin et al., "Neurological abnormalities in a knock-in mouse model of Huntington's disease" Human Molecular Genetics (2001) 10(2):137-144.

Maher et al., "Comparative hybrid arrest by tandem antisense oligodeoxyribonucleotides or oligodeoxyribonucleoside methylphosphonates in a cell-free system" Nuc. Acid. Res. (1988) 16:341-3358.
Mankodi et al., "Expanding CUG Repeats Trigger Aberrant Splicing of CIC-1 Chloride Channel Pre-mRNA and Hyperexcitability of Skeletal Muscle in Myotonic Dystrophy" Mol. Cell. (2002) 10:35-44.
Manoharan et al., "Chemical Modifications to Improve Uptake and Bioavailability of Antisense Oligonucleotides" Ann. N. Y. Acad. Sci. (1992) 660: 306-309.
Manoharan et al., "Introduction of a Lipophilic Thioether Tether in the Minor Groove of Nucleic Acids for Antisense Applications" Bioorg. Med. Chem. Lett. (1993) 3(12):2765-2770.
Manoharan et al., "Cholic Acid-Oligonucleotide Conjugates for Antisense Applications" Bioorg. Med. Chem. Lett. (1994) 4:1053-1060.
Manoharan et al., "Oligonucleotide Conjugates: Alteration of the Pharmacokinetic Properties of Antisense Agents" Nucleosides & Nucleotides (1995) 14(3-5):969-973.
Manoharan et al., "Lipidic Nucleic Acids" Tetrahedron Lett. (1995) 36(21):3651-3654.
Mishra et al., "Improved leishmanicidal effect of phosphorotioate antisense oligonucleotides by LDL-mediated delivery" Biochim. Biophys. Acta (1995) 1264:229-237.
O'Rourke et al., "Mechanisms of RNA-mediated Disease" J. Biol. Chem. (2009) 284(12): 7419-7423.
Oberhauser et al., "Effective incorporation of 2'-O-methyl-oligoribonucleotides into liposomes and enhanced cell association through modifications with thiocholesterol" Nucl. Acids Res. (1992) 20(3):533-538.
Orum et al., "Locked nucleic acids: A promising molecular family for gene-function analysis and antisense drug development" Curr. Opinion Mol. Ther. (2001) 3:239-243.
Saison-Behmoaras et al., "Short modified antisense oligonucleotides directed against Ha-ras point mutation induce selective cleavage of the mRNA and inhibit T24 cells proliferation" EMBO J. (1991) 10(5):1111-1118.
Sanghvi, Chapter 15, Antisense Research and Applications, Crooke and Lebleu ed., CRC Press (1993).
Shea et al., "Synthesis, hybridization properties and antiviral activity of lipid-oligodeoxynucleotide conjugates" Nucl. Acids Res. (1990) 18(13):3777-3783.
Singh et al., "LNA (locked nucleic acids): synthesis and high-affinity nucleic acid recognition" Chem. Commun. (1998) 455-456.
Singh et al., "Synthesis of 2'-amino-LNA: A novel conformationally restricted high-affinity oligonucleotide analogue with a handle" J. Org. Chem. (1998) 63: 10035-10039.
Srivastava et al., "Five- and Six-Membered Conformationally Locked 2',4'-Carbocyclic ribo-Thymidines: Synthesis, Structure, and Biochemical Studies" J. Am. Chem. Soc. (2007) 129(26):8362-8379.
Svinarchuk et al., "Inhibition of HIV proliferation in MT-4 cells by antisense oligonucleotide conjugated to lipophilic groups" Biochimie (1993) 75:49-54.
Wahlestedt et al., "Potent and nontoxic antisense oligonucleotide containing locked nucleic acids" Proc. Natl. Acad. Sci. USA (2000) 97: 5633-5638.
Wheeler et al., "Reversal of RNA dominance by displacement of protein sequestered on triplet repeat RNA" Science (2009) 325:336-339.
Zhou et al., "Fine Tuning of Electrostatics around the Internucleotidic Phosphate through Incorporation of Modified 2',4'-Carbocyclic-LNAs and -ENAs Leads to Significant Modulation of Antisense Properties" J. Org. Chem. (2009) 74:118-134.
International Search Report for application PCT/US12/52874 dated Nov. 28, 2012.
Hu et al. "Allele-specific silencing of mutant huntingtin & ataxin-3 genes by targeting expanded CAG repeats in mRNAs" Nat. Biotech. (2009) 27: 478-484.

* cited by examiner

Effects of reducing cellular Argonaute levels on inhibition of HTT expression by ISIS 537775

Effects of reducing cellular Argonaute levels on inhibition of HTT expression by siRNA, BBRC Western analysis of ISIS 537775 on selective inhibition of mut HTT protein expression over 14 days Quantitation of Western analysis of HTT protein expression of ISIS 537775 over 14 days Effect of ISIS 537775 as a duplex on selective inhibition of mut HTT protein expression targeting HTT CAG repeat region Effect of ISIS 553822 on selectivity and inhibition of HTT protein expression in GM04719 patient derived fibroblast cells Effect of ISIS 537775 and 553822 on HTT mRNA levels in vitro Effect of ISIS 557426 on genes containing trinucleotide repeats in vitro Western analysis of HTT protein expression on allele-selective inhibition by modified ssRNA 537775 in Q150/Q7 mouse frontal cortex Quantitation of Western analysis of HTT protein expression on allele-selective inhibition by modified ssRNA 537775 in Q150/Q7 mouse frontal cortex Q-PCR analysis of HTT mRNA levels in Q150/Q7 mouse frontal cortex after treatment with vehicle, modified ssRNA 537775 or control MOE gapmer 387898

Western analysis of HTT protein expression on allele-selective inhibition by modified ssRNA 537775 in different brain regions of Q150/Q7 mouse Quantitation of Western analysis of HTT protein expression on allele-selective inhibition by modified ssRNA 537775 in different brain regions of Q150/Q7 mouse

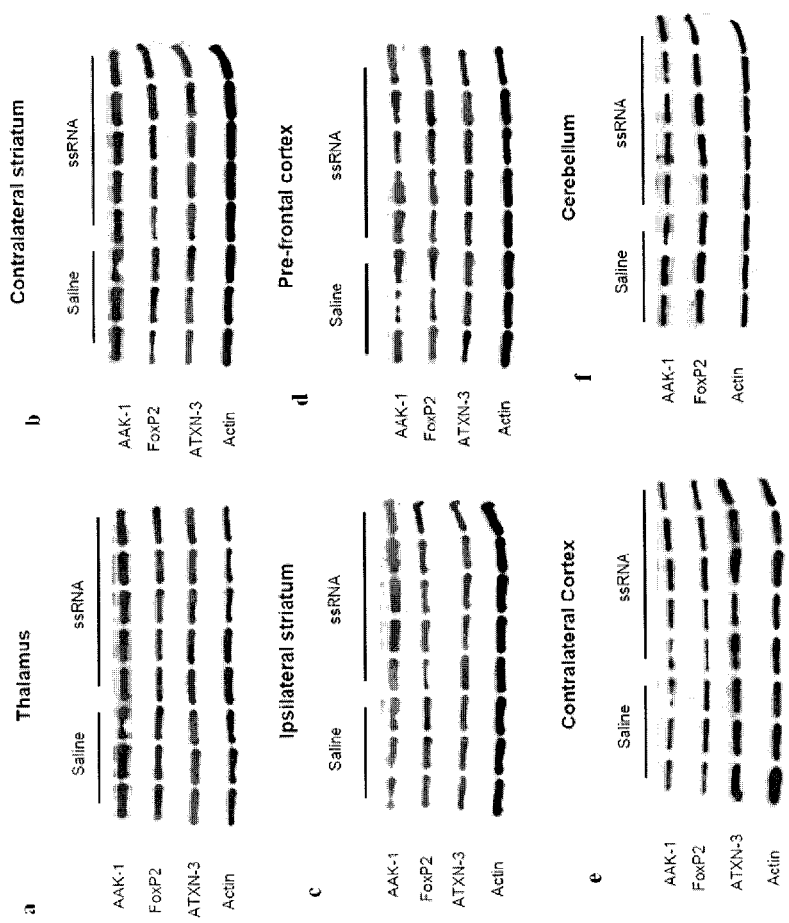
Figures 9a-f
Western analysis of HTT protein expression of several CAG-repeat-containing genes in various brain tissues of Q150/Q7 mouse after modified ssRNA 537775 treatment

METHODS AND COMPOUNDS USEFUL IN CONDITIONS RELATED TO REPEAT EXPANSION

CROSS REFERENCED TO RELATED APPLICATIONS

This application is a U.S. National Phase filing under 35 U.S.C. § 371 claiming priority to International Serial No. PCT/US2012/052874 filed Aug. 29, 2012, which claims priority to U.S. Provisional Application 61/528,719, filed Aug. 29, 2011, each of which is incorporated herein by reference in its entirety.

STATEMENT AS TO FEDERALLY SPONSORED RESEARCH

This invention was made with government support under Grant Number GM073042 awarded by the National Institutes of Health. The government has certain rights in the invention.

SEQUENCE LISTING

The present application is being filed along with a Sequence Listing in electronic format. The Sequence Listing is provided as a file entitled CORE0097USASEQ_ST25.txt, created on Feb. 24, 2014, which is 16 Kb in size. The information in the electronic format of the sequence listing is incorporated herein by reference in its entirety.

BACKGROUND OF THE INVENTION

The present disclosure pertains generally to chemically-modified oligonucleotides for use in research, diagnostics, and/or therapeutics.

Certain RNA molecules are known to include repeat regions consisting essentially of repeating units of 3-5 nucleotides. Depending on the particular gene, the repeat region of a normal wild-type RNA molecule may comprise from about 5 up to about 11,000 copies of the repeating unit. In certain instances, the number of such repeating units can become increased and the resulting expanded repeat-containing RNA molecule may be disruptive to the cell. Certain diseases can result.

Certain oligonucleotides having nucleobase sequences complementary to a repeat region of a target RNA have been described, for example U.S. Patent Ser. No. 61/302,454; PCT International Application No. PCT/US2011/024019.

SUMMARY OF THE INVENTION

In certain embodiments, the present invention provides compounds and methods for modulating the expanded repeat-containing target nucleic acids. The present invention includes, but is not limited to the following numbered embodiments.

Embodiment 1

A compound comprising a single-stranded oligonucleotide consisting of 13 to 30 linked nucleosides and having a nucleobase sequence complementary to a repeat region of an expanded repeat-containing target RNA, wherein the 5'-terminal nucleoside of the single-stranded oligonucleotide comprises a stabilized phosphate moiety and an internucleoside linking group linking the 5'-terminal nucleoside to the remainder of the oligonucleotide.

Embodiment 2

The compound of embodiment 1, wherein the 5'-terminal nucleoside of the single-stranded oligonucleotide has Formula I:

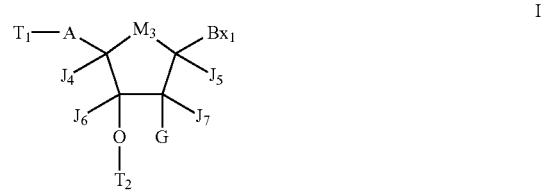

wherein:
$T_1$ is a phosphorus moiety;
$T_2$ is an internucleoside linking group linking the 5'-terminal nucleoside of Formula I to the remainder of the oligonucleotide;
A has a formula selected from among:

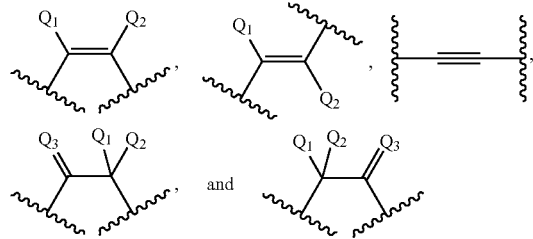

$Q_1$ and $Q_2$ are each independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl, and $N(R_3)(R_4)$;
$Q_3$ is selected from among: O, S, $N(R_5)$, and $C(R_6)(R_7)$;
each $R_3$, $R_4R_5$, $R_6$ and $R_7$ is independently selected from among: H, $C_1$-$C_6$ alkyl, substituted $C_1$-$C_6$ alkyl, and $C_1$-$C_6$ alkoxy;
$M_3$ is selected from among: O, S, $NR_{14}$, $C(R_{15})(R_{16})$, $C(R_{15})(R_{16})C(R_{17})(R_{18})$, $C(R_{15})=C(R_{17})$, $OC(R_{15})(R_{16})$, and $OC(R_{15})(Bx_2)$;
$R_{14}$ is selected from among: H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;
$R_{15}$, $R_{16}$, $R_{17}$ and $R_{18}$ are each independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;
if $Bx_2$ is present, then $Bx_2$ is a nucleobase and $Bx_1$ is selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;
if $Bx_2$ is not present, then $Bx_1$ is a nucleobase;
either each of $J_4$, $J_5$, $J_6$ and $J_7$ is independently selected from among: H, halogen, $C_1$-$C_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl, and substituted C$_2$-C$_6$ alkynyl;

or J$_4$ forms a bridge with one of J$_5$ or J$_7$ wherein the bridge comprises from 1 to 3 linked biradical groups selected from O, S, NR$_{19}$, C(R$_{20}$)(R$_{21}$), C(R$_{20}$)=C(R$_{21}$); C[=C(R$_{20}$)(R$_{21}$)] and C(=O) and the other two of J$_5$, J$_6$ and J$_7$ are independently selected from among: H, halogen, C$_1$-C$_6$ alkyl, substituted C$_1$-C$_6$ alkyl, C$_r$ C$_6$ alkoxy, substituted C$_1$-C$_6$ alkoxy, C$_2$-C$_6$ alkenyl, substituted C$_2$-C$_6$ alkenyl, C$_2$-C$_6$ alkynyl, and substituted C$_2$-C$_6$ alkynyl;

each R$_{19}$, R$_{20}$ and R$_{21}$ is independently selected from among: H, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;

G is selected from among: H, OH, halogen, O—[C(R$_8$)(R$_9$)]$_n$—[(C=O)$_m$—X$_1$]$_j$—Z, and a conjugate group;

each R$_8$ and R$_9$ is independently selected from among: H, halogen, C$_1$-C$_6$ alkyl, and substituted C$_1$-C$_6$ alkyl;

X$_1$ is O, S or N(E$_1$);

Z is selected from among: H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, and N(E$_2$)(E$_3$);

E$_1$, E$_2$ and E$_3$ are each independently selected from among: H, C$_1$-C$_6$ alkyl, and substituted C$_1$-C$_6$ alkyl;

n is from 1 to 6;

m is 0 or 1;

j is 0 or 1;

provided that, if j is 1, then Z is other than halogen or N(E$_2$)(E$_3$);

each substituted group comprises one or more optionally protected substituent groups independently selected from among: a halogen, OJ$_1$, N(J$_1$)(J$_2$), =NJ$_1$, SJ$_1$, N$_3$, CN, OC(=X$_2$)J$_1$, OC(=X$_2$)N(J$_1$)(J$_2$), and C(=X$_2$)N(J$_1$)(J$_2$);

X$_2$ is O, S or NJ$_3$; and each J$_1$, J$_2$ and J$_3$ is independently selected from among: H and C$_1$-C$_6$ alkyl.

Embodiment 3

The compound of embodiment 2, wherein M$_3$ is selected from among: O, CH=CH, OCH$_2$, and OC(H)(Bx$_2$).

Embodiment 4

The compound of embodiment 2, wherein M$_3$ is O.

Embodiment 5

The compound of any of embodiments 2-4, wherein each of J$_4$, J$_5$, J$_6$ and J$_7$ is H.

Embodiment 6

The compound of any of embodiments 2-5, wherein J$_4$ forms a bridge with either J$_5$ or J$_7$.

Embodiment 7

The compound of any of embodiments 2-6, wherein A has the formula:

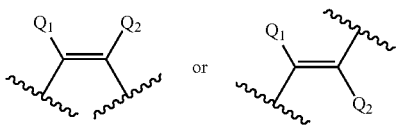

wherein:

Q$_1$ and Q$_2$ are each independently selected from among: H, halogen, C$_1$-C$_6$ alkyl, substituted C$_1$-C$_6$ alkyl, C$_1$-C$_6$ alkoxy, and substituted C$_1$-C$_6$ alkoxy.

Embodiment 8

The compound of embodiment 7, wherein each of Q$_1$ and Q$_2$ is H.

Embodiment 9

The compound of embodiment 7, wherein Q$_1$ and Q$_2$ are each independently selected from among: H and a halogen.

Embodiment 10

The compound of embodiment 7, wherein one of Q$_1$ and Q$_2$ is H and the other of Q$_1$ and Q$_2$ is F, CH$_3$ or OCH$_3$.

Embodiment 11

The compound of any of embodiments 2 to 10, wherein T$_1$ has the formula:

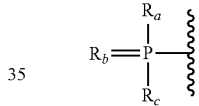

wherein:

R$_a$ and R$_c$ are each independently selected from among: protected hydroxyl, protected thiol, C$_1$-C$_6$ alkyl, substituted C$_1$-C$_6$ alkyl, C$_1$-C$_6$ alkoxy, substituted C$_1$-C$_6$ alkoxy, protected amino or substituted amino; and R$_b$ is O or S.

Embodiment 12

The compound of embodiment 11, wherein R$_b$ is O and R$_a$ and R$_c$ are each, independently selected from among: OCH$_3$, OCH$_2$CH$_3$, OCH(CH$_3$)$_2$.

Embodiment 13

The compound of any of embodiments 2 to 12, wherein G is selected from among: a halogen, OCH$_3$, OCH$_2$F, OCHF$_2$, OCF$_3$, OCH$_2$CH$_3$, O(CH$_2$)$_2$F, OCH$_2$CHF$_2$, OCH$_2$CF$_3$, OCH$_2$—CH=CH$_2$, O(CH$_2$)$_2$—OCH$_3$, O(CH$_2$)$_2$—SCH$_3$, O(CH$_2$)$_2$—OCF$_3$, O(CH$_2$)$_3$—N(R$_{10}$)(R$_{11}$), O(CH$_2$)$_2$—ON(R$_{10}$)(R$_{11}$), O(CH$_2$)$_2$—O(CH$_2$)$_2$—N(R$_{10}$)(R$_{11}$), OCH$_2$C(=O)—N(R$_{10}$)(R$_{11}$), OCH$_2$C(=O)—N(R$_{12}$)—(CH$_2$)$_2$—N(R$_{10}$)(R$_{11}$), and O(CH$_2$)$_2$—N(R$_{12}$)—C(=NR$_{13}$)[N(R$_{10}$)(R$_{11}$)]; wherein R$_{10}$, R$_{11}$, R$_{12}$ and R$_{13}$ are each, independently, H or C$_1$-C$_6$ alkyl.

Embodiment 14

The compound of any of embodiments 2-13, wherein G is selected from among: a halogen, OCH$_3$, OCF$_3$, OCH$_2$CH$_3$, $OCH_2CF_3$, $OCH_2$—CH═$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—N(H)—$(CH_2)_2$—$N(CH_3)_2$, and $OCH_2$—N(H)—C(═NH)$NH_2$.

Embodiment 15

The compound of any of embodiments 2-14, wherein G is selected from among: F, $OCH_3$, and $O(CH_2)_2$—$OCH_3$.

Embodiment 16

The compound of embodiment 15, wherein G is $O(CH_2)_2$—$OCH_3$.

Embodiment 17

The compound of any of embodiments 2-13, wherein G is a conjugate group.

Embodiment 18

The compound of claim 17, wherein the conjugate of the conjugate group is selected from among: an intercalator, a polyamine, a polyamide, a polyethylene glycol, a thioether, a polyether, a cholesterol, a thiocholesterol, a cholic acid moiety, a folate, a lipid, a phospholipid, biotin, phenazine, phenanthridine, anthraquinone, adamantane, acridine, a fluorescein, a rhodamine, and a coumarin.

Embodiment 19

The compound of embodiments 17 or 18, wherein the conjugate of the conjugate group is selected from among: cholesterol, palmityl, stearoyl, lithocholic-oleyl, $C_{22}$ alkyl, $C_{20}$ alkyl, $C_{16}$ alkyl, $C_{18}$ alkyl, and $C_{10}$ alkyl.

Embodiment 20

The compound of any of embodiments 17-19, wherein the conjugate group comprises a linker.

Embodiment 21

The compound of embodiment 20, wherein the linker is selected from among: hexanamide, 8-amino-3,6-dioxaoctanoic acid (ADO), succinimidyl 4-(N-maleimidomethyl)cyclohexane-1-carboxylate (SMCC), 6-aminohexanoic acid (AHEX or AHA), substituted $C_1$-$C_{10}$ alkyl, substituted or unsubstituted $C_2$-$C_{10}$ alkenyl, and substituted or unsubstituted $C_2$-$C_{10}$ alkynyl.

Embodiment 22

The compound of any of embodiments 2-21, wherein the nucleobase is a modified nucleobase.

Embodiment 23

The compound of any of embodiments 2-22, wherein the nucleobase is a pyrimidine, substituted pyrimidine, purine or substituted purine.

Embodiment 24

The compound of any of embodiments 2-23, wherein the nucleobase is uracil, thymine, cytosine, 5-methylcytosine, adenine or guanine.

Embodiment 25

The compound of any of embodiments 2-24, wherein the 5'-terminal nucleoside of the single-stranded oligonucleotide has Formula III:

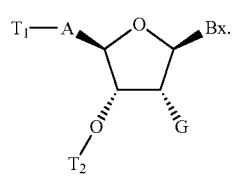

III

Embodiment 26

The compound of embodiment 25, wherein A has the formula:

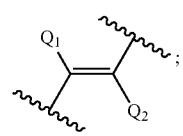

wherein $Q_1$ and $Q_2$ are each independently selected from among: H, a halogen, $C_1$-$C_6$ alkyl, substituted $C_1$-$C_6$ alkyl, $C_1$-$C_6$ alkoxy, and substituted $C_1$-$C_6$ alkoxy.

Embodiment 27

The compound of embodiment 26, wherein $Q_1$ and $Q_2$ are each independently selected from among: H, F, $CH_3$, and $OCH_3$.

Embodiment 28

The compound of any of embodiments 2-27, wherein the 5'-terminal nucleoside has Formula V:

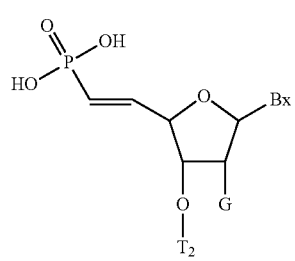

V wherein:
Bx is selected from among: uracil, thymine, cytosine, 5-methyl cytosine, adenine, and guanine;
$T_2$ is a phosphorothioate internucleoside linking group linking the compound of Formula V to the remainder of the oligonucleotide; and
G is selected from among: a halogen, $OCH_3$, $OCF_3$, $OCH_2CH_3$, $OCH_2CF_3$, $OCH_2$—CH═$CH_2$, $O(CH_2)_2$—$OCH_3$, $O(CH_2)_2$—$O(CH_2)_2$—$N(CH_3)_2$, $OCH_2C(=O)$—N(H)$CH_3$, $OCH_2C(=O)$—N(H)—$(CH_2)_2$—$N(CH_3)_2$, $OCH_2$—N(H)—C(═NH)$NH_2$, and a conjugate group.

Embodiment 29

The compound of any of embodiments 1-28, wherein the remainder of the oligonucleotide comprises at least one RNA-like nucleoside.

Embodiment 30

The compound of embodiment 29, wherein essentially each nucleoside of the remainder of the oligonucleotide is an RNA-like nucleoside.

Embodiment 31

The compound of embodiment 30, wherein each nucleoside of the remainder of the oligonucleotide is an RNA-like nucleoside.

Embodiment 32

The compound of any of embodiments 29-31, wherein each RNA-like nucleoside is independently selected from among: a 2'-endo furanosyl nucleoside and an RNA-surrogate nucleoside.

Embodiment 33

The compound of embodiment 32, wherein each RNA-like nucleoside is a 2'-endo furanosyl nucleoside.

Embodiment 34

The compound of embodiment 33, wherein each RNA-like nucleoside is selected from among: 2'-F, 2'-MOE, 2'-OMe, LNA, F-HNA, and cEt.

Embodiment 35

The compound of any of embodiments 1-34, wherein the remainder of the oligonucleotide comprises at least one region having sugar motif:

-[(A)$_x$-(B)$_y$-(A)$_z$]$_q$- wherein
A is a modified nucleoside of a first type,
B is a modified nucleoside of a second type;
each x and each y is independently 1 or 2;
z is 0 or 1;
q is 1-15;

Embodiment 36

The compound of embodiment 35, wherein the modifications of the first type and the modifications of the second type are selected from among: 2'-F, 2'-OMe, and F-HNA.

Embodiment 37

The compound of embodiment 35, wherein the modifications of the first type are 2'-F and the modifications of the second type are 2'-OMe.

Embodiment 38

The compound of embodiment 35, wherein the modifications of the first type are 2'-OMe and the modifications of the second type are 2'-F.

Embodiment 39

The compound of any of embodiments 35-38, wherein each x and each y is 1.

Embodiment 40

The compound of any of embodiments 1-39, wherein the remainder of the oligonucleotide comprises 1-4 3'terminal nucleosides, each comprising the same sugar modification, wherein the sugar modification of the 1-4 3'terminal nucleosides is different from the sugar modification of the immediately adjacent nucleoside.

Embodiment 41

The compound of embodiment 40, wherein the 3'-terminal nucleosides are each 2'-MOE nucleosides.

Embodiment 42

The compound of embodiment 40 or 41 comprising two 3'-terminal nucleosides.

Embodiment 43

The compound of any of embodiments 1-42, comprising at least one modified internucleoside linkage.

Embodiment 44

The compound of embodiment 43, wherein each internucleoside linkage is selected from phosphorothioate and phosphodiester.

Embodiment 45

The compound of embodiment 43 or 44, wherein each of the 6-10 3'-most internucleoside linkages is phosphorothioate linkage.

Embodiment 46

The compound of any of embodiments 43-45, wherein the 5'-most internucleoside linkage is a phosphorothioate linkage.

Embodiment 47

The compound of any of embodiments 43-46, comprising a region of alternating linkages.

Embodiment 48

The compound of any of embodiments 1-47, comprising a 5'region having the motif:

-s-(A-s-B-o-A)$_x$(-s-B)$_Y$    (Nucleoside of Formula I, III, or V)

wherein:
A is a nucleoside of a first type;
B is a nucleoside of a second type;
s is a phosphorothioate linkage;
o is a phosphodiester linkage;
X is 1-8; and
Y is 1 or 0.

Embodiment 49

The compound of any of embodiments 1-48, comprising a 3'region having the motif:

-(A-s-B-s-A)$_z$(-s-B)$_q$-s-(D)-(s-D)$_r$.

wherein:
s is a phosphorothioate linkage;
A is a nucleoside of a first type;
B is a nucleoside of a second type;
D is a nucleoside of a third type;
Z is 1-5;
q is 1 or 0; and
and r is 0-3.

Embodiment 50

The compound embodiment 48 or 49, wherein A is a 2'-F nucleoside.

Embodiment 51

The compound of any of embodiments 48-50, wherein B is a 2'-OMe nucleoside.

Embodiment 52

The compound of any of embodiments 49-51, wherein D is a 2'-MOE nucleoside.

Embodiment 53

The compound of any of embodiments 49-52, wherein the oligonucleotide comprises a hybridizing region and a 3'-terminal region, wherein the hybridizing region comprises nucleosides A and B and the terminal region comprising nucleosides D, wherein the hybridizing region is complementary to the repeat region of the expanded repeat-containing target RNA.

Embodiment 54

The compound of any of embodiments 1-48, comprising the motif:

-s-A-s-B-o-A-s-B-o-A-s-B-o-A-s-B-o-A-s-B-o-A-s-
  B-o-A-s-B-s-A-s-B-s-A-s-B-s-D-s-D-(Nucleoside of Formula V)

wherein:
s is a phosphorothioate linkage;
A is a nucleoside of a first type;
B is a nucleoside of a second type; and
D is a nucleoside of a third type.

Embodiment 55

The compound of any of embodiments 1-48, consisting of the motif:

-s-A-s-B-o-A-s-B-o-A-s-B-o-A-s-B-o-A-s-B-o-A-s-
  B-o-A-s-B-s-A-s-B-s-A-s-B-s-D-s-D-(Nucleoside of Formula V)

wherein:
s is a phosphorothioate linkage;
A is a nucleoside of a first type;
B is a nucleoside of a second type; and
D is a nucleoside of a third type.

Embodiment 56

The compound of embodiment 54 or 55, wherein A is a 2'-F nucleoside.

Embodiment 57

The compound of any of embodiments 54-56, wherein B is a 2'-OMe nucleoside.

Embodiment 58

The compound of any of embodiments 54-57, wherein D is a 2'-MOE nucleoside.

Embodiment 59

The compound of any of embodiments 1-58, wherein the remainder of the oligonucleotide comprises at least one conjugate group.

Embodiment 60

The compound of embodiment 59, wherein the conjugate of the conjugate group is selected from among: an intercalator, a polyamine, a polyamide, a polyethylene glycol, a thioether, a polyether, a cholesterol, a thiocholesterol, a cholic acid moiety, a folate, a lipid, a phospholipid, biotin, phenazine, phenanthridine, anthraquinone, adamantane, acridine, a fluorescein, a rhodamine, and a coumarin.

Embodiment 61

The compound of embodiments 59 or 60, wherein the conjugate of the conjugate group is selected from among: cholesterol, palmityl, stearoyl, lithocholic-oleyl, $C_{22}$ alkyl, $C_{20}$ alkyl, $C_{16}$ alkyl, $C_{18}$ alkyl, and $C_{10}$ alkyl.

Embodiment 62

The compound of any of embodiments 59-61, wherein the conjugate group comprises a linker.

Embodiment 63

The compound of embodiment 62, wherein the linker is selected from among: hexanamide, 8-amino-3,6-dioxaoctanoic acid (ADO), succinimidyl 4-(N-maleimidomethyl) cyclohexane-1-carboxylate (SMCC), 6-aminohexanoic acid (AHEX or AHA), substituted $C_1$-$C_{10}$ alkyl, substituted or unsubstituted $C_2$-$C_{10}$ alkenyl, and substituted or unsubstituted $C_2$-$C_{10}$ alkynyl.

Embodiment 64

The compound of any of embodiments 1-63, wherein the oligonucleotide is 100% complementary to the repeat region of the expanded repeat-containing target RNA.

Embodiment 65

The compound of any of embodiments 1-63, wherein the oligonucleotide has one mismatch relative to the repeat region of the expanded repeat-containing target RNA.

Embodiment 66

The compound of any of embodiments 1-63, wherein the oligonucleotide has two mismatches relative to the repeat region of the expanded repeat-containing target RNA.

Embodiment 67

The compound of any of embodiments 1-63, wherein the oligonucleotide has three mismatches relative to the repeat region of the expanded repeat-containing target RNA.

Embodiment 68

The compound of any of embodiments 1-63, wherein the oligonucleotide has four mismatches relative to the repeat region of the expanded repeat-containing target RNA.

Embodiment 69

The compound of any of embodiments 1-63, wherein the oligonucleotide has five mismatches relative to the repeat region of the expanded repeat-containing target RNA.

Embodiment 70

The compound of any of embodiments 1-69, wherein the oligonucleotide comprises a hybridizing region and 0-4 3'-terminal nucleosides.

Embodiment 71

The compound of any of embodiments 1-69, wherein the oligonucleotide comprises a hybridizing region and 1-4 3'-terminal nucleosides.

Embodiment 72

The compound of embodiment 70 or 71, wherein the hybridizing region is 100% complementary to the repeat region of the expanded repeat-containing target RNA.

Embodiment 73

The compound of embodiment 70 or 71, wherein the hybridizing region has one mismatch relative to the repeat region of the expanded repeat-containing target RNA.

Embodiment 74

The compound of embodiment 70 or 71, wherein the hybridizing region has two mismatches relative to the repeat region of the expanded repeat-containing target RNA.

Embodiment 75

The compound of embodiment 70 or 71 wherein the hybridizing region has three mismatches relative to the repeat region of the expanded repeat-containing target RNA.

Embodiment 76

The compound of embodiment 70 or 71 wherein the hybridizing region has four mismatches relative to the repeat region of the expanded repeat-containing target RNA.

Embodiment 77

The compound of embodiment 70 or 71 wherein the hybridizing region has five mismatches relative to the repeat region of the expanded repeat-containing target RNA.

Embodiment 78

The compound of any of embodiments 65-77, having a mismatch at the eighth nucleobase from the 5'-end of the hybridizing region.

Embodiment 79

The compound of any of embodiments 65-78, having a mismatch at the ninth nucleobase from the 5'-end of the hybridizing region.

Embodiment 80

The compound of any of embodiments 65-79, having a mismatch at the tenth nucleobase from the 5'-end of the hybridizing region.

Embodiment 81

The compound of any of embodiments 65-80, having a mismatch at the ninth nucleobase from the 3'-end of the hybridizing region.

Embodiment 82

The compound of any of embodiments 65-81, having a mismatch at the tenth nucleobase from the 3'-end of the hybridizing region.

Embodiment 83

The compound of any of embodiments 65-82, having a mismatch at the eleventh nucleobase from the 3'-end of the hybridizing region.

Embodiment 84

The compound of any of embodiments 1-63, wherein the oligonucleotide comprises a hybridizing region having two or more mismatches relative to the repeat region of the expanded repeat-containing target RNA, and wherein each of the mismatches is adjacent to one another.

Embodiment 85

The compound of any of embodiments 1-63, wherein the oligonucleotide comprises a hybridizing region having three or more mismatches relative to the repeat region of the expanded repeat-containing target RNA, and wherein each of the mismatches is adjacent to one another.

Embodiment 86

The compound of any of embodiments 1-63, wherein the oligonucleotide comprises a hybridizing region having two mismatches relative to the repeat region of the expanded

Embodiment 87

The compound of embodiment 86, wherein the mismatches are located at the $9^{th}$ and $10^{th}$ nucleobases from the 5'-terminal nucleoside of the compound.

Embodiment 88

The compound of embodiment 86, wherein the mismatches are located at the $10^{th}$ and $11^{th}$ nucleobases from the 5'-terminal nucleoside of the compound.

Embodiment 89

The compound of embodiment 86, wherein the mismatches are located at the $8^{th}$ and $9^{th}$ nucleobases from the 5'-terminal nucleoside of the compound.

Embodiment 90

The compound of any of embodiments 1-63, wherein the oligonucleotide comprises a hybridizing region having three mismatches relative to the repeat region of the expanded repeat-containing target RNA, and wherein each of the mismatches is adjacent to one another.

Embodiment 91

The compound of embodiment 90, wherein the mismatches are located at the $9^{th}$, $10^{th}$, and $11^{th}$ nucleobases from the 5'-terminal nucleoside of the compound.

Embodiment 92

The compound of embodiment 90, wherein the mismatches are located at the $10^{th}$, $11^{th}$ and $12^{th}$ nucleobases from the 5'-terminal nucleoside of the compound.

Embodiment 93

The compound of embodiment 90, wherein the mismatches are located at the $8^{th}$, $9^{th}$, and $10^{th}$ nucleobases from the 5'-terminal nucleoside of the compound.

Embodiment 94

The compound of any of embodiments 1-63, wherein the oligonucleotide comprises a hybridizing region having four mismatches relative to the repeat region of the expanded repeat-containing target RNA, and wherein each of the mismatches is adjacent to one another.

Embodiment 95

The compound of embodiment 94, wherein the mismatches are located at the $8^{th}$, $9^{th}$, $10^{th}$, and $11^{th}$ nucleobases from the 5'-terminal nucleoside of the compound.

Embodiment 96

The compound of embodiment 94, wherein the mismatches are located at the $9^{th}$, $10^{th}$, $11^{th}$ and $12^{th}$ nucleobases from the 5'-terminal nucleoside of the compound.

Embodiment 97

The compound of embodiment 94, wherein the mismatches are located at the $7^{th}$, $8^{th}$, $9^{th}$, and $10^{th}$ nucleobases from the 5'-terminal nucleoside of the compound.

Embodiment 98

The compound of any of embodiments 69-97, wherein one or more of the 3'-terminal nucleosides is not complementary to the target RNA.

Embodiment 99

The compound of any of embodiments 69-98, wherein the nucleobase of each 3'-terminal nucleoside is a purine.

Embodiment 100

The compound of embodiment 99, wherein the nucleobase of each 3'-terminal nucleoside is an adenine.

Embodiment 101

The compound of any of embodiments 1-100, wherein the repeat region of the expanded repeat-containing RNA consists of a repeating quartet.

Embodiment 102

The compound of embodiment 101, wherein the repeat region of the expanded repeat-containing RNA consists of repeating units of CCUG or AUUCU.

Embodiment 103

The compound of any of embodiments 1-100, wherein the repeat region of the expanded repeat-containing RNA consists of a repeating triplet.

Embodiment 104

The compound of embodiment 103, wherein the repeating triplet is selected from: CAG, CUG, CGG, GCC, and GAA.

Embodiment 105

The compound of embodiment 104, wherein the repeating triplet is CAG.

Embodiment 106

The compound of embodiment 104, wherein the repeating triplet is CUG.

Embodiment 107

The compound of any of embodiments 1-106 wherein the expanded repeat-containing RNA is associated with a disease.

Embodiment 108

The compound of embodiment 107, wherein the disease is selected from among: ataxin 3, atrophin 1, fragile X syndrome, Friedrich's ataxia, Huntington's disease, Huntington's disease-like 2, myotonic dystrophy, spinal and bulbar muscular atrophy, and spinocerebellar ataxia.

Embodiment 109

The compound of embodiment 108, wherein the disease is Huntington's disease.

Embodiment 110

The compound of embodiment 108, wherein the disease is myotonic dystrophy.

Embodiment 111

The compound of embodiment 110, wherein the myotonic dystrophy is myotonic dystrophy type 1.

Embodiment 112

The compound of embodiment 110, wherein the myotonic dystrophy is myotonic dystrophy type 2.

Embodiment 113

The oligomeric compound of embodiment 108, wherein the disease is spinocerebellar ataxia.

Embodiment 114

The compound of embodiment 113, wherein the spinocerebellar ataxia is spinocerebellar ataxia 10.

Embodiment 115

The compound of any of embodiments 1-114, wherein the compound is a mutant selective compound.

Embodiment 116

The compound of embodiment 115, wherein the compound is capable of reducing the activity or amount of an expanded repeat-containing RNA at least ten fold more than it reduces the activity or amount of a corresponding wild type RNA.

Embodiment 117

The compound of embodiment 115 or 116, wherein the compound is capable of reducing the activity or amount of a protein encoded by an expanded repeat-containing RNA at least ten fold more than it reduces the activity or amount of a corresponding wild type protein.

Embodiment 118

The compound of embodiment 115, wherein the compound is capable of reducing the activity or amount of an expanded repeat-containing RNA at least five fold more than it reduces the activity or amount of a corresponding wild type RNA.

Embodiment 119

The compound of embodiment 115 or 116, wherein the compound is capable of reducing the activity or amount of a protein encoded by an expanded repeat-containing RNA at least five fold more than it reduces the activity or amount of a corresponding wild type protein.

Embodiment 120

The compound of embodiment 115 or 116, wherein the compound is capable of distribution throughout the ipsilateral striatum, contralateral cortex, contralateral striatum, thalamus, cerebellum, and brainstem.

Embodiment 121

The compound of embodiment 115 or 116, wherein a single dose of the compound is capable of reducing the activity or amount of mutant HTT expression for up to 5 days.

Embodiment 122

The compound of embodiment 115 or 116, wherein a single dose of the compound is capable of reducing the activity or amount of mutant HTT expression for up to 8 days.

Embodiment 123

The compound of any of 1-122, wherein the oligonucleotide comprises at least one modified nucleobase.

Embodiment 124

A method of selectively reducing the activity or amount of an expanded repeat-containing RNA in a cell, comprising contacting a cell having an expanded repeat-containing RNA with at least one compound of any of embodiments 1 to 123; and thereby selectively reducing the activity or amount of the expanded repeat-containing RNA in the cell.

Embodiment 125

The method of embodiment 124, wherein the amount or activity of the expanded repeat-containing RNA is reduced at least ten-fold more than that of a corresponding wild-type RNA.

Embodiment 126

The method of embodiment 123 or 124, wherein the cell is in vitro.

Embodiment 127

The method of embodiment 123 or 124, wherein the cell is in an animal.

Embodiment 128

A method of selectively reducing the amount or activity of a protein encoded by an expanded repeat-containing RNA in a cell, comprising contacting a cell having an expanded repeat-containing RNA with at least one compound of any of embodiments 1 to 123; and thereby selectively reducing the activity or amount of the protein encoded by the expanded repeat-containing RNA in the cell.

Embodiment 129

The method of embodiment 128, wherein the amount or activity of the protein encoded by the expanded repeat-containing RNA is reduced at least ten-fold more than that of a corresponding wild-type protein.

Embodiment 130

The method of embodiment 128 or 129, wherein the cell is in vitro.

Embodiment 131

The method of embodiment 128 or 129, wherein the cell is in an animal.

Embodiment 132

A pharmaceutical composition comprising at least one compound of any of embodiments 1-122 and a pharmaceutical carrier or diluents.

Embodiment 133

A method of treating a patient having a disease associated with an expanded repeat-containing RNA comprising administering to the patient the pharmaceutical composition of embodiment 132.

Embodiment 134

The method of embodiment 133, wherein the disease is selected from among: ataxin 3, atrophin 1, fragile X syndrome, Friedrich's ataxia, Huntington's disease, Huntington's disease-like 2, myotonic dystrophy, spinal and bulbar muscular atrophy, and spinocerebellar ataxia.

Embodiment 135

The method of embodiment 134, wherein the disease is Huntington's disease.

Embodiment 136

The method of embodiment 134, wherein the disease is myotonic dystrophy.

Embodiment 137

The method of embodiment 134, wherein the disease is spinocerebellar ataxia.

Embodiment 138

The method of any of embodiments 133-137, wherein the pharmaceutical composition is administered by injection.

Embodiment 139

The method of any of embodiments 133-137, wherein the pharmaceutical composition is adminstered into the central nervous system.

Embodiment 140

The method of any of embodiments 133-137, wherein the pharmaceutical composition is adminstered into the cerebrospinal fluid.

Embodiment 141

The method of any of embodiments 133-137, wherein the pharmaceutical composition is adminstered by intracerebroventricular administration.

Embodiment 142

The method of any of embodiments 133-137, wherein the pharmaceutical composition is administered intrathecally.

Embodiment 143

The method of any of embodiments 133-137, wherein the pharmaceutical composition is administered into the brain.

Embodiment 144

The method of any of embodiments 133-143, wherein the administration comprises a bolus injection.

Embodiment 145

The method of any of embodiments 133-143, wherein the administration comprises an infusion.

Embodiment 146

The method of embodiment 145, wherein the administration comprises an infusion by infusion pump.

BRIEF DESCRIPTION OF THE DRAWINGS

FIGS. 9a-f shows Western analysis of HTT protein expression of several CAG-repeat-containing genes in various brain tissues of Q150/Q7 mouse after modified ssRNA 537775 treatment

DETAILED DESCRIPTION

Figure 1:
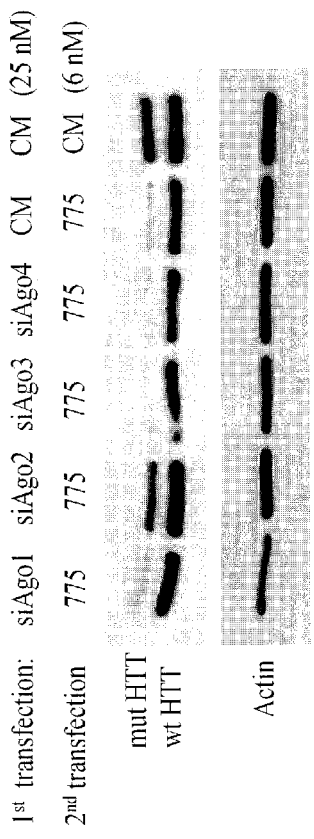
FIG. 1 shows the effects of reducing cellular Argonaute levels on inhibition of HTT expression by ISIS 537775.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

A. Definitions

Unless specific definitions are provided, the nomenclature used in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Certain such techniques and procedures may be found for example in "Carbohydrate Modifications in Antisense Research" Edited by Sangvi and Cook, American Chemical Society, Washington D.C., 1994; "Remington's Pharmaceutical Sciences," Mack Publishing Co., Easton, Pa., 21$^{st}$ edition, 2005; and "Antisense Drug Technology, Principles, Strategies, and Applications" Edited by Stanley T. Crooke, CRC Press, Boca Raton, Fla.; and Sambrook et al., "Molecular Cloning, A laboratory Manual," 2$^{nd}$ Edition, Cold Spring Harbor Laboratory Press, 1989, which are hereby incorporated by reference for any purpose. Where permitted, all patents, applications, published applications and other publications and other data referred to throughout in the disclosure are incorporated by reference herein in their entirety.

Unless otherwise indicated, the following terms have the following meanings:

As used herein, "nucleoside" means a compound comprising a nucleobase moiety and a sugar moiety. Nucleosides include, but are not limited to, naturally occurring nucleosides (as found in DNA and RNA) and modified nucleosides. Nucleosides may be linked to a phosphate moiety.

As used herein, "chemical modification" means a chemical difference in a compound when compared to a naturally occurring counterpart. Chemical modifications of oligonucleotides include nucleoside modifications (including sugar moiety modifications and nucleobase modifications) and internucleoside linkage modifications. In reference to an oligonucleotide, chemical modification does not include differences only in nucleobase sequence.

As used herein, "furanosyl" means a structure comprising a 5-membered ring comprising four carbon atoms and one oxygen atom.

As used herein, "naturally occurring sugar moiety" means a ribofuranosyl as found in naturally occurring RNA or a deoxyribofuranosyl as found in naturally occurring DNA.

As used herein, "sugar moiety" means a naturally occurring sugar moiety or a modified sugar moiety of a nucleoside.

As used herein, "modified sugar moiety" means a substituted sugar moiety or a sugar surrogate.

As used herein, "substituted sugar moiety" means a furanosyl that is not a naturally occurring sugar moiety. Substituted sugar moieties include, but are not limited to furanosyls comprising substituents at the 2'-position, the 3'-position, the 5'-position and/or the 4'-position. Certain substituted sugar moieties are bicyclic sugar moieties.

As used herein, "2'-substituted sugar moiety" means a furanosyl comprising a substituent at the 2'-position other than H or OH. Unless otherwise indicated, a 2'-substituted sugar moiety is not a bicyclic sugar moiety (i.e., the 2'-substituent of a 2'-substituted sugar moiety does not form a bridge to another atom of the furanosyl ring.

As used herein, "MOE" means —OCH$_2$CH$_2$OCH$_3$.

As used herein, "2'-F nucleoside" refers to a nucleoside comprising a sugar comprising fluoroine at the 2' position. Unless otherwise indicated, the fluorine in a 2'-F nucleoside is in the ribo position (replacing the OH of a natural ribose).

As used herein, "2'-F ANA" refers to a 2'-F substituted nucleoside, wherein the fluoro group is in the arabino position.

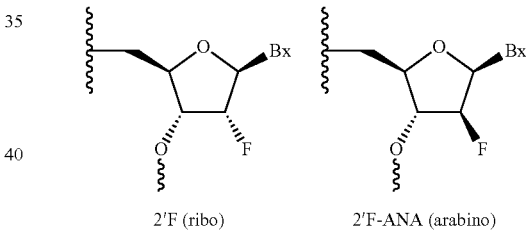

2'F (ribo)    2'F-ANA (arabino)

As used herein the term "sugar surrogate" means a structure that does not comprise a furanosyl and that is capable of replacing the naturally occurring sugar moiety of a nucleoside, such that the resulting nucleoside sub-units are capable of linking together and/or linking to other nucleosides to form an oligomeric compound which is capable of hybridizing to a complementary oligomeric compound. Such structures include rings comprising a different number of atoms than furanosyl (e.g., 4, 6, or 7-membered rings); replacement of the oxygen of a furanosyl with a non-oxygen atom (e.g., carbon, sulfur, or nitrogen); or both a change in the number of atoms and a replacement of the oxygen. Such structures may also comprise substitutions corresponding to those described for substituted sugar moieties (e.g., 6-membered carbocyclic bicyclic sugar surrogates optionally comprising additional substituents). Sugar surrogates also include more complex sugar replacements (e.g., the non-ring systems of peptide nucleic acid). Sugar surrogates include without limitation morpholinos, cyclohexenyls and cyclohexitols.

As used herein, "bicyclic sugar moiety" means a modified sugar moiety comprising a 4 to 7 membered ring (including but not limited to a furanosyl) comprising a bridge connecting two atoms of the 4 to 7 membered ring to form a second ring, resulting in a bicyclic structure. In certain embodiments, the 4 to 7 membered ring is a sugar ring. In certain embodiments the 4 to 7 membered ring is a furanosyl. In certain such embodiments, the bridge connects the 2'-carbon and the 4'-carbon of the furanosyl.

As used herein, "nucleotide" means a nucleoside further comprising a phosphate linking group. As used herein, "linked nucleosides" may or may not be linked by phosphate linkages and thus includes, but is not limited to "linked nucleotides." As used herein, "linked nucleosides" are nucleosides that are connected in a continuous sequence (i.e. no additional nucleosides are present between those that are linked).

As used herein, "nucleobase" means a group of atoms that can be linked to a sugar moiety to create a nucleoside that is capable of incorporation into an oligonucleotide, and wherein the group of atoms is capable of bonding with a complementary naturally occurring nucleobase of another oligonucleotide or nucleic acid. Nucleobases may be naturally occurring or may be modified.

As used herein the terms, "unmodified nucleobase" or "naturally occurring nucleobase" means the naturally occurring heterocyclic nucleobases of RNA or DNA: the purine bases adenine (A) and guanine (G), and the pyrimidine bases thymine (T), cytosine (C) (including 5-methyl C), and uracil (U).

As used herein, "modified nucleobase" means any nucleobase that is not a naturally occurring nucleobase.

As used herein, "modified nucleoside" means a nucleoside comprising at least one chemical modification compared to naturally occurring RNA or DNA nucleosides. Modified nucleosides comprise a modified sugar moiety and/or a modified nucleobase.

As used herein, "bicyclic nucleoside" or "BNA" means a nucleoside comprising a bicyclic sugar moiety.

As used herein, "constrained ethyl nucleoside" or "cEt" means a nucleoside comprising a bicyclic sugar moiety comprising a 4'-CH(CH$_3$)—O-2'bridge.

As used herein, "locked nucleic acid nucleoside" or "LNA" means a nucleoside comprising a bicyclic sugar moiety comprising a 4'-CH$_2$—O-2'bridge.

As used herein, "2'-substituted nucleoside" means a nucleoside comprising a substituent at the 2'-position other than H or OH. Unless otherwise indicated, a 2'-substituted nucleoside is not a bicyclic nucleoside.

As used herein, "2'-deoxynucleoside" means a nucleoside comprising 2'-H furanosyl sugar moiety, as found in naturally occurring deoxyribonucleosides (DNA). In certain embodiments, a 2'-deoxynucleoside may comprise a modified nucleobase or may comprise an RNA nucleobase (e.g., uracil).

As used herein, "RNA-like nucleoside" means a modified nucleoside that adopts a northern configuration and functions like RNA when incorporated into an oligonucleotide. RNA-like nucleosides include, but are not limited to 2'-endo furanosyl nucleosides and RNA surrogates.

As used herein, "2'-endo-furanosyl nucleoside" means an RNA-like nucleoside that comprises a substituted sugar moiety that has a 2'-endo conformation. 2'-endo-furanosyl nucleosides include, but are not limited to: 2'-MOE, 2'-F, 2'-OMe, LNA, ENA, and cEt nucleosides.

As used herein, "RNA-surrogate nucleoside" means an RNA-like nucleoside that does not comprise a furanosyl. RNA-surrogate nucleosides include, but are not limited to hexitols and cyclopentanes.

As used herein, "phosphorous moiety" refers to a to monovalent P$^V$ phosphorus radical group. In certain embodiments, a phosphorus moiety is selected from: a phosphate, phosphonate, alkylphosphonate, aminoalkyl phosphonate, phosphorothioate, phosphoramidite, alkylphosphonothioate, phosphorodithioate, thiophosphoramidate, phosphotriester and the like. In certain embodiments, modified phosphorous moieties have the following structural formula:

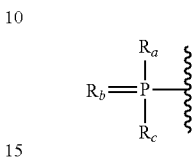

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino; and $R_b$ is O or S.

The term "phosphate moiety" as used herein, refers to a terminal phosphate group that includes unmodified phosphates (—O—P(=O)(OH)OH) as well as modified phosphates. Modified phosphates include but are not limited to phosphates in which one or more of the O and OH groups is replaced with H, O, S, N(R) or alkyl where R is H, an amino protecting group or unsubstituted or substituted alkyl.

As used herein, "phosphate stabilizing modification" refers to a modification that results in stabilization of a 5'-phosphate moiety of the 5'-terminal nucleoside of an oligonucleotide, relative to the stability of an unmodified 5'-phosphate of an unmodified nucleoside under biologic conditions. Such stabilization of a 5'-phophate group includes but is not limited to resistance to removal by phosphatases. Phosphate stabilizing modifications include, but are not limited to, modification of one or more of the atoms that binds directly to the phosphorus atom, modification of one or more atoms that link the phosphorus to the 5'-carbon of the nucleoside, and modifications at one or more other positions of the nucleoside that result in stabilization of the phosphate. In certain embodiments, a phosphate stabilizing modification comprises a carbon linking the phosphorous atom to the 5'-carbon of the sugar. Phosphate moieties that are stabilized by one or more phosphate stabilizing modification are referred to herein as "stabilized phosphate moieties."

As used herein, "oligonucleotide" means a compound comprising a plurality of linked nucleosides. In certain embodiments, an oligonucleotide comprises one or more unmodified ribonucleosides (RNA) and/or unmodified deoxyribonucleosides (DNA) and/or one or more modified nucleosides.

As used herein "oligonucleoside" means an oligonucleotide in which none of the internucleoside linkages contains a phosphorus atom. As used herein, oligonucleotides include oligonucleosides.

As used herein, "modified oligonucleotide" means an oligonucleotide comprising at least one modified nucleoside and/or at least one modified internucleoside linkage.

As used herein "internucleoside linkage" means a covalent linkage between adjacent nucleosides in an oligonucleotide.

As used herein "naturally occurring internucleoside linkage" means a 3' to 5' phosphodiester linkage.

As used herein, "modified internucleoside linkage" means any internucleoside linkage other than a naturally occurring internucleoside linkage.

As used herein, "oligomeric compound" means a polymeric structure comprising two or more sub-structures. In certain embodiments, an oligomeric compound comprises an oligonucleotide. In certain embodiments, an oligomeric compound comprises one or more conjugate groups and/or terminal groups. In certain embodiments, an oligomeric compound consists of an oligonucleotide. Oligomeric compounds also include naturally occurring nucleic acids.

As used herein, "terminal group" means one or more atom attached to either, or both, the 3' end or the 5' end of an oligonucleotide. In certain embodiments a terminal group is a conjugate group. In certain embodiments, a terminal group comprises one or more terminal group nucleosides.

As used herein, "conjugate" means an atom or group of atoms bound to an oligonucleotide or oligomeric compound. In general, conjugate groups modify one or more properties of the compound to which they are attached, including, but not limited to pharmacodynamic, pharmacokinetic, binding, absorption, cellular distribution, cellular uptake, charge and/or clearance properties.

As used herein, "conjugate linking group" means any atom or group of atoms used to attach a conjugate to an oligonucleotide or oligomeric compound.

As used herein, "single-stranded" means an oligomeric compound that is not hybridized to its complement and which lacks sufficient self-complementarity to form a stable self-duplex.

As used herein, "antisense compound" means a compound comprising or consisting of an oligonucleotide at least a portion of which is complementary to a target nucleic acid to which it is capable of hybridizing, resulting in at least one antisense activity.

As used herein, "antisense activity" means any detectable and/or measurable change attributable to the hybridization of an antisense compound to its target nucleic acid. In certain embodiments, antisense activity is a reduction of a gain-of-function of an expanded repeat-containing nucleic acid.

As used herein, "detecting" or "measuring" means that a test or assay for detecting or measuring is performed. Such detection and/or measuring may result in a value of zero. Thus, if a test for detection or measuring results in a finding of no activity (activity of zero), the step of detecting or measuring the activity has nevertheless been performed.

As used herein, "detectable and/or measureable activity" means a statistically significant activity that is not zero.

As used herein, "essentially unchanged" means little or no change in a particular parameter, particularly relative to another parameter which changes much more. In certain embodiments, a parameter is essentially unchanged when it changes less than 5%. In certain embodiments, a parameter is essentially unchanged if it changes less than two-fold while another parameter changes at least ten-fold. For example, in certain embodiments, an antisense activity is a change in the amount of a target nucleic acid. In certain such embodiments, the amount of a non-target nucleic acid is essentially unchanged if it changes much less than the target nucleic acid does, but the change need not be zero.

As used herein, "expression" means the process by which a gene ultimately results in a protein. Expression includes, but is not limited to, transcription, post-transcriptional modification (e.g., splicing, polyadenlyation, addition of 5'-cap), and translation.

As used herein, "target nucleic acid" means a nucleic acid molecule to which an antisense compound hybridizes.

As used herein, "targeting" or "targeted to" means the association of an antisense compound to a particular target nucleic acid molecule or a particular region of a target nucleic acid molecule. An antisense compound targets a target nucleic acid if it is sufficiently complementary to the target nucleic acid to allow hybridization under physiological conditions.

As used herein, the term "expanded repeat-containing RNA" means a mutant RNA molecule having a nucleobase sequence that includes a repeat region consisting essentially of repeating units of 3-5 nucleobases that repeat at least 10 times in the repeating region, and wherein the presence or length of the repeat region affects the normal processing, function, or activity of the RNA or corresponding protein.

As used herein, the term "corresponding wild type RNA" means the non-mutant version of the expanded repeat-containing RNA having normal function and activity. Typically, corresponding wild type RNA molecules comprise a repeat region which is shorter than that of an expanded repeat-containing RNA.

As used herein, "selectivity" refers to the ability of an antisense compound to exert an antisense activity on a target nucleic acid to a greater extent than on a non-target nucleic acid.

As used herein, "mutant selective" refers to a compound that has a greater effect on a mutant nucleic acid than on the corresponding wild-type nucleic acid. In certain embodiments, the effect of a mutant selective compound on the mutant nucleic acid is 2, 3, 4, 5, 6, 7, 8, 9, 10, 15, 20, 25, 30, 35, 40, 50, 100 or more than 100 times greater than the effect of the mutant selective compound on the corresponding wild-type nucleic acid. In certain embodiments, such selectivity results from greater affinity of the mutant selective compound for the mutant nucleic acid than for the corresponding wild type nucleic acid. In certain embodiments, selectivity results from a difference in the structure of the mutant compared to the wild-type nucleic acid. In certain embodiments, selectivity results from differences in processing or sub-cellular distribution of the mutant and wild-type nucleic acids. In certain embodiments, some selectivity may be attributable to the presence of additional target sites in a mutant nucleic acid compared to the wild-type nucleic acid. For example, in certain embodiments, a target mutant allele comprises an expanded repeat region comprising more repeats than the wild-type allele. Thus, the wild-type allele has fewer sites available for hybridization of an antisense compound targeting the repeat region. In certain embodiments, a mutant selective compound has selectivity greater than the selectivity predicted by the increased number of target sites. In certain embodiments, the ratio of inhibition of a mutant allele to a wild type allele is equal to or greater than the ratio of the number of repeats in the mutant allele to the wild type allele. In certain embodiments, the ratio of inhibition of a mutant allele to a wild type allele is greater than the ratio of the number of repeats in the mutant allele to the wild type allele.

As used herein, "gain-of-function activity" means a biological activity attributed to an expanded repeat-containing RNA. For example, an expanded repeat-containing RNA may gain the ability to sequester ribonuclear proteins and impair the normal action of RNA processing in the nucleus (see Cooper, T. (2009) Cell 136, 777-793; O'Rourke, J R (2009) J. Biol. Chem. 284 (12), 7419-7423).

As used herein, "nucleobase complementarity" or "complementarity" when in reference to nucleobases means a nucleobase that is capable of base pairing with another nucleobase. For example, in DNA, adenine (A) is complementary to thymine (T). For example, in RNA, adenine (A) is complementary to uracil (U). In certain embodiments, complementary nucleobase means a nucleobase of an antisense compound that is capable of base pairing with a nucleobase of its target nucleic acid. For example, if a nucleobase at a certain position of an antisense compound is capable of hydrogen bonding with a nucleobase at a certain position of a target nucleic acid, then the position of hydrogen bonding between the oligonucleotide and the target nucleic acid is considered to be complementary at that nucleobase pair. Nucleobases comprising certain modifications may maintain the ability to pair with a counterpart nucleobase and thus, are still capable of nucleobase complementarity.

As used herein, "non-complementary" in reference to nucleobases means a pair of nucleobases that do not form hydrogen bonds with one another.

As used herein, "complementary" in reference to oligomeric compounds (e.g., linked nucleosides, oligonucleotides, or nucleic acids) means the capacity of such oligomeric compounds or regions thereof to hybridize to another oligomeric compound or region thereof through nucleobase complementarity. Complementary oligomeric compounds need not have nucleobase complementarity at each nucleoside. Rather, some mismatches are tolerated. In certain embodiments, complementary oligomeric compounds or regions are complementary at 70% of the nucleobases (70% complementary). In certain embodiments, complementary oligomeric compounds or regions are 80% complementary. In certain embodiments, complementary oligomeric compounds or regions are 90% complementary. In certain embodiments, complementary oligomeric compounds or regions are 95% complementary. In certain embodiments, complementary oligomeric compounds or regions are 100% complementary.

As used herein, "mismatch" means a nucleobase of a first oligomeric compound that is not capable of pairing with a nucleobase at a corresponding position of a second oligomeric compound, when the first and second oligomeric compound are aligned. Either or both of the first and second oligomeric compounds may be oligonucleotides.

As used herein, "hybridization" means the pairing of complementary oligomeric compounds (e.g., an antisense compound and its target nucleic acid). While not limited to a particular mechanism, the most common mechanism of pairing involves hydrogen bonding, which may be Watson-Crick, Hoogsteen or reversed Hoogsteen hydrogen bonding, between complementary nucleobases.

As used herein, "specifically hybridizes" means the ability of an oligomeric compound to hybridize to one nucleic acid site with greater affinity than it hybridizes to another nucleic acid site.

As used herein, "fully complementary" in reference to an oligonucleotide or portion thereof means that each nucleobase of the oligonucleotide or portion thereof is capable of pairing with a nucleobase of a complementary nucleic acid or contiguous portion thereof. Thus, a fully complementary region comprises no mismatches or unhybridized nucleobases in either strand.

As used herein, "percent complementarity" means the percentage of nucleobases of an oligomeric compound that are complementary to an equal-length portion of a target nucleic acid. Percent complementarity is calculated by dividing the number of nucleobases of the oligomeric compound that are complementary to nucleobases at corresponding positions in the target nucleic acid by the total length of the oligomeric compound.

As used herein, "percent identity" means the number of nucleobases in a first nucleic acid that are the same type (independent of chemical modification) as nucleobases at corresponding positions in a second nucleic acid, divided by the total number of nucleobases in the first nucleic acid.

As used herein, "modulation" means a change of amount or quality of a molecule, function, or activity when compared to the amount or quality of a molecule, function, or activity prior to modulation. For example, modulation includes the change, either an increase (stimulation or induction) or a decrease (inhibition or reduction) in gene expression. As a further example, modulation of expression can include a change in splice site selection of pre-mRNA processing, resulting in a change in the absolute or relative amount of a particular splice-variant compared to the amount in the absence of modulation.

As used herein, "motif" means a pattern of chemical modifications in an oligonucleotide or a region thereof. Motifs may be defined by modifications at certain nucleosides and/or at certain linking groups of an oligonucleotide.

As used herein, "nucleoside motif" means a pattern of nucleoside modifications in an oligonucleotide or a region thereof. The linkages of such an oligonucleotide may be modified or unmodified. Unless otherwise indicated, motifs herein describing only nucleosides are intended to be nucleoside motifs. Thus, in such instances, the linkages are not limited.

As used herein, "sugar motif" means a pattern of sugar modifications in an oligonucleotide or a region thereof.

As used herein, "linkage motif" means a pattern of linkage modifications in an oligonucleotide or region thereof. The nucleosides of such an oligonucleotide may be modified or unmodified. Unless otherwise indicated, motifs herein describing only linkages are intended to be linkage motifs. Thus, in such instances, the nucleosides are not limited.

As used herein, "nucleobase modification motif" means a pattern of modifications to nucleobases along an oligonucleotide. Unless otherwise indicated, a nucleobase modification motif is independent of the nucleobase sequence.

As used herein, "sequence motif" means a pattern of nucleobases arranged along an oligonucleotide or portion thereof. Unless otherwise indicated, a sequence motif is independent of chemical modifications and thus may have any combination of chemical modifications, including no chemical modifications.

As used herein, "type of modification" in reference to a nucleoside or a nucleoside of a "type" means the chemical modification of a nucleoside and includes modified and unmodified nucleosides. Accordingly, unless otherwise indicated, a "nucleoside having a modification of a first type" may be an unmodified nucleoside.

As used herein, "differently modified" mean chemical modifications or chemical substituents that are different from one another, including absence of modifications. Thus, for example, a MOE nucleoside and an unmodified DNA nucleoside are "differently modified," even though the DNA nucleoside is unmodified. Likewise, DNA and RNA are "differently modified," even though both are naturally-occurring unmodified nucleosides. Nucleosides that are the same but for comprising different nucleobases are not differently modified. For example, a nucleoside comprising a 2'-OMe modified sugar and an unmodified adenine nucleobase and a nucleoside comprising a 2'-OMe modified sugar and an unmodified thymine nucleobase are not differently modified.

As used herein, "the same type of modifications" refers to modifications that are the same as one another, including absence of modifications. Thus, for example, two unmodified DNA nucleosides have "the same type of modification," even though the DNA nucleoside is unmodified. Such nucleosides having the same type modification may comprise different nucleobases.

As used herein, "separate regions" means portions of an oligonucleotide wherein the chemical modifications or the motif of chemical modifications of any neighboring portions include at least one difference to allow the separate regions to be distinguished from one another.

As used herein, "pharmaceutically acceptable carrier or diluent" means any substance suitable for use in administering to an animal. In certain embodiments, a pharmaceutically acceptable carrier or diluent is sterile saline. In certain embodiments, such sterile saline is pharmaceutical grade saline.

As used herein, "substituent" and "substituent group," means an atom or group that replaces the atom or group of a named parent compound. For example a substituent of a modified nucleoside is any atom or group that differs from the atom or group found in a naturally occurring nucleoside (e.g., a modified 2'-substituent is any atom or group at the 2'-position of a nucleoside other than H or OH). Substituent groups can be protected or unprotected. In certain embodiments, compounds of the present invention have substituents at one or at more than one position of the parent compound. Substituents may also be further substituted with other substituent groups and may be attached directly or via a linking group such as an alkyl or hydrocarbyl group to a parent compound.

Likewise, as used herein, "substituent" in reference to a chemical functional group means an atom or group of atoms that differs from the atom or a group of atoms normally present in the named functional group. In certain embodiments, a substituent replaces a hydrogen atom of the functional group (e.g., in certain embodiments, the substituent of a substituted methyl group is an atom or group other than hydrogen which replaces one of the hydrogen atoms of an unsubstituted methyl group). Unless otherwise indicated, groups amenable for use as substituents include without limitation, halogen, hydroxyl, alkyl, alkenyl, alkynyl, acyl (—C(O)$R_{aa}$), carboxyl (—C(O)O—$R_{aa}$), aliphatic groups, alicyclic groups, alkoxy, substituted oxy (—O—$R_{aa}$), aryl, aralkyl, heterocyclic radical, heteroaryl, heteroarylalkyl, amino (—N($R_{bb}$)($R_{cc}$)), imino(=$NR_{bb}$), amido (—C(O)N($R_{bb}$)($R_{cc}$) or —N($R_{bb}$)C(O)$R_{aa}$), azido (—$N_3$), nitro (—$NO_2$), cyano (—CN), carbamido (—OC(O)N($R_{bb}$)($R_{cc}$) or —N($R_{bb}$)C(O)O$R_{aa}$), ureido (—N($R_{bb}$)C(O)N($R_{bb}$)($R_{cc}$)), thioureido (—N($R_{bb}$)C(S)N($R_{bb}$)—($R_{cc}$)), guanidinyl (—N($R_{bb}$)C(=$NR_{bb}$)N($R_{bb}$)($R_{cc}$)), amidinyl (—C(=$NR_{bb}$)N($R_{bb}$)($R_{cc}$) or —N($R_{bb}$)C(—$NR_{bb}$)($R_{aa}$)), thiol (—S$R_{bb}$), sulfinyl (—S(O)$R_{bb}$), sulfonyl (—S(O)$_2 R_{bb}$) and sulfonamidyl (—S(O)$_2$N($R_{bb}$)($R_{cc}$) or —N($R_{bb}$)S—(O)$_2$ $R_{bb}$). Wherein each $R_{aa}$, $R_{bb}$ and $R_{cc}$ is, independently, H, an optionally linked chemical functional group or a further substituent group with a preferred list including without limitation, alkyl, alkenyl, alkynyl, aliphatic, alkoxy, acyl, aryl, aralkyl, heteroaryl, alicyclic, heterocyclic and heteroarylalkyl. Selected substituents within the compounds described herein are present to a recursive degree.

As used herein, "alkyl," as used herein, means a saturated straight or branched hydrocarbon radical containing up to twenty four carbon atoms. Examples of alkyl groups include without limitation, methyl, ethyl, propyl, butyl, isopropyl, n-hexyl, octyl, decyl, dodecyl and the like. Alkyl groups typically include from 1 to about 24 carbon atoms, more typically from 1 to about 12 carbon atoms ($C_1$-$C_{12}$ alkyl) with from 1 to about 6 carbon atoms being more preferred.

As used herein, "alkenyl," means a straight or branched hydrocarbon chain radical containing up to twenty four carbon atoms and having at least one carbon-carbon double bond. Examples of alkenyl groups include without limitation, ethenyl, propenyl, butenyl, 1-methyl-2-buten-1-yl, dienes such as 1,3-butadiene and the like. Alkenyl groups typically include from 2 to about 24 carbon atoms, more typically from 2 to about 12 carbon atoms with from 2 to about 6 carbon atoms being more preferred. Alkenyl groups as used herein may optionally include one or more further substituent groups.

As used herein, "alkynyl," means a straight or branched hydrocarbon radical containing up to twenty four carbon atoms and having at least one carbon-carbon triple bond. Examples of alkynyl groups include, without limitation, ethynyl, 1-propynyl, 1-butynyl, and the like. Alkynyl groups typically include from 2 to about 24 carbon atoms, more typically from 2 to about 12 carbon atoms with from 2 to about 6 carbon atoms being more preferred. Alkynyl groups as used herein may optionally include one or more further substituent groups.

As used herein, "acyl," means a radical formed by removal of a hydroxyl group from an organic acid and has the general Formula —C(O)—X where X is typically aliphatic, alicyclic or aromatic. Examples include aliphatic carbonyls, aromatic carbonyls, aliphatic sulfonyls, aromatic sulfinyls, aliphatic sulfinyls, aromatic phosphates, aliphatic phosphates and the like. Acyl groups as used herein may optionally include further substituent groups.

As used herein, "alicyclic" means a cyclic ring system wherein the ring is aliphatic. The ring system can comprise one or more rings wherein at least one ring is aliphatic. Preferred alicyclics include rings having from about 5 to about 9 carbon atoms in the ring. Alicyclic as used herein may optionally include further substituent groups.

As used herein, "aliphatic" means a straight or branched hydrocarbon radical containing up to twenty four carbon atoms wherein the saturation between any two carbon atoms is a single, double or triple bond. An aliphatic group preferably contains from 1 to about 24 carbon atoms, more typically from 1 to about 12 carbon atoms with from 1 to about 6 carbon atoms being more preferred. The straight or branched chain of an aliphatic group may be interrupted with one or more heteroatoms that include nitrogen, oxygen, sulfur and phosphorus. Such aliphatic groups interrupted by heteroatoms include without limitation, polyalkoxys, such as polyalkylene glycols, polyamines, and polyimines. Aliphatic groups as used herein may optionally include further substituent groups.

As used herein, "alkoxy" means a radical formed between an alkyl group and an oxygen atom wherein the oxygen atom is used to attach the alkoxy group to a parent molecule. Examples of alkoxy groups include without limitation, methoxy, ethoxy, propoxy, isopropoxy, n-butoxy, sec-butoxy, tert-butoxy, n-pentoxy, neopentoxy, n-hexoxy and the like. Alkoxy groups as used herein may optionally include further substituent groups.

As used herein, "aminoalkyl" means an amino substituted $C_1$-$C_{12}$ alkyl radical. The alkyl portion of the radical forms a covalent bond with a parent molecule. The amino group can be located at any position and the aminoalkyl group can be substituted with a further substituent group at the alkyl and/or amino portions.

As used herein, "aralkyl" and "arylalkyl" mean an aromatic group that is covalently linked to a $C_1$-$C_{12}$ alkyl radical. The alkyl radical portion of the resulting aralkyl (or arylalkyl) group forms a covalent bond with a parent molecule. Examples include without limitation, benzyl, phenethyl and the like. Aralkyl groups as used herein may optionally include further substituent groups attached to the alkyl, the aryl or both groups that form the radical group.

As used herein, "aryl" and "aromatic" mean a mono- or polycyclic carbocyclic ring system radicals having one or more aromatic rings. Examples of aryl groups include without limitation, phenyl, naphthyl, tetrahydronaphthyl, indanyl, idenyl and the like. Preferred aryl ring systems have from about 5 to about 20 carbon atoms in one or more rings. Aryl groups as used herein may optionally include further substituent groups.

As used herein, "halo" and "halogen," mean an atom selected from fluorine, chlorine, bromine and iodine.

As used herein, "heteroaryl," and "heteroaromatic," mean a radical comprising a mono- or polycyclic aromatic ring, ring system or fused ring system wherein at least one of the rings is aromatic and includes one or more heteroatoms. Heteroaryl is also meant to include fused ring systems including systems where one or more of the fused rings contain no heteroatoms. Heteroaryl groups typically include one ring atom selected from sulfur, nitrogen or oxygen. Examples of heteroaryl groups include without limitation, pyridinyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, benzimidazolyl, benzooxazolyl, quinoxalinyl and the like. Heteroaryl radicals can be attached to a parent molecule directly or through a linking moiety such as an aliphatic group or hetero atom. Heteroaryl groups as used herein may optionally include further substituent groups.

As used herein, "parenteral administration," means administration through injection or infusion. Parenteral administration includes, but is not limited to, subcutaneous administration, intravenous administration, or intramuscular administration.

As used herein, "systemic administration" means administration to an area other than the intended locus of activity. Examples or systemic administration are subcutaneous administration and intravenous administration, and intraperitoneal administration.

As used herein, "subcutaneous administration" means administration just below the skin.

As used herein, "intravenous administration" means administration into a vein.

As used herein, "cerebrospinal fluid" or "CSF" means the fluid filling the space around the brain and spinal cord.

As used herein, "administration into the cerebrospinal fluid" means any administration that delivers a substance directly into the CSF.

As used herein, "intracerebroventricular" or "ICV" mean administration into the ventricular system of the brain.

As used herein, "intrathecal" or "IT" means administration into the CSF under the arachnoid membrane which covers the brain and spinal cord. IT injection is performed through the theca of the spinal cord into the subarachnoid space, where a pharmaceutical agent is injected into the sheath surrounding the spinal cord.

B. Certain Compounds

In certain embodiments, the present invention provides compounds useful for studying, diagnosing, and/or treating a disease or disorder associated with an expanded repeat-containing RNA. In certain embodiments, compounds of the present invention comprise an oligonucleotide and a conjugate and/or terminal group. In certain embodiments, compounds consist of an oligonucleotide.

In certain embodiments, an oligonucleotide of the present invention has a nucleobase sequence comprising a region that is complementary to a repeat region of an expanded repeat-containing RNA. In certain embodiments, such oligonucleotides comprise one or more modifications.

a. Certain 5'-Terminal Nucleosides

In certain embodiments, compounds of the present invention comprise oligonucleotides comprising a stabilized phosphate moiety at the 5'-terminus. In certain such embodiments, the phosphorus atom of the stabilized phosphate moiety is attached to the 5'-terminal nucleoside through a phosphorus-carbon bond. In certain embodiments, the carbon of that phosphorus-carbon bond is in turn bound to the 5'-position of the nucleoside.

In certain embodiments, the oligonucleotide comprises a 5'-stabilized phosphate moiety having the following formula:

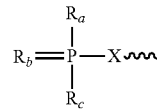

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino;

$R_b$ is O or S;

X is substituted or unsubstituted C; and wherein X is attached to the 5'-terminal nucleoside. In certain embodiments, X is bound to an atom at the 5'-position of the 5'-terminal nucleoside. In certain such embodiments, the 5'-atom is a carbon and the bond between X and the 5'-carbon of the 5'-terminal nucleoside is a carbon-carbon single bond. In certain embodiments, it is a carbon-carbon double bond. In certain embodiments, it is a carbon-carbon triple bond. In certain embodiments, the 5'-carbon is substituted. In certain embodiments, X is substituted. In certain embodiments, X is unsubstituted.

In certain embodiments, the oligonucleotide comprises a 5'-stabilized phosphate moiety having the following formula:

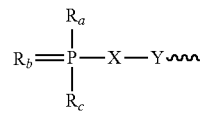

wherein:

$R_a$ and $R_c$ are each, independently, OH, SH, $C_1$-$C_6$ alkyl, substituted $C_1$-$C_6$ alkyl, $C_1$-$C_6$ alkoxy, substituted $C_1$-$C_6$ alkoxy, amino or substituted amino;

$R_b$ is O or S;

X is substituted or unsubstituted C;

Y is selected from C, S, and N. In certain embodiments, Y is substituted or unsubstituted C. The bond between X and Y may be a single-, double-, or triple-bond.

In certain such embodiments, Y is the 5'-atom of the 5'-terminal nucleoside.

In certain embodiments, such oligonucleotides comprise a 5'terminal nucleoside having Formula I:

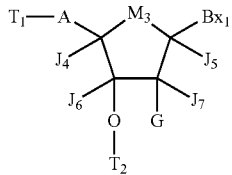

wherein:

T$_1$ is a phosphorus moiety;

T$_2$ is an internucleoside linking group linking the nucleoside of Formula I to the remainder of the oligonucleotide;

A has one of the formulas:

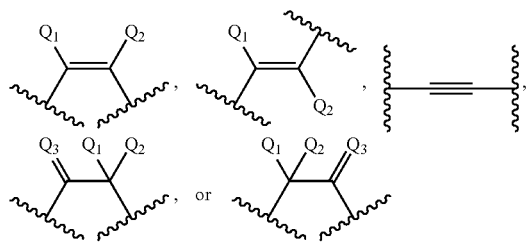

Q$_1$ and Q$_2$ are each, independently, H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_1$-C$_6$ alkoxy, substituted C$_1$-C$_6$ alkoxy or N(R$_3$)(R$_4$);

Q$_3$ is O, S, N(R$_5$) or C(R$_6$)(R$_7$);

each R$_3$, R$_4$ R$_5$, R$_6$ and R$_7$ is, independently, H, C$_1$-C$_6$ alkyl, substituted C$_1$-C$_6$ alkyl or C$_1$-C$_6$ alkoxy;

M$_3$ is O, S, NR$_{14}$, C(R$_{15}$)(R$_{16}$), C(R$_{15}$)(R$_{16}$)C(R$_{17}$)(R$_{18}$), C(R$_{15}$)=C(R$_{17}$), OC(R$_{15}$)(R$_{16}$) or OC(R$_{15}$)(Bx$_2$);

R$_{14}$ is H, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;

R$_{15}$, R$_{16}$, R$_{17}$ and R$_{18}$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;

one of Bx$_1$ and Bx$_2$ is a nucleobase and the other of Bx$_1$ and Bx$_2$, if present, is H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;

J$_4$, J$_5$, J$_6$ and J$_7$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;

or J$_4$ forms a bridge with either J$_5$ or J$_7$ wherein said bridge comprises from 1 to 3 linked biradical groups selected from O, S, NR$_{19}$, C(R$_{20}$)(R$_{21}$), C(R$_{20}$)=C(R$_{21}$), C[=C(R$_{20}$)(R$_{21}$)] and C(=O) and the other two of J$_5$, J$_6$ and J$_7$ are each, independently, H, halogen, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;

each R$_{19}$, R$_{20}$ and R$_{21}$ is, independently, H, C$_1$-C$_6$ alkyl, substituted C$_1$-C$_6$ alkyl, C$_1$-C$_6$ alkoxy, substituted C$_1$-C$_6$ alkoxy, C$_2$-C$_6$ alkenyl, substituted C$_2$-C$_6$ alkenyl, C$_2$-C$_6$ alkynyl or substituted C$_2$-C$_6$ alkynyl;

G is H, OH, halogen or O—[C(R$_8$)(R$_9$)]$_n$—[(C=O)$_m$—X$_1$]$_j$—Z, or a conjugate group;

each R$_8$ and R$_9$ is, independently, H, halogen, C$_1$-C$_6$ alkyl or substituted C$_1$-C$_6$ alkyl;

X$_1$ is O, S or N(E$_1$);

Z is H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl or N(E$_2$)(E$_3$);

E$_1$, E$_2$ and E$_3$ are each, independently, H, C$_1$-C$_6$ alkyl or substituted C$_1$-C$_6$ alkyl;

n is from 1 to about 6;

m is 0 or 1;

j is 0 or 1;

each substituted group comprises one or more optionally protected substituent groups independently selected from halogen, OJ$_1$, N(J$_1$)(J$_2$), =NJ$_1$, SJ$_1$, N$_3$, CN, OC(=X$_2$)J$_1$, OC(=X$_2$)N(J$_1$)(J$_2$) and C(=X$_2$)N(J$_1$)(J$_2$);

X$_2$ is O, S or NJ$_3$;

each J$_1$, J$_2$ and J$_3$ is, independently, H or C$_1$-C$_6$ alkyl; and when j is 1 then Z is other than halogen or N(E$_2$)(E$_3$).

In certain embodiments, oligonucleotides comprise a 5'-terminal nucleoside having Formula II:

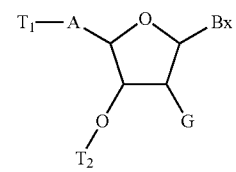

wherein:

Bx is a nucleobase;

T$_1$ is an phosphorus moiety;

T$_2$ is an internucleoside linking group linking the compound of Formula II to the remainder of the oligonucleotide;

A has one of the formulas:

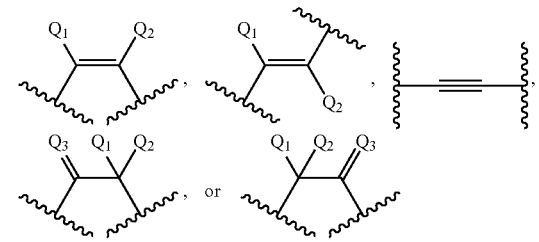

Q$_1$ and Q$_2$ are each, independently, H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl, C$_1$-C$_6$ alkoxy, substituted C$_1$-C$_6$ alkoxy or N(R$_3$)(R$_4$);

Q$_3$ is O, S, N(R$_5$) or C(R$_6$)(R$_7$);

each R$_3$, R$_4$ R$_5$, R$_6$ and R$_7$ is, independently, H, C$_1$-C$_6$ alkyl, substituted C$_1$-C$_6$ alkyl or C$_1$-C$_6$ alkoxy;

G is H, OH, halogen, O—[C(R$_8$)(R$_9$)]$_n$—[(C=O)$_m$—X]$_j$—Z or a conjugate group;

each R$_8$ and R$_9$ is, independently, H, halogen, C$_1$-C$_6$ alkyl or substituted C$_1$-C$_6$ alkyl;

X is O, S or N(E$_1$);

Z is H, halogen, C$_1$-C$_6$ alkyl, substituted C$_1$-C$_6$ alkyl, C$_2$-C$_6$ alkenyl, substituted C$_2$-C$_6$ alkenyl, C$_2$-C$_6$ alkynyl, substituted C$_2$-C$_6$ alkynyl or N(E$_2$)(E$_3$);

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, oligonucleotides comprise a 5'-terminal nucleoside having Formula III:

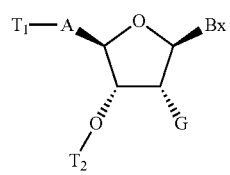

III wherein:

Bx is a nucleobase;

$T_1$ is a phosphorus moiety;

$T_2$ is an internucleoside linking group linking the compound of Formula III to the remainder of the oligonucleotide;

A has one of the formulas:

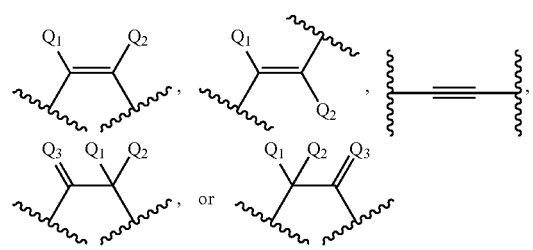

$Q_1$ and $Q_2$ are each, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, $C_1$-$C_6$ alkoxy, substituted $C_1$-$C_6$ alkoxy or $N(R_3)(R_4)$;

$Q_3$ is O, S, $N(R_5)$ or $C(R_6)(R_7)$;

each $R_3$, $R_4 R_5$, $R_6$ and $R_7$ is, independently, H, $C_1$-$C_6$ alkyl, substituted $C_1$-$C_6$ alkyl or $C_1$-$C_6$ alkoxy;

G is H, OH, halogen, O—$[C(R_8)(R_9)]_n[(C=O)_m—X]_j$—Z, or a conjugate group;

each $R_8$ and $R_9$ is, independently, H, halogen, $C_1$-$C_6$ alkyl or substituted $C_1$-$C_6$ alkyl;

X is O, S or $N(E_1)$;

Z is H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl or $N(E_2)(E_3)$;

$E_1$, $E_2$ and $E_3$ are each, independently, H, $C_1$-$C_6$ alkyl or substituted $C_1$-$C_6$ alkyl;

n is from 1 to about 6;

m is 0 or 1;

j is 0 or 1;

each substituted group comprises one or more optionally protected substituent groups independently selected from halogen, $OJ_1$, $N(J_1)(J_2)$, $=NJ_1$, $SJ_1$, $N_3$, CN, $OC(=L)J_1$, $OC(=L)N(J_1)(J_2)$ and $C(=L)N(J_1)(J_2)$;

L is O, S or $NJ_3$;

each $J_1$, $J_2$ and $J_3$ is, independently, H or $C_1$-$C_6$ alkyl; and when j is 1 then Z is other than halogen or $N(E_2)(E_3)$.

In certain embodiments, oligonucleotides comprise a 5'-terminal nucleoside having Formula IV:

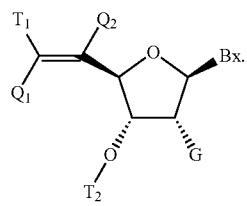

IV

In certain embodiments, oligonucleotide are provided comprising a compound having Formula IV wherein $Q_1$ and $Q_2$ are each H. In certain embodiments, oligonucleotide are provided comprising a compound having Formula IV wherein G is $O(CH_2)_2OCH_3$.

In certain embodiments, oligonucleotides comprise a 5'-terminal nucleoside having Formula V:

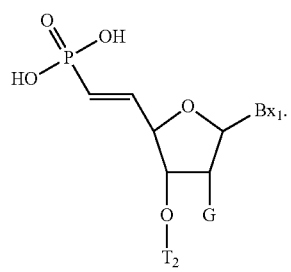

V

In certain embodiments, oligonucleotides comprise a nucleoside of Formula I, II, III, IV, or V. In certain such embodiments, the nucleoside of Formula I, II, III, IV, or V is at the 5'-terminus. In certain such embodiments, the remainder of the oligonucleotide comprises one or more modifications. Such modifications may include modified sugar moieties, modified nucleobases and/or modified internucleoside linkages. Certain such modifications which may be incorporated in an oligonucleotide comprising a nucleoside of Formula I, II, III, IV, or V at the 5'-terminus are known in the art.

b. Certain Sugar Moieties

In certain embodiments, compounds of the invention comprise one or more modified nucleosides comprising a modified sugar moiety. Such compounds comprising one or more sugar-modified nucleosides may have desirable properties, such as enhanced nuclease stability or increased binding affinity with a target nucleic acid relative to an oligonucleotide comprising only nucleosides comprising naturally occurring sugar moieties. In certain embodiments, modified sugar moieties are substituted sugar moieties. In certain embodiments, modified sugar moieties are sugar surrogates. Such sugar surrogates may comprise one or more substitutions corresponding to those of substituted sugar moieties.

In certain embodiments, modified sugar moieties are substituted sugar moieties comprising one or more non-bridging sugar substituent, including but not limited to substituents at the 2' and/or 5' positions. Examples of sugar substituents suitable for the 2'-position, include, but are not limited to: 2'-F, 2'-OCH$_3$ ("OMe" or "O-methyl"), and 2'-O(CH$_2$)$_2$OCH$_3$ ("MOE"). In certain embodiments, sugar substituents at the 2' position is selected from allyl, amino, azido, thio, O-allyl, O—C$_1$-C$_{10}$ alkyl, O—C$_1$-C$_{10}$ substituted alkyl; OCF$_3$, O(CH$_2$)$_2$SCH$_3$, O(CH$_2$)$_2$—O—N(Rm)(Rn), and O—CH$_2$—C(=O)—N(Rm)(Rn), where each Rm and Rn is, independently, H or substituted or unsubstituted C$_1$-C$_{10}$ alkyl. Examples of sugar substituents at the 5'-position, include, but are not limited to: 5'-methyl (R or S); 5'-vinyl, and 5'-methoxy. In certain embodiments, substituted sugars comprise more than one non-bridging sugar substituent, for example, T-F-5'-methyl sugar moieties (see, e.g., PCT International Application WO 2008/101157, for additional 5',2'-bis substituted sugar moieties and nucleosides).

Nucleosides comprising 2'-substituted sugar moieties are referred to as 2'-substituted nucleosides. In certain embodiments, a 2'-substituted nucleoside comprises a 2'-substituent group selected from halo, allyl, amino, azido, SH, CN, OCN, CF$_3$, OCF$_3$, O, S, or N(R$_m$)-alkyl; O, S, or N(R$_m$)-alkenyl; O, S or N(R$_m$)—alkynyl; O-alkylenyl-O-alkyl, alkynyl, alkaryl, aralkyl, O-alkaryl, O-aralkyl, O(CH$_2$)$_2$SCH$_3$, O(CH$_2$)$_2$—O—N(R$_m$)(R$_n$) or O—CH$_2$—C(=O)—N(R$_m$)(R$_n$), where each R$_m$ and R$_n$ is, independently, H, an amino protecting group or substituted or unsubstituted C$_1$-C$_{10}$ alkyl. These 2'-substituent groups can be further substituted with one or more substituent groups independently selected from hydroxyl, amino, alkoxy, carboxy, benzyl, phenyl, nitro (NO$_2$), thiol, thioalkoxy (S-alkyl), halogen, alkyl, aryl, alkenyl and alkynyl.

In certain embodiments, a 2'-substituted nucleoside comprises a 2'-substituent group selected from F, NH$_2$, N$_3$, OCF$_3$, O—CH$_3$, O(CH$_2$)$_3$NH$_2$, CH$_2$—CH=CH$_2$, O—CH$_2$—CH=CH$_2$, OCH$_2$CH$_2$OCH$_3$, O(CH$_2$)$_2$SCH$_3$, O—(CH$_2$)$_2$—O—N(R$_m$)(R$_n$), O(CH$_2$)$_2$O(CH$_2$)$_2$N(CH$_3$)$_2$, and N-substituted acetamide (O—CH$_2$—C(=O)—N(R$_m$)(R$_n$) where each R$_m$ and R$_n$ is, independently, H, an amino protecting group or substituted or unsubstituted C$_1$-C$_{10}$ alkyl.

In certain embodiments, a 2'-substituted nucleoside comprises a sugar moiety comprising a 2'-substituent group selected from F, OCF$_3$, O—CH$_3$, OCH$_2$CH$_2$OCH$_3$, O(CH$_2$)$_2$ SCH$_3$, O(CH$_2$)$_2$—O—N(CH$_3$)$_2$, —O(CH$_2$)$_2$O(CH$_2$)$_2$N(CH$_3$)$_2$, and O—CH$_2$—C(=O)—N(H)CH$_3$.

In certain embodiments, a 2'-substituted nucleoside comprises a sugar moiety comprising a 2'-substituent group selected from F, O—CH$_3$, and OCH$_2$CH$_2$OCH$_3$.

Certain modified sugar moieties comprise a bridging sugar substituent that forms a second ring resulting in a bicyclic sugar moiety. In certain such embodiments, the bicyclic sugar moiety comprises a bridge between the 4' and the 2' furanose ring atoms. Examples of such 4' to 2' sugar substituents, include, but are not limited to: —[C(R$_a$)(R$_b$)]$_n$—, —[C(R$_a$)(R$_b$)]$_n$—O—, —C(R$_a$R$_b$)—N(R)—O— or, —C(R$_a$R$_b$)—O—N(R)—; 4'- CH$_2$-2', 4'-(CH$_2$)$_2$-2', 4'-(CH$_2$)—O-2' (LNA); 4'-(CH$_2$)—S-2'; 4'-(CH$_2$)$_2$—O-2' (ENA); 4'-CH(CH$_3$)—O-2' (cEt) and 4'-CH(CH$_2$OCH$_3$)—O-2', and analogs thereof (see, e.g., U.S. Pat. No. 7,399,845, issued on Jul. 15, 2008; 4'-C(CH$_3$)(CH$_3$)—O-2' and analogs thereof, (see, e.g., WO2009/006478, published Jan. 8, 2009); 4'-CH$_2$—N(OCH$_3$)-2' and analogs thereof (see, e.g., WO2008/150729, published Dec. 11, 2008); 4'-CH$_2$—O—N(CH$_3$)-2' (see, e.g., US2004/0171570, published Sep. 2, 2004); 4'-CH$_2$—O—N(R)-2', and 4'-CH$_2$—N(R)—O-2'-, wherein each R is, independently, H, a protecting group, or C$_1$-C$_{12}$ alkyl; 4'-CH$_2$—N(R)—O-2', wherein R is H, C$_1$-C$_{12}$ alkyl, or a protecting group (see, U.S. Pat. No. 7,427,672, issued on Sep. 23, 2008); 4'-CH$_2$—C(H)(CH$_3$)-2' (see, e.g., Chattopadhyaya, et al., J. Org. Chem., 2009, 74, 118-134); and 4'-CH$_2$—C(=CH$_2$)-2' and analogs thereof (see, published PCT International Application WO 2008/154401, published on Dec. 8, 2008).

In certain embodiments, such 4' to 2' bridges independently comprise from 1 to 4 linked groups independently selected from —[C(R$_a$)(R$_b$)]$_n$—, —C(R$_a$)=C(R$_b$)—, —C(R$_a$)=N—, —C(=NR$_a$)—, —C(=O)—, —C(=S)—, —O—, —Si(R$_a$)$_2$—, —S(=O)$_x$—, and —N(R$_a$)—;

wherein:

x is 0, 1, or 2;

n is 1, 2, 3, or 4;

each R$_a$ and R$_b$ is, independently, H, a protecting group, hydroxyl, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, heterocycle radical, substituted heterocycle radical, heteroaryl, substituted heteroaryl, C$_5$-C$_7$ alicyclic radical, substituted C$_5$-C$_7$ alicyclic radical, halogen, OJ$_1$, NJ$_1$J$_2$, SJ$_1$, N$_3$, COOJ$_1$, acyl (C(=O)—H), substituted acyl, CN, sulfonyl (S(=O)$_2$-J$_1$), or sulfoxyl (S(=O)-J$_1$); and each J$_1$ and J$_2$ is, independently, H, C$_1$-C$_{12}$ alkyl, substituted C$_1$-C$_{12}$ alkyl, C$_2$-C$_{12}$ alkenyl, substituted C$_2$-C$_{12}$ alkenyl, C$_2$-C$_{12}$ alkynyl, substituted C$_2$-C$_{12}$ alkynyl, C$_5$-C$_{20}$ aryl, substituted C$_5$-C$_{20}$ aryl, acyl (C(=O)—H), substituted acyl, a heterocycle radical, a substituted heterocycle radical, C$_1$-C$_{12}$ aminoalkyl, substituted C$_1$-C$_{12}$ aminoalkyl, or a protecting group.

Nucleosides comprising bicyclic sugar moieties are referred to as bicyclic nucleosides or BNAs. Bicyclic nucleosides include, but are not limited to, (A) α-L-Methyleneoxy (4'-CH$_2$—O-2') BNA, (B) β-D-Methyleneoxy (4'-CH$_2$—O-2') BNA (also referred to as locked nucleic acid or LNA), (C) Ethyleneoxy (4'-(CH$_2$)$_2$—O-2') BNA, (D) Aminooxy (4'-CH$_2$—O—N(R)-2') BNA, (E) Oxyamino (4'-CH$_2$—N(R)—O-2') BNA, (F) Methyl(methyleneoxy) (4'-CH(CH$_3$)—O-2') BNA (also referred to as constrained ethyl or cEt), (G) methylene-thio (4'-CH$_2$—S-2') BNA, (H) methylene-amino (4'-CH2-N(R)-2') BNA, (I) methyl carbocyclic (4'-CH$_2$—CH(CH$_3$)-2') BNA, (J) propylene carbocyclic (4'-(CH$_2$)$_3$-2') BNA, and (K) Methoxy(ethyleneoxy) (4'-CH(CH$_2$OMe)-O-2') BNA (also referred to as constrained MOE or cMOE) as depicted below.

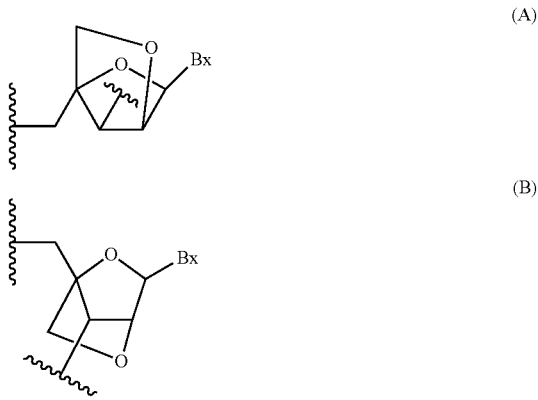

(C) 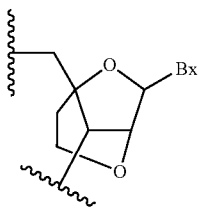

(D) 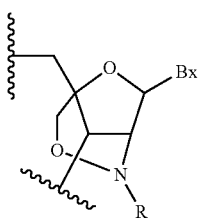

(E) 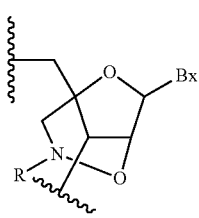

(F) 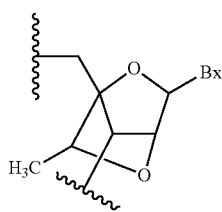

(G) 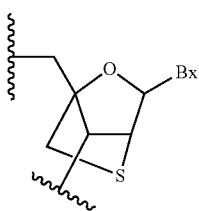

(H) 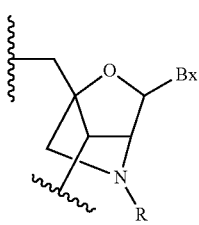

(I) 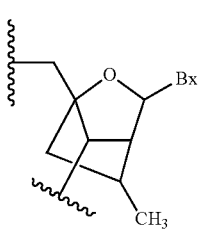

(J) 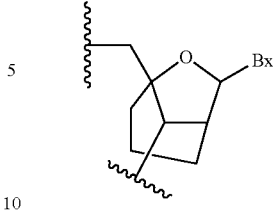

(K) 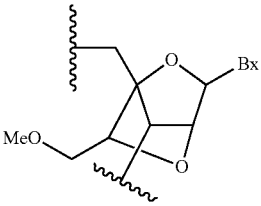

wherein Bx is a nucleobase moiety and R is, independently, H, a protecting group, or $C_1$-$C_{12}$ alkyl.

Additional bicyclic sugar moieties are known in the art, for example: Singh et al., *Chem. Commun.,* 1998, 4, 455-456; Koshkin et al., *Tetrahedron,* 1998, 54, 3607-3630; Wahlestedt et al., *Proc. Natl. Acad. Sci. U.S.A.,* 2000, 97, 5633-5638; Kumar et al., *Bioorg. Med. Chem. Lett.,* 1998, 8, 2219-2222; Singh et al., *J. Org. Chem.,* 1998, 63, 10035-10039; Srivastava et al., *J. Am. Chem. Soc.,* 129(26) 8362-8379 (Jul. 4, 2007); Elayadi et al., *Curr. Opinion Invens. Drugs,* 2001, 2, 5561; Braasch et al., *Chem. Biol.,* 2001, 8, 1-7; Orum et al., *Curr. Opinion Mol. Ther.,* 2001, 3, 239-243; U.S. Pat. Nos. 7,053,207, 6,268,490, 6,770,748, 6,794,499, 7,034,133, 6,525,191, 6,670,461, and 7,399,845; WO 2004/106356, WO 1994/14226, WO 2005/021570, and WO 2007/134181; U.S. Patent Publication Nos. US2004/0171570, US2007/0287831, and US2008/0039618; U.S. patent Ser. Nos. 12/129,154, 60/989,574, 61/026,995, 61/026,998, 61/056,564, 61/086,231, 61/097,787, and 61/099,844; and PCT International Applications Nos. PCT/US2008/064591, PCT/US2008/066154, and PCT/US2008/068922.

In certain embodiments, bicyclic sugar moieties and nucleosides incorporating such bicyclic sugar moieties are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') bicyclic nucleosides have been incorporated into antisense oligonucleotides that showed antisense activity (Frieden et al., *Nucleic Acids Research,* 2003, 21, 6365-6372).

In certain embodiments, substituted sugar moieties comprise one or more non-bridging sugar substituent and one or more bridging sugar substituent (e.g., 5'-substituted and 4'-2' bridged sugars). (see, PCT International Application WO 2007/134181, published on Nov. 22, 2007, wherein LNA is substituted with, for example, a 5'-methyl or a 5'-vinyl group).

In certain embodiments, modified sugar moieties are sugar surrogates. In certain such embodiments, the oxygen atom of the naturally occurring sugar is substituted, e.g., with a sulfer, carbon or nitrogen atom. In certain such embodiments, such modified sugar moiety also comprises bridging and/or non-bridging substituents as described above. For example, certain sugar surrogates comprise a 4'-sulfer atom and a substitution at the 2'-position (see, e.g., published U.S. Patent Application US2005/0130923, published on Jun. 16, 2005) and/or the 5' position. By way of additional example, carbocyclic bicyclic nucleosides having a 4'-2' bridge have been described (see, e.g., Freier et al., *Nucleic Acids Research,* 1997, 25(22), 4429-4443 and Albaek et al., *J. Org. Chem.,* 2006, 71, 7731-7740).

In certain embodiments, sugar surrogates comprise rings having other than 5-atoms. For example, in certain embodiments, a sugar surrogate comprises a six-membered tetrahydropyran. Such tetrahydropyrans may be further modified or substituted. Nucleosides comprising such modified tetrahydropyrans include, but are not limited to, hexitol nucleic acid (HNA), anitol nucleic acid (ANA), manitol nucleic acid (MNA) (see Leumann, C J. *Bioorg. & Med. Chem.* (2002) 10:841-854), fluoro HNA (F-HNA), and those compounds having Formula VII:

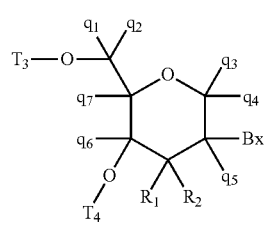

VII wherein independently for each of said at least one tetrahydropyran nucleoside analog of Formula VII:

Bx is a nucleobase moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and each of $R_1$ and $R_2$ is independently selected from hydrogen, halogen, substituted or unsubstituted alkoxy, $NJ_1J_2$, $SJ_1$, $N_3$, $OC(=X)J_1$, $OC(=X)NJ_1J_2$, $NJ_3C(=X)NJ_1J_2$, and CN, wherein X is O, S or $NJ_1$, and each $J_1$, $J_2$, and $J_3$ is, independently, H or $C_1$-$C_6$ alkyl.

In certain embodiments, the modified THP nucleosides of Formula VII are provided wherein $q_1$, $q_2$, $q_3$, $q_4$, $q_5$, $q_6$ and $q_7$ are each H. In certain embodiments, at least one of $q_1$, $q_2$, $q_3$, $q_4$, $q_5$, $q_6$ and $q_7$ is other than H. In certain embodiments, at least one of $q_1$, $q_2$, $q_3$, $q_4$, $q_5$, $q_6$ and $q_7$ is methyl. In certain embodiments, THP nucleosides of Formula VII are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry,* 2002, 10, 841-854).

Combinations of modifications are also provided without limitation, such as 2'-F-5'-methyl substituted nucleosides (see PCT International Application WO 2008/101157 Published on Aug. 21, 2008 for other disclosed 5',2'-bis substituted nucleosides) and replacement of the ribosyl ring oxygen atom with S and further substitution at the 2'-position (see published U.S. Patent Application US2005-0130923, published on Jun. 16, 2005) or alternatively 5'-substitution of a bicyclic nucleic acid (see PCT International Application WO 2007/134181, published on Nov. 22, 2007 wherein a 4'-$CH_2$—O-2' bicyclic nucleoside is further substituted at the 5' position with a 5'-methyl or a 5'-vinyl group). The synthesis and preparation of carbocyclic bicyclic nucleosides along with their oligomerization and biochemical studies have also been described (see, e.g., Srivastava et al., *J. Am. Chem. Soc.* 2007, 129(26), 8362-8379).

In certain embodiments, the present invention provides oligonucleotides comprising modified nucleosides. Those modified nucleotides may include modified sugars, modified nucleobases, and/or modified linkages. The specific modifications are selected such that the resulting oligonucleotides possess desirable characteristics. In certain embodiments, oligonucleotides comprise one or more RNA-like nucleosides. In certain embodiments, oligonucleotides comprise one or more DNA-like nucleotides.

c. Certain Nucleobases

In certain embodiments, nucleosides of the present invention comprise one or more unmodified nucleobases. In certain embodiments, nucleosides of the present invention comprise one or more modified nucleobases.

In certain embodiments, modified nucleobases are selected from: universal bases, hydrophobic bases, promiscuous bases, size-expanded bases, and fluorinated bases as defined herein. 5-substituted pyrimidines, 6-azapyrimidines and N-2, N-6 and O-6 substituted purines, including 2-aminopropyladenine, 5-propynyluracil; 5-propynylcytosine; 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl ($CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine, 3-deazaguanine and 3-deazaadenine, universal bases, hydrophobic bases, promiscuous bases, size-expanded bases, and fluorinated bases as defined herein. Further modified nucleobases include tricyclic pyrimidines such as phenoxazine cytidine([5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-13][1,4]benzoxazin-2 (3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified nucleobases may also include those in which the purine or pyrimidine base is replaced with other heterocycles, for example 7-deaza-adenine, 7-deazaguanosine, 2-aminopyridine and 2-pyridone. Further nucleobases include those disclosed in U.S. Pat. No. 3,687,808, those disclosed in *The Concise Encyclopedia Of Polymer Science And Engineering,* Kroschwitz, J. I., Ed., John Wiley & Sons, 1990, 858-859; those disclosed by Englisch et al., *Angewandte Chemie, International Edition,* 1991, 30, 613; and those disclosed by Sanghvi, Y. S., Chapter 15, *Antisense Research and Applications,* Crooke, S. T. and Lebleu, B., Eds., CRC Press, 1993, 273-288.

Representative United States patents that teach the preparation of certain of the above noted modified nucleobases as well as other modified nucleobases include without limitation, U.S. Pat. Nos. 3,687,808; 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121; 5,596,091; 5,614,617; 5,645,985; 5,681,941; 5,750,692; 5,763,588; 5,830,653 and 6,005,096, certain of which are commonly owned with the instant application, and each of which is herein incorporated by reference in its entirety.

d. Certain Internucleoside Linkages

In certain embodiments, the present invention provides oligonucleotides comprising linked nucleosides. In such embodiments, nucleosides may be linked together using any internucleoside linkage.

The two main classes of internucleoside linking groups are defined by the presence or absence of a phosphorus atom. Representative phosphorus containing internucleoside linkages include, but are not limited to, phosphodiesters (P=O), phosphotriesters, methylphosphonates, phosphoramidate, and phosphorothioates (P=S). Representative non-phosphorus containing internucleoside linking groups include, but are not limited to, methylenemethylimino ($—CH_2—N(CH_3)—O—CH_2—$), thiodiester ($—O—C(O)—S—$), thionocarbamate ($—O—C(O)(NH)—S—$); siloxane ($—O—Si(H)_2—O—$); and N,N'-dimethylhydrazine ($—CH_2—N(CH_3)—N(CH_3)—$). Modified linkages, compared to natural phosphodiester linkages, can be used to alter, typically increase, nuclease resistance of the oligonucleotide. In certain embodiments, internucleoside linkages having a chiral atom can be prepared as a racemic mixture, or as separate enantiomers. Representative chiral linkages include, but are not limited to, alkylphosphonates and phosphorothioates. Methods of preparation of phosphorous-containing and non-phosphorous-containing internucleoside linkages are well known to those skilled in the art.

The oligonucleotides described herein contain one or more asymmetric centers and thus give rise to enantiomers, diastereomers, and other stereoisomeric configurations that may be defined, in terms of absolute stereochemistry, as (R) or (S), α or β such as for sugar anomers, or as (D) or (L) such as for amino acids etc. Included in the antisense compounds provided herein are all such possible isomers, as well as their racemic and optically pure forms.

Neutral internucleoside linkages include without limitation, phosphotriesters, methylphosphonates, MMI (3'-$CH_2$—$N(CH_3)$—O-5'), amide-3 (3'-$CH_2$—C(=O)—N(H)-5'), amide-4 (3'-$CH_2$—N(H)—C(=O)-5'), formacetal (3'-O—$CH_2$—O-5'), and thioformacetal (3'-S—$CH_2$—O-5'). Further neutral internucleoside linkages include nonionic linkages comprising siloxane (dialkylsiloxane), carboxylate ester, carboxamide, sulfide, sulfonate ester and amides (See for example: *Carbohydrate Modifications in Antisense Research*; Y. S. Sanghvi and P. D. Cook, Eds., ACS Symposium Series 580; Chapters 3 and 4, 40-65). Further neutral internucleoside linkages include nonionic linkages comprising mixed N, O, S and $CH_2$ component parts.

e. Certain Motifs

In certain embodiments, the present invention provides compounds comprising oligonucleotides. In certain embodiments, such oligonucleotides comprise one or more chemical modification. In certain embodiments, chemically modified oligonucleotides comprise one or more modified sugars. In certain embodiments, chemically modified oligonucleotides comprise one or more modified nucleobases. In certain embodiments, chemically modified oligonucleotides comprise one or more modified internucleoside linkages. In certain embodiments, the chemical modifications (sugar modifications, nucleobase modifications, and/or linkage modifications) define a pattern or motif. In certain embodiments, the patterns of chemical modifications of sugar moieties, internucleoside linkages, and nucleobases are each independent of one another. Thus, an oligonucleotide may be described by its sugar modification motif, internucleoside linkage motif and/or nucleobase modification motif (as used herein, nucleobase modification motif describes the chemical modifications to the nucleobases independent of the sequence of nucleobases).

i. Certain Sugar Motifs

In certain embodiments, oligonucleotides comprise one or more type of modified sugar moieties and/or naturally occurring sugar moieties arranged along an oligonucleotide or region thereof in a defined pattern or sugar modification motif. Such motifs may include any of the sugar modifications discussed herein and/or other known sugar modifications.

In certain embodiments, the oligonucleotides comprise or consist of a region having uniform sugar modifications. In certain such embodiments, each nucleoside of the region comprises the same RNA-like sugar modification. In certain embodiments, each nucleoside of the region is a 2'-F nucleoside. In certain embodiments, each nucleoside of the region is a 2'-OMe nucleoside. In certain embodiments, each nucleoside of the region is a 2'-MOE nucleoside. In certain embodiments, each nucleoside of the region is a cEt nucleoside. In certain embodiments, each nucleoside of the region is an LNA nucleoside. In certain embodiments, the uniform region constitutes all or essentially all of the oligonucleotide. In certain embodiments, the region constitutes the entire oligonucleotide except for 1-4 terminal nucleosides.

In certain embodiments, oligonucleotides of the present invention comprise one or more regions of alternating sugar modifications, wherein the nucleosides alternate between nucleosides having a sugar modification of a first type and nucleosides having a sugar modification of a second type. In certain embodiments, nucleosides of both types are RNA-like nucleosides. In certain embodiments the alternating nucleosides are selected from: 2'-Ome, 2'-F, 2'-MOE, LNA, and cEt. In certain embodiments, the alternating modifications are 2'-F and 2'-Ome. Such regions may be contiguous or may be interrupted by differently modified nucleosides or conjugated nucleosides.

In certain embodiments, the alternating region of alternating modifications each consist of a single nucleoside (i.e., the pattern is $(AB)_xA_y$ wherein A is a nucleoside having a sugar modification of a first type and B is a nucleoside having a sugar modification of a second type; x is 1-20 and y is 0 or 1). In certain embodiments, one or more alternating regions in an alternating motif includes more than a single nucleoside of a type. For example, oligonucleotides of the present invention may include one or more regions of any of the following nucleoside motifs:

AABBAA;
ABBABB;
AABAAB;
ABBABAABB;
ABABAA;
AABABAB;
ABABAA;
ABBAABBABABAA;
BABBAABBABABAA;
ABABBAABBABABAA; or
ABABABABABABABAB;

wherein A is a nucleoside of a first type and B is a nucleoside of a second type. In certain embodiments, A and B are each selected from 2'-F, 2'-Ome, BNA, and MOE.

In certain embodiments, oligonucleotides having such an alternating motif also comprise a 5' terminal nucleoside of Formula I, II, III, IV, or V.

In certain embodiments, oligonucleotides of the present invention comprise a region having a 2-2-3 motif. Such regions comprises the following motif:

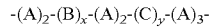

wherein: A is a first type of modified nucleoside;
B and C, are nucleosides that are differently modified than A, however, B and C may have the same or different modifications as one another;
x and y are from 1 to 15.

In certain embodiments, A is a 2'-Ome modified nucleoside. In certain embodiments, B and C are both 2'-F modified nucleosides. In certain embodiments, A is a 2'-Ome modified nucleoside and B and C are both 2'-F modified nucleosides.

It is to be understood, that certain of the above described motifs and modifications may be combined. Since a motif may comprise only a few nucleosides, a particular oligonucleotide may comprise two or more motifs. By way of non-limiting example, in certain embodiments, oligonucleotides may have nucleoside motifs as described in the table below. In the table below, the term "None" indicates that a particular feature is not present in the oligonucleotide. For example, "None" in the column labeled "5' motif/modification" indicates that the 5' end of the oligonucleotide comprises the first nucleoside of the central motif.

| 5' motif/modification | Central Motif | 3'-motif |
|---|---|---|
| Compound of Formula I, II, III, IV, or V | Alternating | 2 MOE nucleosides |
| Compound of Formula I, II, III, IV, or V | 2-2-3 motif | 2 MOE nucleosides |
| Compound of Formula I, II, III, IV, or V | Uniform | 2 MOE nucleosides |
| Compound of Formula I, II, III, IV, or V | Alternating | 2 MOE nucleosides |
| Compound of Formula I, II, III, IV, or V | Alternating | 2 MOE A's |
| Compound of Formula I, II, III, IV, or V | 2-2-3 motif | 2 MOE A's |
| Compound of Formula I, II, III, IV, or V | Uniform | 2 MOE A's |
| Compound of Formula I, II, III, IV, or V | Alternating | 2 MOE U's |
| Compound of Formula I, II, III, IV, or V | 2-2-3 motif | 2 MOE U's |
| Compound of Formula I, II, III, IV, or V | Uniform | 2 MOE U's |
| Compound of Formula I, II, III, IV, or V | Alternating | 2 MOE nucleosides |
| Compound of Formula I, II, III, IV, or V | 2-2-3 motif | 2 MOE nucleosides |
| Compound of Formula I, II, III, IV, or V | Uniform | 2 MOE nucleosides |

In certain embodiments, oligonucleosides have the following sugar motif:

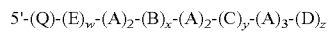

wherein:
Q is a nucleoside comprising a stabilized phosphate moiety. In certain embodiments, Q is a nucleoside having Formula I, II, III, IV, or V;
A is a first type of modified nucleoside;
B, C, D, and E are nucleosides that are differently modified than A, however, B, C, D, and E may have the same or different modifications as one another;
w and z are from 0 to 15;
x and y are from 1 to 15.
In certain embodiments, the sum of w, x, and y is 5-25.

In certain embodiments, oligonucleosides have the following sugar motif:

wherein:
Q is a nucleoside comprising a stabilized phosphate moiety. In certain embodiments, Q is a nucleoside having Formula I, II, III, IV, or V;
A is a first type of modified nucleoside;
B is a second type of modified nucleoside;
D is a modified nucleoside comprising a modification different from the nucleoside adjacent to it. Thus, if y is 0, then D must be differently modified than B and if y is 1, then D must be differently modified than A. In certain embodiments, D differs from both A and B.
X is 5-15;
Y is 0 or 1;
Z is 0-4.

In certain embodiments, oligonucleosides have the following sugar motif:

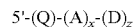

wherein:
Q is a nucleoside comprising a stabilized phosphate moiety. In certain embodiments, Q is a nucleoside having Formula I, II, III, IV, or V;
A is a first type of modified nucleoside;
D is a modified nucleoside comprising a modification different from A.
X is 11-30;
Z is 0-4.

In certain embodiments A, B, C, and D in the above motifs are selected from: 2'-Ome, 2'-F, 2'-MOE, LNA, and cEt. In certain embodiments, D represents terminal nucleosides. In certain embodiments, such terminal nucleosides are not designed to hybridize to the target nucleic acid (though one or more might hybridize by chance). In certain embodiments, the nucleobase of each D nucleoside is adenine, regardless of the identity of the nucleobase at the corresponding position of the target nucleic acid. In certain embodiments the nucleobase of each D nucleoside is thymine.

ii. Certain Internucleoside Linkage Motifs

In certain embodiments, oligonucleotides comprise modified internucleoside linkages arranged along the oligonucleotide or region thereof in a defined pattern or modified internucleoside linkage motif. In certain embodiments, oligonucleotides comprise a region having an alternating internucleoside linkage motif. In certain embodiments, oligonucleotides of the present invention comprise a region of uniformly modified internucleoside linkages. In certain such embodiments, the oligonucleotide comprises a region that is uniformly linked by phosphorothioate internucleoside linkages. In certain embodiments, the oligonucleotide is uniformly linked by phosphorothioate internucleoside linkages. In certain embodiments, each internucleoside linkage of the oligonucleotide is selected from phosphodiester and phosphorothioate. In certain embodiments, each internucleoside linkage of the oligonucleotide is selected from phosphodiester and phosphorothioate and at least one internucleoside linkage is phosphorothioate.

In certain embodiments, the oligonucleotide comprises at least 6 phosphorothioate internucleoside linkages. In certain embodiments, the oligonucleotide comprises at least 8 phosphorothioate internucleoside linkages. In certain embodiments, the oligonucleotide comprises at least 10 phosphorothioate internucleoside linkages. In certain embodiments, the oligonucleotide comprises at least one block of at least 6 consecutive phosphorothioate internucleoside linkages. In certain embodiments, the oligonucleotide comprises at least one block of at least 8 consecutive phosphorothioate internucleoside linkages. In certain embodiments, the oligonucleotide comprises at least one block of at least 10 consecutive phosphorothioate internucleoside linkages. In certain embodiments, the oligonucleotide comprises at least one block of at least one 12 consecutive phosphorothioate internucleoside linkages. In certain such embodiments, at least one such block is located at the 3' end of the oligonucleotide. In certain such embodiments, at least one such block is located within 3 nucleosides of the 3' end of the oligonucleotide.

Oligonucleotides having any of the various sugar motifs described herein, may have any linkage motif. For example, the oligonucleotides, including but not limited to those described above, may have a linkage motif selected from non-limiting the table below:

| 5' most linkage | Central region | 3'-region |
|---|---|---|
| PS | Alternating PO/PS | 6 PS |
| PS | Alternating PO/PS | 7 PS |
| PS | Alternating PO/PS | 8 PS | iii. Certain Nucleobase Modification Motifs

In certain embodiments, oligonucleotides comprise chemical modifications to nucleobases arranged along the oligonucleotide or region thereof in a defined pattern or nucleobases modification motif. In certain such embodiments, nucleobase modifications are arranged in a gapped motif. In certain embodiments, nucleobase modifications are arranged in an alternating motif. In certain embodiments, each nucleobase is modified. In certain embodiments, none of the nucleobases is chemically modified.

In certain embodiments, oligonucleotides comprise a block of modified nucleobases. In certain such embodiments, the block is at the 3'-end of the oligonucleotide. In certain embodiments the block is within 3 nucleotides of the 3'-end of the oligonucleotide. In certain such embodiments, the block is at the 5'-end of the oligonucleotide. In certain embodiments the block is within 3 nucleotides of the 5'-end of the oligonucleotide.

In certain embodiments, nucleobase modifications are a function of the natural base at a particular position of an oligonucleotide. For example, in certain embodiments each purine or each pyrimidine in an oligonucleotide is modified. In certain embodiments, each adenine is modified. In certain embodiments, each guanine is modified. In certain embodiments, each thymine is modified. In certain embodiments, each cytosine is modified. In certain embodiments, each uracil is modified.

In certain embodiments, some, all, or none of the cytosine moieties in an oligonucleotide are 5-methyl cytosine moieties. Herein, 5-methyl cytosine is not a "modified nucleobase." Accordingly, unless otherwise indicated, unmodified nucleobases include both cytosine residues having a 5-methyl and those lacking a 5 methyl. In certain embodiments, the methylation state of all or some cytosine nucleobases is specified.

a. Certain Overall Lengths

In certain embodiments, the present invention provides oligonucleotides of any of a variety of ranges of lengths. In certain embodiments, the invention provides oligonucleotides consisting of X to Y linked nucleosides, where X represents the fewest number of nucleosides in the range and Y represents the largest number of nucleosides in the range. In certain such embodiments, X and Y are each independently selected from 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, and 50; provided that X≤Y. For example, in certain embodiments, the invention provides oligonucleotides consisting of 8 to 9, 8 to 10, 8 to 11, 8 to 12, 8 to 13, 8 to 14, 8 to 15, 8 to 16, 8 to 17, 8 to 18, 8 to 19, 8 to 20, 8 to 21, 8 to 22, 8 to 23, 8 to 24, 8 to 25, 8 to 26, 8 to 27, 8 to 28, 8 to 29, 8 to 30, 9 to 10, 9 to 11, 9 to 12, 9 to 13, 9 to 14, 9 to 15, 9 to 16, 9 to 17, 9 to 18, 9 to 19, 9 to 20, 9 to 21, 9 to 22, 9 to 23, 9 to 24, 9 to 25, 9 to 26, 9 to 27, 9 to 28, 9 to 29, 9 to 30, 10 to 11, 10 to 12, 10 to 13, 10 to 14, 10 to 15, 10 to 16, 10 to 17, 10 to 18, 10 to 19, 10 to 20, 10 to 21, 10 to 22, 10 to 23, 10 to 24, 10 to 25, 10 to 26, 10 to 27, 10 to 28, 10 to 29, 10 to 30, 11 to 12, 11 to 13, 11 to 14, 11 to 15, 11 to 16, 11 to 17, 11 to 18, 11 to 19, 11 to 20, 11 to 21, 11 to 22, 11 to 23, 11 to 24, 11 to 25, 11 to 26, 11 to 27, 11 to 28, 11 to 29, 11 to 30, 12 to 13, 12 to 14, 12 to 15, 12 to 16, 12 to 17, 12 to 18, 12 to 19, 12 to 20, 12 to 21, 12 to 22, 12 to 23, 12 to 24, 12 to 25, 12 to 26, 12 to 27, 12 to 28, 12 to 29, 12 to 30, 13 to 14, 13 to 15, 13 to 16, 13 to 17, 13 to 18, 13 to 19, 13 to 20, 13 to 21, 13 to 22, 13 to 23, 13 to 24, 13 to 25, 13 to 26, 13 to 27, 13 to 28, 13 to 29, 13 to 30, 14 to 15, 14 to 16, 14 to 17, 14 to 18, 14 to 19, 14 to 20, 14 to 21, 14 to 22, 14 to 23, 14 to 24, 14 to 25, 14 to 26, 14 to 27, 14 to 28, 14 to 29, 14 to 30, 15 to 16, 15 to 17, 15 to 18, 15 to 19, 15 to 20, 15 to 21, 15 to 22, 15 to 23, 15 to 24, 15 to 25, 15 to 26, 15 to 27, 15 to 28, 15 to 29, 15 to 30, 16 to 17, 16 to 18, 16 to 19, 16 to 20, 16 to 21, 16 to 22, 16 to 23, 16 to 24, 16 to 25, 16 to 26, 16 to 27, 16 to 28, 16 to 29, 16 to 30, 17 to 18, 17 to 19, 17 to 20, 17 to 21, 17 to 22, 17 to 23, 17 to 24, 17 to 25, 17 to 26, 17 to 27, 17 to 28, 17 to 29, 17 to 30, 18 to 19, 18 to 20, 18 to 21, 18 to 22, 18 to 23, 18 to 24, 18 to 25, 18 to 26, 18 to 27, 18 to 28, 18 to 29, 18 to 30, 19 to 20, 19 to 21, 19 to 22, 19 to 23, 19 to 24, 19 to 25, 19 to 26, 19 to 29, 19 to 28, 19 to 29, 19 to 30, 20 to 21, 20 to 22, 20 to 23, 20 to 24, 20 to 25, 20 to 26, 20 to 27, 20 to 28, 20 to 29, 20 to 30, 21 to 22, 21 to 23, 21 to 24, 21 to 25, 21 to 26, 21 to 27, 21 to 28, 21 to 29, 21 to 30, 22 to 23, 22 to 24, 22 to 25, 22 to 26, 22 to 27, 22 to 28, 22 to 29, 22 to 30, 23 to 24, 23 to 25, 23 to 26, 23 to 27, 23 to 28, 23 to 29, 23 to 30, 24 to 25, 24 to 26, 24 to 27, 24 to 28, 24 to 29, 24 to 30, 25 to 26, 25 to 27, 25 to 28, 25 to 29, 25 to 30, 26 to 27, 26 to 28, 26 to 29, 26 to 30, 27 to 28, 27 to 29, 27 to 30, 28 to 29, 28 to 30, or 29 to 30 linked nucleosides. In embodiments where the number of nucleosides of an oligonucleotide of a compound is limited, whether to a range or to a specific number, the compound may, nonetheless further comprise additional other substituents. For example, an oligonucleotide comprising 8-30 nucleosides excludes oligonucleotides having 31 nucleosides, but, unless otherwise indicated, such an oligonucleotide may further comprise, for example one or more conjugates, terminal groups, or other substituents.

Further, where an oligonucleotide is described by an overall length range and by regions having specified lengths, and where the sum of specified lengths of the regions is less than the upper limit of the overall length range, the oligonucleotide may have additional nucleosides, beyond those of the specified regions, provided that the total number of nucleosides does not exceed the upper limit of the overall length range.

b. Certain Oligonucleotides

In certain embodiments, oligonucleotides of the present invention are characterized by their sugar motif, internucleoside linkage motif, nucleobase modification motif and overall length. In certain embodiments, such parameters are each independent of one another. Thus, each internucleoside linkage of an oligonucleotide having a gapmer sugar motif may be modified or unmodified and may or may not follow the gapmer modification pattern of the sugar modifications. Thus, the internucleoside linkages within the wing regions of a sugar-gapmer may be the same or different from one another and may be the same or different from the internucleoside linkages of the gap region. Likewise, such sugar-gapmer oligonucleotides may comprise one or more modified nucleobase independent of the gapmer pattern of the sugar modifications. One of skill in the art will appreciate that such motifs may be combined to create a variety of oligonucleotides, such as those provided in the non-limiting table below. As is apparent from the above, non-limiting tables, the lengths of the regions defined by a nucleoside motif and that of a linkage motif need not be the same. To further illustrate, and not to limit in any way, nucleoside motifs and sequence motifs are combined to show five non-limiting examples in the table below. The first column of the table lists nucleosides and linkages by position from Ni (the first nucleoside at the 5'-end) to N20 (the 20$^{th}$ position from the 5'-end). In certain embodiments, oligonucleotides of the present invention are longer than 20 nucleosides (the table is merely exemplary). Certain positions in the table recite the nucleoside or linkage "none" indicating that the oligonucleotide has no nucleoside at that position.

In the above, non-limiting examples:

Column A represent an oligonucleotide consisting of 20 linked nucleosides, wherein the oligonucleotide comprises: a modified 5'-terminal nucleoside of Formula I, II, III, N, or V; a region of alternating nucleosides; a region of alternating linkages; two 3'-terminal MOE nucleosides, each of which comprises a uracil base; and a region of six phosphorothioate linkages at the 3'-end.

Column B represents an oligonucleotide consisting of 18 linked nucleosides, wherein the oligonucleotide comprises: a modified 5'-terminal nucleoside of Formula Formula I, II, III, IV, or V; a 2-2-3 motif wherein the modified nucleoside of the 2-2-3 motif are 2'O-Me and the remaining nucleosides are all 2'-F; two 3'-terminal MOE nucleosides, each of which comprises a uracil base; and a region of six phosphorothioate linkages at the 3'-end.

Column C represents an oligonucleotide consisting of 20 linked nucleosides, wherein the oligonucleotide comprises: a modified 5'-terminal nucleoside of Formula I, II, III, IV, or V; a region of uniformly modified 2'-F nucleosides; two 3'-terminal MOE nucleosides, each of which comprises a uracil base; and wherein each internucleoside linkage is a phosphorothioate linkage.

Column D represents an oligonucleotide consisting of 20 linked nucleosides, wherein the oligonucleotide comprises: a modified 5'-terminal nucleoside of Formula I, II, III, N, or V; a region of alternating 2'-Ome/2'-F nucleosides; a region of uniform 2'F nucleosides; a region of alternating phosphorothioate/phosphodiester linkages; two 3'-terminal MOE

| Pos | A | B | C | D | E |
|---|---|---|---|---|---|
| N1 | Formula I, II, III, IV, or V | Formula I, II, III, IV, or V | Formula I, II, III, IV, or V | Formula I, II, III, IV, or V | Formula I, II, III, IV, or V |
| L1 | PS | PS | PS | PS | PO |
| N2 | 2'-F | 2'-F | 2'-F | 2'-Ome | MOE |
| L2 | PS | PS | PS | PO | PS |
| N3 | 2'-Ome | 2'-F | 2'-F | 2'-F | 2'-F |
| L3 | PO | PS | PS | PS | PS |
| N4 | 2'-F | 2'-F | 2'-F | 2'-Ome | 2'-F |
| L4 | PS | PS | PS | PO | PS |
| N5 | 2'-Ome | 2'-F | 2'-F | 2'-F | 2'-Ome |
| L5 | PO | PS | PS | PS | PO |
| N6 | 2'-F | 2'-Ome | 2'-F | 2'-Ome | 2'-Ome |
| L6 | PS | PO | PS | PO | PO |
| N7 | 2'-Ome | 2'-Ome | 2'-F | 2'-F | 2'-Ome |
| L7 | PO | PO | PS | PS | PO |
| N8 | 2'-F | 2'-F | 2'-F | 2'-Ome | 2'-F |
| L8 | PS | PS | PS | PO | PS |
| N9 | 2'-Ome | 2'-F | 2'-F | 2'-F | 2'-F |
| L9 | PO | PS | PS | PS | PS |
| N10 | 2'-F | 2'-Ome | 2'-F | 2'-Ome | 2'-Ome |
| L10 | PS | PO | PS | PO | PO |
| N11 | 2'-Ome | 2'-Ome | 2'-F | 2'-F | 2'Ome |
| L11 | PO | PO | PS | PS | PO |
| N12 | 2'-F | 2'-F | 2'-F | 2'-F | 2'-F |
| L12 | PS | PS | PS | PO | PS |
| N13 | 2'-Ome | 2'-F | 2'-F | 2'-F | 2'-F |
| L13 | PO | PS | PS | PS | PS |
| N14 | 2'-F | 2'-Ome | 2'-F | 2'-F | 2'-F |
| L14 | PS | PS | PS | PS | PS |
| N15 | 2'-Ome | 2'Ome | 2'-F | 2'-F | 2'-MOE |
| L15 | PS | PS | PS | PS | PS |
| N16 | 2'-F | 2'Ome | 2'-F | 2'-F | 2'-MOE |
| L16 | PS | PS | PS | PS | PS |
| N17 | 2'-Ome | 2'-MOE U | 2'-F | 2'-F | 2'-MOE |
| L17 | PS | PS | PS | PS | None |
| N18 | 2'-F | 2'-MOE U | 2'-F | 2'-Ome | None |
| L18 | PS | None | PS | PS | None |
| N19 | 2'-MOE U | None | 2'-MOE U | 2'-MOE A | None |
| L19 | PS | None | PS | PS | None |
| N20 | 2'-MOE U | None | 2'-MOE U | 2'-MOE A | None | nucleosides, each of which comprises an adenine base; and a region of six phosphorothioate linkages at the 3'-end.

Column E represents an oligonucleotide consisting of 17 linked nucleosides, wherein the oligonucleotide comprises: a modified 5'-terminal nucleoside of Formula I, II, III, N, or V; a 2-2-3 motif wherein the modified nucleoside of the 2-2-3 motif are 2'F and the remaining nucleosides are all 2'-Ome; three 3'-terminal MOE nucleosides.

The above examples are provided solely to illustrate how the described motifs may be used in combination and are not intended to limit the invention to the particular combinations or the particular modifications used in illustrating the combinations. Further, specific examples herein, including, but not limited to those in the above table are intended to encompass more generic embodiments. For example, column A in the above table exemplifies a region of alternating 2'-Ome and 2'-F nucleosides. Thus, that same disclosure also exemplifies a region of alternating different 2'-modifications. It also exemplifies a region of alternating 2'-O-alkyl and 2'-halogen nucleosides. It also exemplifies a region of alternating differently modified nucleosides. All of the examples throughout this specification contemplate such generic interpretation.

It is also noted that the lengths of the oligonucleotides, such as those exemplified in the above tables, can be easily manipulated by lengthening or shortening one or more of the described regions, without disrupting the motif In certain embodiments, the invention provides oligonucleotides wherein the 5'-terminal nucleoside (position 1) is a compound of Formula I, II, III, IV, or V and the position 2 nucleoside comprises a 2'-modification. In certain such embodiments, the 2'-modification of the position 2 nucleoside is selected from halogen, alkyl, and substituted alkyl. In certain embodiments, the 2'-modification of the position 2 nucleoside is selected from 2'-F and 2'-alkyl. In certain embodiments, the 2'-modification of the position 2 nucleoside is 2'-F. In certain embodiments, the 2'-substituted of the position 2 nucleoside is an unmodified OH (as in naturally occurring RNA).

In certain embodiments, the position 3 nucleoside is a modified nucleoside. In certain embodiments, the position 3 nucleoside is a bicyclic nucleoside. In certain embodiments, the position 3 nucleoside comprises a sugar surrogate. In certain such embodiments, the sugar surrogate is a tetrahydropyran. In certain embodiments, the sugar of the position 3 nucleoside is a F-HNA.

In certain embodiments, an antisense compound comprises an oligonucleotide comprising 10 to 30 linked nucleosides wherein the oligonucleotide comprises: a position 1 modified nucleoside of Formula I, II, III, IV, or V; a position 2 nucleoside comprising a sugar moiety which is differently modified compared to the sugar moiety of the position 1 modified nucleoside; and from 1 to 4 3'-terminal group nucleosides each comprising a 2'-modification; and wherein at least the seven 3'-most internucleoside linkages are phosphorothioate linkages.

c. Certain Conjugate Groups

In certain embodiments, oligonucleotides are modified by attachment of one or more conjugate groups. In general, conjugate groups modify one or more properties of the attached oligonucleotide, including but not limited to pharmacodynamics, pharmacokinetics, stability, binding, absorption, cellular distribution, cellular uptake, charge and clearance. Conjugate groups are routinely used in the chemical arts and are linked directly or via an optional conjugate linking moiety or conjugate linking group to a parent compound such as an oligonucleotide. Conjugate groups include without limitation, intercalators, reporter molecules, polyamines, polyamides, polyethylene glycols, thioethers, polyethers, cholesterols, thiocholesterols, cholic acid moieties, folate, lipids, phospholipids, biotin, phenazine, phenanthridine, anthraquinone, adamantane, acridine, fluoresceins, rhodamines, coumarins and dyes. Certain conjugate groups have been described previously, for example: cholesterol moiety (Letsinger et al., Proc. Natl. Acad. Sci. USA, 1989, 86, 6553-6556), cholic acid (Manoharan et al., Bioorg. Med. Chem. Let., 1994, 4, 1053-1060), a thioether, e.g., hexyl-S-tritylthiol (Manoharan et al., Ann. N.Y. Acad. Sci., 1992, 660, 306-309; Manoharan et al., Bioorg. Med. Chem. Let., 1993, 3, 2765-2770), a thiocholesterol (Oberhauser et al., Nucl. Acids Res., 1992, 20, 533-538), an aliphatic chain, e.g., do-decan-diol or undecyl residues (Saison-Behmoaras et al., EMBO J., 1991, 10, 1111-1118; Kabanov et al., FEBS Lett., 1990, 259, 327-330; Svinarchuk et al., Biochimie, 1993, 75, 49-54), a phospholipid, e.g., di-hexadecyl-rac-glycerol or triethyl-ammonium 1,2-di-O-hexadecyl-rac-glycero-3-H-phosphonate (Manoharan et al., Tetrahedron Lett., 1995, 36, 3651-3654; Shea et al., Nucl. Acids Res., 1990, 18, 3777-3783), a polyamine or a polyethylene glycol chain (Manoharan et al., Nucleosides & Nucleotides, 1995, 14, 969-973), or adamantane acetic acid (Manoharan et al., Tetrahedron Lett., 1995, 36, 3651-3654), a palmityl moiety (Mishra et al., Biochim. Biophys. Acta, 1995, 1264, 229-237), or an octadecylamine or hexylaminocarbonyl-oxycholesterol moiety (Crooke et al., J. Pharmacol. Exp. Ther., 1996, 277, 923-937).

In certain embodiments, a conjugate group comprises an active drug substance, for example, aspirin, warfarin, phenylbutazone, ibuprofen, suprofen, fen-bufen, ketoprofen, (S)-(+)-pranoprofen, carprofen, dansylsarcosine, 2,3,5-triiodobenzoic acid, flufenamic acid, folinic acid, a benzothiadiazide, chlorothiazide, a diazepine, indo-methicin, a barbiturate, a cephalosporin, a sulfa drug, an antidiabetic, an antibacterial or an antibiotic.

In certain embodiments, conjugate groups are directly attached to oligonucleotides. In certain embodiments, conjugate groups are attached to oligonucleotides by a conjugate linking group. In certain such embodiments, conjugate linking groups, including, but not limited to, bifunctional linking moieties such as those known in the art are amenable to the compounds provided herein. Conjugate linking groups are useful for attachment of conjugate groups, such as chemical stabilizing groups, functional groups, reporter groups and other groups to selective sites in a parent compound such as for example an oligonucleotide. In general a bifunctional linking moiety comprises a hydrocarbyl moiety having two functional groups. One of the functional groups is selected to bind to a parent molecule or compound of interest and the other is selected to bind essentially any selected group such as chemical functional group or a conjugate group. In some embodiments, the conjugate linker comprises a chain structure or an oligomer of repeating units such as ethylene glycol or amino acid units. Examples of functional groups that are routinely used in a bifunctional linking moiety include, but are not limited to, electrophiles for reacting with nucleophilic groups and nucleophiles for reacting with electrophilic groups. In some embodiments, bifunctional linking moieties include amino, hydroxyl, carboxylic acid, thiol, unsaturations (e.g., double or triple bonds), and the like.

Some nonlimiting examples of conjugate linking moieties include pyrrolidine, 8-amino-3,6-dioxaoctanoic acid (ADO), succinimidyl 4-(N-maleimidomethyl) cyclohexane-1-carboxylate (SMCC) and 6-aminohexanoic acid (AHEX or AHA). Other linking groups include, but are not limited to, substituted $C_1$-$C_{10}$ alkyl, substituted or unsubstituted $C_2$-$C_{10}$ alkenyl or substituted or unsubstituted $C_2$-$C_{10}$ alkynyl, wherein a nonlimiting list of preferred substituent groups includes hydroxyl, amino, alkoxy, carboxy, benzyl, phenyl, nitro, thiol, thioalkoxy, halogen, alkyl, aryl, alkenyl and alkynyl.

Conjugate groups may be attached to either or both ends of an oligonucleotide (terminal conjugate groups) and/or at any internal position.

In certain embodiments, conjugate groups are at the 3'-end of an oligonucleotide. In certain embodiments, conjugate groups are near the 3'-end. In certain embodiments, conjugates are attached at the 3'end of an oligonucleotide, but before one or more terminal group nucleosides. In certain embodiments, conjugate groups are placed within a terminal group. In certain embodiments, a conjugate group is attached to the 3'-terminal nucleoside. In certain such embodiment, it is attached at the 3'-position of the 3'-terminal nucleoside. In certain embodiments, it is attached at the 2'-position of the 3'-terminal nucleoside.

In certain embodiments, compounds comprise an oligonucleotide. In certain embodiments, an compound comprises an oligonucleotide and one or more conjugate and/or terminal groups. Such conjugate and/or terminal groups may be added to oligonucleotides having any of the chemical motifs discussed above. Thus, for example, a compound comprising an oligonucleotide having region of alternating nucleosides may comprise a terminal group.

In certain embodiments, a conjugate is attached at the 2'-position of a nucleoside. In certain embodiments, a conjugate is attached to a nucleoside at one or more of: position 1,6 or 8 of the oligonucleotide, counting from the 5'-end. In certain embodiments a conjugate is attached to a nucleoside at one or more of: position 13, 15, or 20 of the oligonucleotide, counting from the 3'-end.

In certain embodiments, conjugates interrupt motifs. For example, in certain embodiments, oligonucleotides of the present invention have an alternating motif that spans positions 1-19 and a conjugate at position 8 (from the 5'-end) as follows:

Po-ABABABAXABABABABABA-

Wherein A represents nucleosides of a first-type;
B represents nucleosides of a second type; and
X represents a nucleoside to which a conjugate is attached.

In certain embodiments, A and B are 2'-modifications and X is a conjugate attached at the 2'-position. Thus, the motif of alternating 2'-modifications is interrupted by the conjugate. Such an oligonucleotide may, nevertheless be described as having an alternating motif.

d. Antisense Compounds

In certain embodiments, compounds of the present invention are antisense compounds. Such antisense compounds are capable of hybridizing to a target nucleic acid, resulting in at least one antisense activity. In certain embodiments, antisense compounds specifically hybridize to one or more target nucleic acid. In certain embodiments, a specifically hybridizing antisense compound has a nucleobase sequence comprising a region having sufficient complementarity to a target nucleic acid to allow hybridization and result in antisense activity and insufficient complementarity to any non-target so as to avoid or reduce non-specific hybridization to non-target nucleic acid sequences under conditions in which specific hybridization is desired (e.g., under physiological conditions for in vivo or therapeutic uses, and under conditions in which assays are performed in the case of in vitro assays). In certain embodiments, oligonucleotides are selective between a target and non-target, even though both target and non-target comprise the target sequence. In such embodiments, selectivity may result from relative accessability of the target region of one nucleic acid molecule compared to the other.

In certain embodiments, the present invention provides antisense compounds comprising oligonucleotides that are fully complementary to the target nucleic acid over the entire length of the oligonucleotide. In certain embodiments, oligonucleotides are 99% complementary to the target nucleic acid. In certain embodiments, oligonucleotides are 95% complementary to the target nucleic acid. In certain embodiments, oligonucleotides are 90% complementary to the target nucleic acid.

In certain embodiments, oligonucleotides are 85% complementary to the target nucleic acid. In certain embodiments, oligonucleotides are 80% complementary to the target nucleic acid. In certain embodiments, an antisense compound comprises a region that is fully complementary to a target nucleic acid and is at least 80% complementary to the target nucleic acid over the entire length of the oligonucleotide. In certain such embodiments, the region of full complementarity is from 6 to 14 nucleobases in length.

In certain embodiments, oligonucleotides comprise a hybridizing region and a terminal region. In certain such embodiments, the hybridizing region consists of 12-30 linked nucleosides and is fully complementary to the target nucleic acid. In certain embodiments, the hybridizing region includes one mismatch relative to the target nucleic acid. In certain embodiments, the hybridizing region includes two mismatches relative to the target nucleic acid. In certain embodiments, the hybridizing region includes three mismatches relative to the target nucleic acid. In certain embodiments, the hybridizing region includes four mismatches relative to the target nucleic acid. In certain embodiments, the terminal region consists of 1-4 terminal nucleosides. In certain embodiments, the terminal nucleosides are at the 3' end. In certain embodiments, one or more of the terminal nucleosides are not complementary to the target nucleic acid.

Antisense mechanisms include any mechanism involving the hybridization of an oligonucleotide with target nucleic acid, wherein the hybridization results in a biological effect. In certain embodiments, such hybridization results in either target nucleic acid degradation or occupancy with concomitant inhibition or stimulation of the cellular machinery involving, for example, translation, transcription, or splicing of the target nucleic acid.

One type of antisense mechanism involving degradation of target RNA is Rnase H mediated antisense. Rnase H is a cellular endonuclease which cleaves the RNA strand of an RNA:DNA duplex. It is known in the art that single-stranded antisense compounds which are "DNA-like" elicit Rnase H activity in mammalian cells. Activation of Rnase H, therefore, results in cleavage of the RNA target, thereby greatly enhancing the efficiency of DNA-like oligonucleotide-mediated inhibition of gene expression.

Antisense mechanisms also include, without limitation RNAi mechanisms, which utilize the RISC pathway. Such RNAi mechanisms include, without limitation siRNA, ssRNA and microRNA mechanisms.

In certain embodiments, antisense compounds of the present invention are RNAi compounds. In certain embodiments, antisense compounds of the present invention are ssRNA compounds. In certain embodiments, antisense compounds of the present invention are paired with a second oligonucleotide to form an siRNA. In certain such embodiments, the second oligonucleotide is also a compound of the present invention. In certain embodiments, the second oligonucleotide is any modified or unmodified oligonucleotide. In certain embodiments, the oligonucleotide of the present invention is the antisense strand in an siRNA compound. In certain embodiments, the oligonucleotide of the present invention is the sense strand in an siRNA compound.

iv. Single-Stranded RNAi Compounds

In certain embodiments, oligonucleotides of the present invention are particularly suited for use as single-stranded antisense compounds. In certain such embodiments, such oligonucleotides are single-stranded RNAi compounds. In certain embodiments, such oligonucleotides are ssRNA compounds or microRNA mimics. Certain 5'-terminal nucleosides described herein are suited for use in such single-stranded oligonucleotides. In certain embodiments, such 5'-terminal nucleosides stabilize the 5'-phosphorous moiety. In certain embodiments, 5'-terminal nucleosides of the present invention are resistant to nucleases. In certain embodiments, the motifs of the present invention are particularly suited for use in single-stranded oligonucleotides. For further description of single-stranded RNAi compounds, see, e.g., WO 2010/048585, WO 2010/048549, and PCT/US2011/033968.

Use of single-stranded RNAi compounds has been limited. In certain instances, single stranded RNAi compounds are quickly degraded and/or do not load efficiently into RISC. Design of single-stranded RNAi compounds for use in cells and/or for use in vivo presents several challenges. For example, the compound must be chemically stable, resistant to nuclease degradation, capable of entering cells, capable of loading into RISC (e.g., binding Ago1 or Ago2), capable of hybridizing with a target nucleic acid, and not toxic to cells or animals. In certain instances, a modification or motif that improves one such feature may worsen another feature, rendering a compound having such modification or motif unsuitable for use as an RNAi compound. For example, certain modifications, particularly if placed at or near the 5'-end of an oligonucleotide, may make the compound more stable and more resistant to nuclease degradation, but may also inhibit or prevent loading into RISC by blocking the interaction with RISC components, such as Ago1 or Ago2. Despite its improved stability properties, such a compound would be unsuitable for use in RNAi.

In certain instances, a single-stranded oligonucleotide comprising a 5'-phosphorous moiety is desired. For example, in certain embodiments, such 5'-phosphorous moiety is necessary or useful for RNAi compounds, particularly, single-stranded RNAi compounds. In such instances, it is further desirable to stabilize the phosphorous moiety against degradation or de-phosphorylation, which may inactivate the compound. Further, it is desirable to stabilize the entire 5'-nucleoside from degradation, which could also inactivate the compound. Thus, in certain embodiments, oligonucleotides in which both the 5'-phosphorous moiety and the 5'-nucleoside have been stabilized are desired. In certain embodiments, provided are modified nucleosides that may be placed at the 5'-end of an oligonucleotide, resulting in a stabilized phosphorous and stabilized nucleoside. In certain such embodiments, the phosphorous moiety is resistant to removal in biological systems, relative to unmodified nucleosides and/or the 5'-nucleoside is resistant to cleavage by nucleases. In certain embodiments, such nucleosides are modified at one, at two or at all three of: the 2'-position, the 5'-position, and at the phosphorous moiety. Such modified nucleosides may be incorporated at the 5'-end of an oligonucleotide.

Although certain oligonucleotides described herein have particular use as single-stranded compounds, such compounds may also be paired with a second strand to create a double-stranded compound. In such embodiments, the second strand of the double-stranded duplex may or may not also be an oligonucleotide as described herein.

In certain embodiments, oligonucleotides as described herein interact with an argonaute protein (Ago). In certain embodiments, such oligonucleotides first enter the RISC pathway by interacting with another member of the pathway (e.g., dicer). In certain embodiments, oligonucleotides first enter the RISC pathway by interacting with Ago. In certain embodiments, such interaction ultimately results in antisense activity. In certain embodiments, provided are methods of activating Ago comprising contacting Ago with an oligonucleotide. In certain embodiments, such oligonucleotides comprise a modified 5'-phosphate group. In certain embodiments, provided are methods of modulating the expression or amount of a target nucleic acid in a cell comprising contacting the cell with an oligonucleotide capable of activating Ago, ultimately resulting in cleavage of the target nucleic acid. In certain embodiments, the cell is in an animal. In certain embodiments, the cell is in vitro. In certain embodiments, the methods are performed in the presence of manganese. In certain embodiments, the manganese is endogenous. In certain embodiments, the methods are performed in the absence of magnesium. In certain embodiments, the Ago is endogenous to the cell. In certain such embodiments, the cell is in an animal. In certain embodiments, the Ago is human Ago. In certain embodiments, the Ago is Ago2. In certain embodiments, the Ago is human Ago2.

In certain embodiments, provided are oligonucleotides having motifs (nucleoside motifs and/or linkage motifs) that result in improved properties. Certain such motifs result in single-stranded oligonucleotides with improved stability and/or cellular uptake properties while retaining antisense activity. For example, oligonucleotides having an alternating nucleoside motif and seven phosphorothioate linkages at the 3'-terminal end have improved stability and activity. Similar compounds that comprise phosphorothioate linkages at each linkage have further improved stability, but are not active as RNAi compounds, presumably because the additional phosphorothioate linkages interfere with the interaction of the oligonucleotide with the RISC pathway components (e.g., with Ago). In certain embodiments, the oligonucleotides having motifs herein result in single-stranded RNAi compounds having desirable properties. In certain embodiments, such oligonucleotides may be paired with a second strand to form a double-stranded RNAi compound. In such embodiments, the second strand of such double-stranded RNAi compounds may comprise a motif as described herein, may comprise another motif of modifications or may be unmodified.

It has been shown that in certain circumstances for single-stranded RNA comprising a 5'-phosphate group has RNAi activity but has much less RNAi activity if it lacks such 5'-phosphate group. The present inventors have recognized that in certain circumstances unmodified 5'-phophate groups may be unstable (either chemically or enzymatically). Accordingly, in certain circumstances, it is desirable to modify the oligonucleotide to stabilize the 5'-phosphate. In certain embodiments, this is achieved by modifying the phosphate group. In certain embodiments, this is achieved by modifying the sugar of the 5'-terminal nucleoside. In certain embodiments, this is achieved by modifying the phosphate group and the sugar. In certain embodiments, the sugar is modified at the 5'-position, the 2'-position, or both the 5'-position and the 2'-position. As with motifs, above, in embodiments in which RNAi activity is desired, a phosphate stabilizing modification must not interfere with the ability of the oligonucleotide to interact with RISC pathway components (e.g., with Ago).

In certain embodiments, provided are oligonucleotides comprising a phosphate-stabilizing modification and a motif described herein. In certain embodiments, such oligonucleotides are useful as single-stranded RNAi compounds having desirable properties. In certain embodiments, such oligonucleotides may be paired with a second strand to form a double-stranded RNAi compound. In such embodiments, the second strand may comprise a motif as described herein, may comprise another motif of modifications or may be unmodified RNA.

In certain embodiments, provided are compounds and methods for antisense activity in a cell. In certain embodiments, the cell is in an animal. In certain embodiments, the animal is a human. In certain embodiments, provided are methods of administering a compound as described herein to an animal to modulate the amount or activity or function of one or more target nucleic acid.

In certain embodiments oligonucleotides comprise one or more motifs as described herein, but do not comprise a phosphate stabilizing modification. In certain embodiments, such oligonucleotides are useful for in vitro applications.

e. Expanded Repeat-Containing RNA

In certain embodiments, provided are compounds and methods for modulating the amount, activity or function of an expanded repeat-containing RNA. Such expanded repeat-containing RNA molecules have been associated with a number of diseases or disorders.

Certain normal wild-type RNA molecules comprise repeat regions, which, in certain instances can become expanded. In certain instances, the shorter repeat regions of wild type transcripts not associated with disease have secondary structure, making them relatively inaccessible for base pairing with a complementary nucleic acid. In contrast, the number of repeats in the expanded repeat region of an expanded repeat-containing RNA is typically at least 2 fold normal and often more (e.g., 3, 5, 10 fold, up to 100 or even more than 1000 fold). This expansion increases the likelihood that part of the repeat is, at least temporarily, more accessible to base pairing with a complementary nucleic acid molecule, relative to the wild type allele. Thus, even though certain compounds described herein comprise oligonucleotides complementary to a repeat sequence present in both wild-type and repeat-expanded transcripts, in certain embodiments, such compounds selectively hybridize to the disease-associated repeat-expanded transcript. In certain embodiments, such compounds as described herein are more selective and potent than prior compounds targeting repeat-expanded transcripts, see, e.g. U.S. Ser. No. 61/302,450; U.S. Ser. No. 61/405,157; PCT/US2011/024099; U.S. Ser. No. 61/302,454; U.S. Ser. No. 61/302,482; U.S. Ser. No. 61/405,130; and PCT/US2011/024019, which are herein incorporated by reference in the entirety. Such selectivity is beneficial for treating diseases associated with expanded repeat-containing RNA irrespective of the mechanism of reduction of the aberrant transcript.

Certain expanded repeat-containing RNA have been referred to in the art as "gain-of-function RNAs" for their ability to sequester hnRNPs and impair the normal action of RNA processing in the nucleus (see e.g., Cooper, T. (2009) Cell 136, 777-793; O'Rourke, J R (2009) J. Biol. Chem. 284 (12), 7419-7423, which are herein incorporated by reference in the entirety). Several disease states are associated with expanded repeat-containing RNA, some of which only occur once a threshold number of repeats within the expanded repeat-containing RNA is reached. In certain embodiments, provided herein are methods of reducing the activity, function, or amount of an expanded repeat-containing RNA having at least 10, 15, 20, 25, 30, 35, 40, 45, 50, 55, 60, 80, 90, 100, 200, 300, 400, 500, 1000, or more than 1000 copies of a repeating nucleotide unit.

In certain embodiments, provided herein compounds and methods for targeting or treating an expanded repeat-containing RNA, wherein the repeat may be CAG, CUG, and CCUG. In certain embodiments, provided herein compounds and methods for targeting or treating any of the disorders in the following non limiting table, which may be associated with a CAG, CUG, or CCUG repeat:

| DISEASE | REPEAT | AFFECTED GENE | COPY NUMBER (NORMAL) | COPY NUMBER (DISEASED) | Reference |
|---|---|---|---|---|---|
| Atrophin 1 (DRPLA) | CAG | ATN1/DRPLA | 7 to 34 | 49-93 | Nat. Genet. 10: 99, 1995 |
| Huntington disease | CAG | Htt | <28 | >36 | Lancet 369: 220, 2007 |
| Huntington disease-like 2 (HDL2) | CAG | junctophilin-3 (JPH3) | 6 to 28 | 144 to 57 | Nat. Clin Prac Neurol. 3: 517, 2007 |
| Spinal and bulbar muscular atrophy/Kennedy disease | CAG | Androgen receptor (AR) (X-linked) | 10 to 36 | 38 to 62 | Nature 352: 77, 1991 |
| Spinocerebellar ataxia | CAG | ataxin-1 (ATXN1) | 6 to 35 | 49 to 88 | NCBI/OMIM |
| Spinocerebellar ataxia 12 | CAG | protein phosphatase PP2A (PPP2R2B) | 9 to 28 | 55 to 78 | Brain Res Bull. 56: 397, 2001 |
| | | | 7 to 28 | 66 to 78 | Wikipedia |

-continued

| DISEASE | REPEAT | AFFECTED GENE | COPY NUMBER (NORMAL) | COPY NUMBER (DISEASED) | Reference |
|---|---|---|---|---|---|
| Spinocerebellar ataxia 17/Huntington disease-like 4 (HDL4) | CAG | TATA box-binding protein (TBP) | 25 to 42 | 47 to 63 | Eur. J. Hum. Genet. 9: 160, 2001 (NCBI/OMIM) |
| Spinocerebellar ataxia 2 | CAG | ATXN2 | 17 to 29 | 37 to 50 | Nat. Genet. 14: 285, 1996 (NCBI/OMIM) |
| Spinocerebellar ataxia 3 (Machado-Joseph disease) | CAG | ATXN3 | 15 to 34 | 35 to 59 | Nat. Genet. 14: 277, 1996(NCBI/OMIM) |
|  |  |  | 14 to 32 | 33 to 77 | Wikipedia |
|  |  |  | 10 to 51 | 55-87 | Human Mol. Genet. 17: 2071, 2008 (NCBI/OMIM) |
|  |  |  | 12 to 40 | 55 to 86 | Wikipedia |
| Spinocerebellar ataxia 6 | CAG | CACNA1A | 4 to 18 | 21 to 30 | Wikipedia |
|  |  |  | 5 to 20 | 21 to 25 | Am. J. Hum. Genet. 61: 336, 1997 (NCBI/OMIM) |
| Spinocerebellar ataxia 7/OPCA3 | CAG | ATXN7 | 7 to 17 | 38-130 | Nat. Genet. 17: 65, 1997 (NCBI/OMIM) |
| Ataxin 8 opposite strand (ATXN8OS) | CUG with or without interruptions | SCA8/ataxin 8 | 16-37 | 107-127 | Nat. Genet 21: 379, 1999 (NCBI/OMIM) |
| Huntington disease-like 2 (HDL2) | CAG/CUG | junctophilin-3 (JPH3) | 6 to 28 | 44 to 57 | Nat. Clin Prac Neurol. 3: 517, 2007 |
| Myotonic dystrophy (DM1) | CUG | DMPK | 5 TO 35 | 80 TO >2500 | Harper, Myotonic Dystrophy (Saunders, London, ed.3, 2001) |
|  |  |  |  | 50 to >3500 | Annu. Rev. Neurosci. 29: 259, 2006 |
|  |  |  | 5 to 37 | >50 | EMBO J. 19: 4439, 2000 |
|  |  |  |  | 50 to >2000 | Curr Opin Neurol. 20: 572, 2007 |
| DM2 | CCUG | zinc finger protein-9 |  | 75 to 11,000 | Science 293: 864, 2001 (NCBI/OMIM) |
| Spinocerebellar ataxia 8 | CUG | SCA8 |  | 74 to >1300 | Nat. Genet. 21: 379, 1999 |

In certain embodiments, compounds described herein are used to alter the activity or amount of expanded repeat-containing RNA and/or associated protein. In certain embodiments, compounds described herein are mutant selective. Accordingly, certain such compounds reduce the amount or activity of expanded repeat-containing RNA to a greater extent than they reduce the amount or activity of the corresponding wild-type RNA.

In certain embodiments, oligonucleotides described herein have a sequence comprising a hybridizing region having one mismatch relative to the target repeat. In certain embodiments, oligonucleotides comprise a hybridizing region having two mismatches relative to the target repeat. In certain embodiments, oligonucleotides comprise a hybridizing region having three mismatches relative to the target repeat. In certain embodiments, oligonucleotides comprise a hybridizing region having four or more mismatches relative to the target repeat. In certain embodiment, at least one mismatch is at position 7, 8, 9, 10, or 11, counting from the 5'-end of the hybridizing region. In certain embodiments, at least one mismatch is at position 9, 10, 11, 12, or 13, counting from the 3'-end of the hybridizing region. In certain embodiment, at least one mismatch is at position 7, 8, 9, 10, or 11, counting from the 5'-end of the hybridizing region and position 9, 10, 11, 12, or 13, counting from the 3'-end of the hybridizing region. In certain embodiment, at least one mismatch is at position 7, 8, 9, 10, or 11, counting from the 5'-terminal nucleoside and position 9, 10, 11, 12, or 13, counting from the 3'-end terminal nucleoside. In certain embodiments, such mismatches may result in the resulting duplex being processed differently by the cell. For example, such mismatched duplexes resemble microRNA, rather than siRNA. Thus, in certain instances, such molecules track the microRNA pathway, ending in sequestration, rather than siRNA-like cleavage. In certain circumstances, utilization of the microRNA pathway may result in greater selectivity for mutant over wild-type.

In certain embodiments, provided are methods of modulating the expression or amount of a target nucleic acid in a cell comprising contacting the cell with an oligonucleotide having a sequence comprising a hybridizing region having one or more mismatches relative to the target and capable of activating Ago. In certain embodiments, although the oligonucleotide activates Ago, the oligonucleotide's mismatches may prevent Ago from cleaving target mRNA. In certain embodiments, although the oligonucleotide activates Ago, the oligonucleotide's mismatches may disrupt AGO-mediated cleavage of mRNA and may result in an oligonucleotide-AGO complex that blocks ribosomal activity and inhibits protein translation. In certain embodiments, although the oligonucleotide interacts with Ago, the oligonucleotide's mismatches may prevent translation of the mRNA. In certain embodiments, oligonucleotides having a sequence comprising a hybridizing region having one or more mismatches relative to the target may prevent translation of the target mRNA. In certain embodiments, oligonucleotides having a sequence comprising a hybridizing region having one or more mismatches relative to the target may prevent translation of a mutant mRNA containing one or more nucleotide repeats.

In certain embodiments, a mutant allele may have more nucleotide repeats than a wild type allele. In certain embodiments, the expanded number of nucleotide repeats offers more binding sites for complementary oligonucleotides. For example, a mutant allele may have many more repeats than the wild type allele and the mutant allele may therefore bind more complementary oligonucleotides than the wild type allele. In certain embodiments, for example, mutant HTT mRNA may have 69 or more repeats whereas a wild-type HTT mRNA may have 17 repeats. A mutant HTT mRNA having 69 repeats can bind up to 9-10 twenty base long oligomers whereas the wild type HIT mRNA may only bind one or two twenty base long oligomers. In certain embodiments, the binding of multiple oligomers within a mutant repeat region can produce cooperative inhibition and produce selectivite inhibition of the mutant allele compared to the wild type allele.

In certain embodiments, the expanded number of nucleotide repeats present in mutant alleles may form structures that differ from the structure of the wild-type allele. In certain embodiments, structure of a mutant allele may facilitate recognition by an oligonucleotide. In certain embodiments, an oligomeric compound may more readily interact with a mutant allele as compared to a wild-type allele. For example, in certain embodiments, a mutant HTT mRNA having 69 repeats may comprise a structure that facilitates interaction with an oligomeric compound, whereas a wild type HIT mRNA may comprise a structure that does not facilitate interaction with said oligomeric compound. In certain such instances, certain oligomeric compounds may selectively reduce expression of a mutant allele compared to a wild-type allele.

C. Certain Pharmaceutical Compositions

In certain embodiments, provided herein are pharmaceutical compositions comprising one or more antisense compound. In certain embodiments, such pharmaceutical composition comprises a suitable pharmaceutically acceptable diluent or carrier. In certain embodiments, a pharmaceutical composition comprises a sterile saline solution and one or more antisense compound. In certain embodiments, such pharmaceutical composition consists of a sterile saline solution and one or more antisense compound. In certain embodiments, the sterile saline is pharmaceutical grade saline. In certain embodiments, a pharmaceutical composition comprises one or more antisense compound and sterile water. In certain embodiments, a pharmaceutical composition consists of one or more antisense compound and sterile water. In certain embodiments, the sterile saline is pharmaceutical grade water. In certain embodiments, a pharmaceutical composition comprises one or more antisense compound and phosphate-buffered saline (PBS). In certain embodiments, a pharmaceutical composition consists of one or more antisense compound and sterile phosphate-buffered saline (PBS). In certain embodiments, the sterile saline is pharmaceutical grade PBS.

In certain embodiments, antisense compounds may be admixed with pharmaceutically acceptable active and/or inert substances for the preparation of pharmaceutical compositions or formulations. Compositions and methods for the formulation of pharmaceutical compositions depend on a number of criteria, including, but not limited to, route of administration, extent of disease, or dose to be administered.

Pharmaceutical compositions comprising antisense compounds encompass any pharmaceutically acceptable salts, esters, or salts of such esters. In certain embodiments, pharmaceutical compositions comprising antisense compounds comprise one or more oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an oligonucleotide which are cleaved by endogenous nucleases within the body, to form the active antisense oligonucleotide.

Lipid moieties have been used in nucleic acid therapies in a variety of methods. In certain such methods, the nucleic acid is introduced into preformed liposomes or lipoplexes made of mixtures of cationic lipids and neutral lipids. In certain methods, DNA complexes with mono- or polycationic lipids are formed without the presence of a neutral lipid. In certain embodiments, a lipid moiety is selected to increase distribution of a pharmaceutical agent to a particular cell or tissue. In certain embodiments, a lipid moiety is selected to increase distribution of a pharmaceutical agent to fat tissue. In certain embodiments, a lipid moiety is selected to increase distribution of a pharmaceutical agent to muscle tissue.

In certain embodiments, pharmaceutical compositions provided herein comprise one or more modified oligonucleotides and one or more excipients. In certain such embodiments, excipients are selected from water, salt solutions, alcohol, polyethylene glycols, gelatin, lactose, amylase, magnesium stearate, talc, silicic acid, viscous paraffin, hydroxymethylcellulose and polyvinylpyrrolidone.

In certain embodiments, a pharmaceutical composition provided herein comprises a delivery system. Examples of delivery systems include, but are not limited to, liposomes and emulsions. Certain delivery systems are useful for preparing certain pharmaceutical compositions including those comprising hydrophobic compounds. In certain embodiments, certain organic solvents such as dimethylsulfoxide are used.

In certain embodiments, a pharmaceutical composition provided herein comprises one or more tissue-specific delivery molecules designed to deliver the one or more pharmaceutical agents as described herein to specific tissues or cell types. For example, in certain embodiments, pharmaceutical compositions include liposomes coated with a tissue-specific antibody.

In certain embodiments, a pharmaceutical composition provided herein comprises a co-solvent system. Certain of such co-solvent systems comprise, for example, benzyl alcohol, a nonpolar surfactant, a water-miscible organic polymer, and an aqueous phase. In certain embodiments, such co-solvent systems are used for hydrophobic compounds. A non-limiting example of such a co-solvent system is the VPD co-solvent system, which is a solution of absolute ethanol comprising 3% w/v benzyl alcohol, 8% w/v of the nonpolar surfactant Polysorbate 80™ and 65% w/v polyethylene glycol 300. The proportions of such co-solvent systems may be varied considerably without significantly altering their solubility and toxicity characteristics. Furthermore, the identity of co-solvent components may be varied: for example, other surfactants may be used instead of Polysorbate 80™; the fraction size of polyethylene glycol may be varied; other biocompatible polymers may replace polyethylene glycol, e.g., polyvinyl pyrrolidone; and other sugars or polysaccharides may substitute for dextrose.

In certain embodiments, a pharmaceutical composition provided herein is prepared for oral administration. In certain embodiments, pharmaceutical compositions are prepared for buccal administration.

In certain embodiments, a pharmaceutical composition is prepared for administration by injection or infusion (e.g., intravenous, subcutaneous, intramuscular, intrathecal, intracerebroventricular etc.). In certain of such embodiments, a pharmaceutical composition comprises a carrier and is formulated in aqueous solution, such as water or physiologically compatible buffers such as Hanks's solution, Ringer's solution, or physiological saline buffer. In certain embodiments, other ingredients are included (e.g., ingredients that aid in solubility or serve as preservatives). In certain embodiments, injectable suspensions are prepared using appropriate liquid carriers, suspending agents and the like. Certain pharmaceutical compositions for injection are presented in unit dosage form, e.g., in ampoules or in multi-dose containers. Certain pharmaceutical compositions for injection are suspensions, solutions or emulsions in oily or aqueous vehicles, and may contain formulatory agents such as suspending, stabilizing and/or dispersing agents. Certain solvents suitable for use in pharmaceutical compositions for injection include, but are not limited to, lipophilic solvents and fatty oils, such as sesame oil, synthetic fatty acid esters, such as ethyl oleate or triglycerides, and liposomes. Aqueous injection suspensions may contain substances that increase the viscosity of the suspension, such as sodium carboxymethyl cellulose, sorbitol, or dextran. Optionally, such suspensions may also contain suitable stabilizers or agents that increase the solubility of the pharmaceutical agents to allow for the preparation of highly concentrated solutions.

In certain embodiments, a pharmaceutical composition is prepared for transmucosal administration. In certain of such embodiments penetrants appropriate to the barrier to be permeated are used in the formulation. Such penetrants are generally known in the art.

In certain embodiments, a pharmaceutical composition provided herein comprises an oligonucleotide in a therapeutically effective amount. In certain embodiments, the therapeutically effective amount is sufficient to prevent, alleviate or ameliorate symptoms of a disease or to prolong the survival of the subject being treated.

In certain embodiments, one or more modified oligonucleotide provided herein is formulated as a prodrug. In certain embodiments, upon in vivo administration, a prodrug is chemically converted to the biologically, pharmaceutically or therapeutically more active form of an oligonucleotide. In certain embodiments, prodrugs are useful because they are easier to administer than the corresponding active form. For example, in certain instances, a prodrug may be more bioavailable (e.g., through oral administration) than is the corresponding active form. In certain instances, a prodrug may have improved solubility compared to the corresponding active form. In certain embodiments, prodrugs are less water soluble than the corresponding active form. In certain instances, such prodrugs possess superior transmittal across cell membranes, where water solubility is detrimental to mobility. In certain embodiments, a prodrug is an ester. In certain such embodiments, the ester is metabolically hydrolyzed to carboxylic acid upon administration. In certain instances the carboxylic acid containing compound is the corresponding active form. In certain embodiments, a prodrug comprises a short peptide (polyaminoacid) bound to an acid group. In certain of such embodiments, the peptide is cleaved upon administration to form the corresponding active form.

In certain embodiments, provided herein are compositions and methods for reducing the amount or activity of a target nucleic acid in a cell. In certain embodiments, the cell is in an animal. In certain embodiments, the animal is a mammal. In certain embodiments, the animal is a rodent. In certain embodiments, the animal is a primate. In certain embodiments, the animal is a non-human primate. In certain embodiments, the animal is a human.

In certain embodiments, provided herein are methods of administering a pharmaceutical composition comprising an oligonucleotide as described herein to an animal. Suitable administration routes include, but are not limited to, oral, rectal, transmucosal, intestinal, enteral, topical, suppository, through inhalation, intrathecal, intracerebroventricular, intraperitoneal, intranasal, intraocular, intratumoral, and parenteral (e.g., intravenous, intramuscular, intramedullary, and subcutaneous).

D. Certain Uses and Routes of Administration

In certain embodiments, provided herein are methods of contacting a cell with an oligonucleotide described herein. In certain embodiments, the cell is in vitro. In certain embodiments, the cell is in an animal (e.g., rodent, primate, monkey or human). In certain embodiments, antisense activity is detected.

In certain embodiments, the disease is any of atrophin 1 (DRPLA), Huntington's Disease, Huntington disease-like 2 (HDL2), spinal and bulbar muscular atrophy, Kennedy disease, spinocerebellar ataxia 1, spinocerebellar ataxia 12, spinocerebellar ataxia 17, Huntington disease-like 4 (HDL4), spinocerebellar ataxia 2, spinocerebellar ataxia 3, Machado-Joseph disease, spinocerebellar ataxia 6, spinocerebellar ataxia 7 (OPCA3), ataxin 8 opposite strand (ATXN8OS), myotonic dystrophy (DM1), DM2, and spinocerebellar ataxia 8.

In certain embodiments, compounds as described herein are administered to an animal (e.g., a human) to provide a therapeutic effect. Certain diseases or disorders have been identified to be associated with expanded repeat-containing RNA. Any such disease or disorder might be treated with compounds as described herein. In certain embodiments, the disease is selected from among: ataxin 8, atrophin 1, fragile X syndrome, Friedrich's ataxia, Huntington's disease, Huntington's disease-like 2, myotonic dystrophy, spinal and bulbar muscular atrophy, and spinocerebellar ataxia. In certain embodiments, the disease is Huntington's disease. In certain embodiments, the disease is myotonic dystrophy. In certain embodiments, the myotonic dystrophy is myotonic dystrophy type 1. In certain embodiments, the myotonic dystrophy is myotonic dystrophy type 2. In certain embodiments, the disease is spinocerebellar ataxia. In certain embodiments, the spinocerebellar ataxia is spinocerebellar ataxia 10.

In certain embodiments, pharmaceutical compositions as described herein are administered to a subject. In certain embodiments, such pharmaceutical compositions are administered by injection. In certain embodiments, such pharmaceutical compositions are administered by infusion.

In certain embodiments, pharmaceutical compositions are administered by injection or infusion into the CSF. In certain such embodiments, pharmaceutical compositions are administered by direct injection or infusion into the spine. In certain embodiments, pharmaceutical compositions are administered by injection or infusion into the brain. In certain embodiments, pharmaceutical compositions are administered by intrathecal injection or infusion rather than into the spinal cord tissue itself. Without being limited as to theory, in certain embodiments, the antisense compound released into the surrounding CSF and may penetrate into the spinal cord parenchyma. An additional advantage of intrathecal delivery is that the intrathecal route mimics lumbar puncture administration (i.e., spinal tap) already in routine use in humans.

In certain embodiments, pharmaceutical compositions are administered by intracerebroventricular (ICV) injection or infusion. Intracerebroventricular or intraventricular delivery of a pharmaceutical composition comprising one or more oligonucleotide may be performed in any one or more of the brain's ventricles, which are filled with cerebrospinal fluid (CSF). CSF is a clear fluid that fills the ventricles, is present in the subarachnoid space, and surrounds the brain and spinal cord. CSF is produced by the choroid plexuses and via the weeping or transmission of tissue fluid by the brain into the ventricles. The choroid plexus is a structure lining the floor of the lateral ventricle and the roof of the third and fourth ventricles. Certain studies have indicated that these structures are capable of producing 400-600 ccs of fluid per day consistent with an amount to fill the central nervous system spaces four times in a day. In adult humans, the volume of this fluid has been calculated to be from 125 to 150 ml (4-5 oz). The CSF is in continuous formation, circulation and absorption. Certain studies have indicated that approximately 430 to 450 ml (nearly 2 cups) of CSF may be produced every day. Certain calculations estimate that production equals approximately 0.35 ml per minute in adults and 0.15 per minute in infant humans. The choroid plexuses of the lateral ventricles produce the majority of CSF. It flows through the foramina of Monro into the third ventricle where it is added to by production from the third ventricle and continues down through the aqueduct of Sylvius to the fourth ventricle. The fourth ventricle adds more CSF; the fluid then travels into the subarachnoid space through the foramina of Magendie and Luschka. It then circulates throughout the base of the brain, down around the spinal cord and upward over the cerebral hemispheres. The CSF empties into the blood via the arachnoid villi and intracranial vascular sinuses.

In certain embodiments, such pharmaceutical compositions are administered systemically. In certain embodiments, pharmaceutical compositions are administered subcutaneously. In certain embodiments, pharmaceutical compositions are administered intravenously. In certain embodiments, pharmaceutical compositions are administered by intramuscular injection.

In certain embodiments, pharmaceutical compositions are administered both directly to the CSF (e.g., IT and/or ICV injection and/or infusion) and systemically. In certain such embodiments, compounds as described herein have one or more desirable properties making them suitable for such administration. Drug design typically requires a balance of several variables, including, but not limited to: potency, toxicity, stability, tissue distribution, convenience, and cost of a candidate compound. Such balancing is influenced by a number of factors, including the severity and typical duration of the disease treated. For example, greater drug-related toxicity is tolerated for use in treating acute lethal diseases than chronic sub-lethal diseases. In certain embodiments, compounds as described herein will have one or more improved properties compared to similar compounds that lack certain features as described herein. For example, compared to other compounds, the compounds as described herein, may, in certain embodiments, have improved potency or may have similar potency but reduced toxicity and consequently improved therapeutic index. In certain embodiments, compounds as described herein may have improved pharmecokinetics or distribution to a particular desired target tissue.

In certain embodiments, oligonucleotides as described herein are used in cells in vitro. In certain such embodiments, such uses are to identify and/or study expanded repeat-containing nucleic acids and mechanisms surrounding them and associated diseases.

Nonlimiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Although the sequence listing accompanying this filing identifies each sequence as either "RNA" or "DNA" as required, in reality, those sequences may be modified with any combination of chemical modifications. One of skill in the art will readily appreciate that such designation as "RNA" or "DNA" to describe modified oligonucleotides is, in certain instances, arbitrary. For example, an oligonucleotide comprising a nucleoside comprising a 2'-OH sugar moiety and a thymine base could be described as a DNA having a modified sugar (2'-OH for the natural 2'-H of DNA) or as an RNA having a modified base (thymine (methylated uracil) for natural uracil of RNA).

Accordingly, nucleic acid sequences provided herein, including, but not limited to those in the sequence listing, are intended to encompass nucleic acids containing any combination of natural or modified RNA and/or DNA, including, but not limited to such nucleic acids having modified nucleobases. By way of further example and without limitation, an oligonucleotide having the nucleobase sequence "ATCGATCG" encompasses any oligonucleotides having such nucleobase sequence, whether modified or unmodified, including, but not limited to, such compounds comprising RNA bases, such as those having sequence "AUCGAUCG" and those having some DNA bases and some RNA bases such as "AUCGATCG" and oligonucleotides having other modified bases, such as "ATmeCGAUCG," wherein $^{me}C$ indicates a cytosine base comprising a methyl group at the 5-position.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the patents, applications, printed publications, and other pub-

Example 1

Modified Single Stranded RNAs (ssRNAs) Targeting Huntingtin (HTT) CAG Repeat Region ssRNAs, siRNAs and Gapmers A series of modified single strand RNAs (ssRNAs) were designed and tested for their ability to selectively inhibit mutant (mut) HTT protein expression levels in patient-derived fibroblast cell line GM04281 (69 CAG repeats mutant/17 CAG repeats wild-type). The potency and selectivity of the modified ssRNAs were evaluated and compared to the gapmers and the double stranded small interfering RNAs (siRNAs).

The gapmers comprising a 5-10-5 motif were prepared using the procedures as described above and the siRNAs were purchased from Integrated DNA Technologies (IDT, Coralville, Iowa).

The modified ssRNAs, siRNAs and gapmers are described in Table 1. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $PO(OH)_2(CH=CH-)$. A "Po" at the 5'-end indicates a 5'-phosphate group, $(PO(OH)_2-)$. Nucleosides without a subscript are β-D-2'-deoxyribonucleosides. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. $^{me}C$ indicates a 5-methyl cytosine nucleoside. Underlined nucleosides indicate the mismatch position.

Cell Culture and Transfection

The patient-derived fibroblast cell line GM04281 was obtained from the Coriell Institute (Camden, N.J.). Cells were maintained at 37° C. and 5% $CO_2$ in Minimal Essential Media Eagle (MEM) (Sigma, M4655) supplemented with 10% heat inactivated fetal bovine serum (Sigma) and 0.5% MEM nonessential amino acids (Sigma). Cells were plated at a density of 60,000 cells per well and transfected using lipid RNAiMAX (Invitrogen) with 0.2, 0.6, 1.8, 5.6, 16.7, 50 and 100 nM concentrations of ssRNAs, siRNAs or gapmers. Typically 4 μL of lipid per well is used for transfection at 100 nM in accordance to manufacturer's protocol. Media containing RNA and lipid are mixed and allowed to sit for 20 minutes for complex formation, and the lower doses are obtained by way of serial dilution at 1:2 or 1:3-fold. Media was exchanged 1 day after transfection with fresh supplemented MEM. Cells were washed with phosphate-buffered saline and harvested 4 days after transfection for protein analysis.

Analysis of HTT Expression

HTT protein was analyzed by western blot analysis. Cells were harvested with trypsin-EDTA solution (Invitrogen) and lysed. The protein concentration in each sample was quantified by the micro bicinchoninic acid (micro-BCA) assay (Thermo Scientific). SDS-PAGE (separating gel: 5% acrylamide-bisacrylamide [50:1], 450 mM Tris-acetate pH 8.8; stacking gel: 4% acrylamide-bisacrylamide [50:1], 150 mM Tris-acetate pH 6.8) was used to separate wild-type and mutant HTT proteins. Gels were run at 30 mA per gel for 5 h in Novex Tris-acetate SDS running buffer (Invitrogen). For separation of HTT variants containing shorter CAG repeats, gels were run for 6-7 h. The electrophoresis apparatus was placed in a 15° C. water bath to prevent overheating. In parallel with analysis for HTT expression, samples were analyzed for β-actin expression by SDS-PAGE (7.5% acrylamide precast gels; Bio-Rad) to ensure even loading of protein in all lanes. These gels were run at 80 V for 15 min followed by 100 V for 1 h in 1×TGS buffer (Bio-Rad).

After electrophoresis, proteins were transferred to membrane (Hybond-C Extra; GE Healthcare BioSciences). Primary antibodies specific for HTT (MAB2166, Chemicon) and β-actin (Sigma) proteins were obtained and used at 1:10000 dilutions. HRP-conjugated anti-mouse secondary antibody (1:10000, Jackson ImmunoResearch Laboratories) was used for visualizing proteins using SuperSignal West Pico Chemiluminescent Substrate (Thermo Scientific). Protein bands were quantified using ImageJ software (Rasband, W. S., ImageJ, U.S. National Institutes of Health, Bethesda, Md., USA, http://rsb.info.nih.gov/ij/, 1997-2007).

Analysis of $IC_{50}$'s

The half maximal inhibitory concentration ($IC_{50}$) of each oligonucleotide is presented in Table 2 and was calculated by plotting the concentrations of oligonucleotides used versus the percent inhibition of HTT protein expression achieved at each concentration, and noting the concentration of oligonucleotide at which 50% inhibition of HTT protein expression was achieved compared to the control. The $IC_{50}$ at which each oligonucleotide inhibits the mutant HTT protein expression is denoted as 'mut $IC_{50}$'. The $IC_{50}$ at which each oligonucleotide inhibits the wild-type HTT protein expression is denoted as 'wt $IC_{50}$'. Selectivity was calculated by dividing the $IC_{50}$ for inhibition of the wild-type HTT versus the $IC_{50}$ for inhibiting expression of the mutant HTT protein.

ISIS 387241, ISIS 387898, and ISIS 387916 were included in the study as benchmark oligonucleotides against which only the potency (not selectivity) of the modified ssRNAs targeting HTT CAG repeat region could be compared. These benchmark oligonucleotides are complementary to sequences within HTT mRNA but outside of the CAG repeat region and therefore, are not expected to be selective against mutant HTT.

The modified ssRNAs with an asterisk (*) were tested in an independent assay and their $IC_{50}$'s are presented below. As illustrated in Table 2, treatment with modified ssRNAs comprising a single mis-match and a 5'-vinylphosphonate (ISIS 537775 or ISIS 537786) or a 5'-phosphate (ISIS 553822) selectively reduced the mutant HTT protein expression levels in a similar manner as compared to the unmodified siRNAs (A01). Fully complementary modified ssRNAs (ISIS 537787 or ISIS 553819) showed comparable potency with a significant increase in the selectivity as compared to siRNA (A02). While ISIS 537786 showed moderate potency in reducing mutant HTT protein expression levels, all modified ssRNAs presented in Table 2 showed either comparable or significant improvement in potency comparing to the gapmers. The data presented in Table 2 demonstrated that the potency and selectivity for inhibition of mutant versus wild-type HTT protein expression can be achieved with modified ssRNAs.

TABLE 1

Modified ssRNAs targeting HTT CAG repeat region

| RNA | ISIS NO. | Sequence | Mismatch position counted from 5'-end | SEQ ID NO |
|---|---|---|---|---|
| ss | 537775 | 5'-Pv-$T_{es}C_{fs}U_{m}G_{fs}C_{m}U_{fs}G_{m}C_{fs}\underline{A}_{m}G_{fs}C_{m}U_{fs}G_{m}$ $C_{fs}U_{ms}Gf_{s}C_{ms}U_{fs}G_{ms}A_{es}A_{e}$-3' | 9 | 1 |
| ss | 553822* | 5'-Po-$T_{es}C_{fs}U_{m}G_{fs}C_{m}U_{fs}G_{m}C_{fs}\underline{A}_{m}G_{fs}C_{m}U_{fs}G_{m}$ $C_{fs}U_{ms}G_{fs}C_{ms}U_{fs}G_{ms}A_{es}A_{e}$-3' | 9 | 1 |
| ss | 537786 | 5'-Pv-$T_{es}C_{fs}U_{m}G_{fs}C_{m}U_{fs}G_{m}C_{fs}U_{m}\underline{A}_{fs}C_{m}U_{fs}G_{m}$ $C_{fs}U_{ms}G_{fs}C_{ms}U_{fs}G_{ms}A_{es}A_{e}$-3' | 10 | 2 |
| si | A01 | 5'-GCUGCUGC<u>A</u>GCUGCUGCUGTT-3' <br> 3'-TTCGACGAC<u>G</u>UCGACGACGAC-5' | 9 <br> 11 | 3 <br> 4 |
| si | A02 | 5'-GCUGCUGCUGCUGCUGCUGTT-3' <br> 3'-TTCGACGACGACGACGACGAC-5' | Fully complementary | 5 <br> 6 |
| ss | 537787 | 5'-Pv-$T_{es}C_{fs}U_{m}G_{fs}C_{m}U_{fs}G_{m}C_{fs}U_{m}G_{fs}C_{m}U_{fs}G_{m}$ $C_{fs}U_{ms}G_{fs}C_{ms}U_{fs}G_{ms}A_{es}A_{e}$-3' | Fully complementary | 7 |
| ss | 553819* | 5'-Po-$T_{es}C_{fs}U_{m}G_{fs}C_{m}U_{fs}G_{m}C_{fs}U_{m}G_{fs}C_{m}U_{fs}G_{m}$ $C_{fs}U_{ms}G_{fs}C_{ms}U_{fs}G_{ms}A_{es}A_{e}$-3' | Fully complementary | 7 |
| 5-10-5 Gapmer | 387241 | 5'-$T_{es}T_{es}{}^{me}C_{es}{}^{me}C_{es}T_{es}G_{s}G_{s}A_{s}A_{s}{}^{me}C_{s}T_{s}$ $G_{s}T_{s}{}^{me}C_{s}{}^{me}C_{es}{}^{me}C_{es}T_{es}{}^{me}C_{es}{}^{me}C_{e}$-3' | — | 8 |
| 5-10-5 Gapmer | 387898 | 5'-${}^{me}C_{es}T_{es}{}^{me}C_{es}G_{es}A_{es}{}^{me}C_{s}T_{s}A_{s}A_{s}A_{s}G_{s}{}^{me}C_{s}$ $A_{s}G_{s}G_{s}A_{es}T_{es}T_{es}T_{es}{}^{me}C_{e}$-3' | — | 9 |
| 5-10-5 Gapmer | 387916 | 5'-$T_{es}{}^{me}C_{es}T_{es}{}^{me}C_{es}T_{es}A_{s}T_{s}T_{s}G_{s}{}^{me}C_{s}A_{s}{}^{me}C_{s}$ $A_{s}T_{s}T_{s}{}^{me}C_{es}{}^{me}C_{es}A_{es}A_{es}G_{e}$-3' | — | 10 |

TABLE 2

Comparison of inhibition of HTT protein expression levels and selectivity of modified ssRNAs with unmodified siRNAs and gapmers targeting HTT CAG repeat region

| RNA | ISIS NO. | mut IC$_{50}$ (nM) | wt IC$_{50}$ (nM) | Mismatch position counted from 5'-end | Selectivity (mut vs wt) | 5'-Chemistry |
|---|---|---|---|---|---|---|
| ss | 537775 | 3.2 | 91 | 9 | 28 | (E)-vinyl phosphonate |
| ss | 553822* | 2.7 | 24.7 | 9 | 9.1 | phosphate |
| ss | 537786 | 22.3 | >100 | 10 | >4.5 | (E)-vinyl phosphonate |
| si | A01 | 3.2 | >100 | 9 | >31 | — |
| si | A02 | 5 | 13 | Fully Complementary | 3 | — |
| ss | 537787 | 8 | >100 | Fully Complementary | >12 | (E)-vinyl phosphonate |
| ss | 553819* | 2 | 30 | Fully Complementary | 15 | phosphate |
| 5-10-5 Gapmer | 387241 | 9.1 | 15.5 | — | 1.7 | OH |
| 5-10-5 Gapmer | 387898 | 5.8 | 7.1 | — | 1.2 | OH |
| 5-10-5 Gapmer | 387916 | 5.7 | 10.3 | — | 1.8 | OH |

Example 2

Modified Single Stranded RNAs (ssRNAs) Targeting Ataxin-3 (ATXN-3) CAG Repeat Region The modified ssRNAs from Table 1, ISIS 537775, ISIS 537786, and ISIS 537787 were selected and tested for their ability to selectively inhibit mutant ATXN-3 protein expression levels. The modified ssRNAs were tested in the GM06151 cell line (74 CAG repeats mutant/24 CAG repeats wild-type). Cultured GM06151 cells at a density of 60,000 cells per well were transfected using lipid RNAiMAX (Invitrogen) with 0.2, 0.6, 1.8. 5.6, 16.7, 50 and 100 nM concentrations of ssRNAs. Typically 4 µL of lipid per well is used for transfection at 100 nM in accordance to manufacturer's protocol. Media containing RNA and lipid are mixed and allowed to sit for 20 minutes for complex formation, and the lower doses are obtained by way of serial dilution at 1:2 or 1:3-fold. Media was exchanged 1 day after transfection with fresh supplemented MEM. Cells were washed with phosphate-buffered saline and harvested 4 days after transfection for protein analysis.

ATXN-3 protein expression levels were analyzed and the IC$_{50}$ was calculated using methods as described previously. The IC$_{50}$ at which each oligonucleotide inhibits the mutant ATXN-3 protein expression is denoted as 'mut IC$_{50}$'. The IC$_{50}$ at which each oligonucleotide inhibits the wild-type ATXN-3 protein expression is denoted as 'wt IC$_{50}$'. Selectivity was calculated by dividing the $IC_{50}$ for inhibition of the wild-type ATXN-3 versus the $IC_{50}$ for inhibiting expression of the mutant ATXV-3 protein and the results are presented below.

As illustrated in Table 3, ISIS 537775 contained a mismatch at position 9, was the most potent and selective compound with an $IC_{50}$ of 8.7 nM and 3-fold selectivity compared to its counterparts. ISIS 537786 contained a mismatch at position 10 was less potent with an $IC_{50}$ of 18.5 nM and 1.6-fold selectivity. Fully complementary to the ATXN-3 CAG repeat region, ISIS 537787 showed inhibition of mutant ATXN-3 protein expression with an $IC_{50}$ of 10.7 nM but no selectivity relative to inhibition of the wild-type ATXN-3.

TABLE 3

Selectivity and Inhibition of ATXN-3 protein expression levels of modified ssRNAs

| RNA | ISIS NO. | mut $IC_{50}$ (nM) | wt $IC_{50}$ (nM) | Mismatch position | Selectivity (mut vs wt) | 5'-Chemistry |
|---|---|---|---|---|---|---|
| ss | 537775 | 8.7 | 22.9 | 9 | 3 | (E)-vinyl phosphonate |
| ss | 537786 | 18.5 | 28 | 10 | 1.6 | (E)-vinyl phosphonate |
| ss | 537787 | 10.7 | 12.95 | Fully complementary | 1.2 | (E)-vinyl phosphonate |

Example 3

Evaluation of Argonaute (Ago) Proteins in ssRNA-Mediated Inhibition of HTT Expression Argonaute (Ago) proteins are critical mediators of RNAi. There are four Ago variants in human cells (Ago1-4), with Ago2 being the best characterized. Ago2 promotes association of RNA with complementary mRNA sequences and can induce cleavage of the mRNA target. To examine the potential for Argonaute to mediate action of ssRNAs, effects of reducing cellular Ago levels on inhibition of HTT expression by ssRNAs and siRNAs were evaluated.

The modified ssRNAs and siRNAs are described in Table 4. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH—)$. A "Po" at the 5'-end indicates a 5'-phosphate $(PO(OH)_2—)$. Nucleosides without a subscript are β-D-2'-deoxyribonucleosides. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. Underlined nucleosides indicate the mismatch position.

The patient-derived fibroblast cell line GM04281 was obtained from the Coriell Institute (Camden, N.J.). Cells were maintained at 37° C. and 5% $CO_2$ in Minimal Essential Media Eagle (MEM) (Sigma, M4655) supplemented with 10% heat inactivated fetal bovine serum (Sigma) and 0.5% MEM nonessential amino acids (Sigma). Cells were plated at a density of 60,000 cells per well and transfected using lipid RNAiMAX (Invitrogen). First transfection was performed using 25 nM concentration of siRNAs that were complementary to Ago1-4 to inhibit the expression of Ago1-4. These siRNAs are denoted as "siAgo1", "siAgo2", "siAgo3", and "siAgo4". "siAgo2" is a mixture of 4 different siRNAs to achieve maximal inhibition of Ago2 level and denoted as "siAgo2-1", "siAgo2-2", "siAgo2-3", and "siAgo2-4". Second transfection was performed using either 6 nM concentration of ISIS 537775 that contains a single mismatch at position 9 or 9 nM concentration of BBRC, an siRNA complementary to HTT mRNA outside the CAG repeat. Noncomplementary RNA duplex (CM) was used as a control at 25 nM concentration. Typically 4 μL of lipid per well is used for transfection at 100 nM in accordance to manufacturer's protocol. Media containing RNA and lipid are mixed and allowed to sit for 20 minutes for complex formation, and the lower doses are obtained by way of serial dilution at 1:2 or 1:3-fold. Media was exchanged 1 day after transfection with fresh supplemented MEM. Cells were washed with phosphate-buffered saline and harvested 4 days after transfection for protein analysis.

Figure 2:
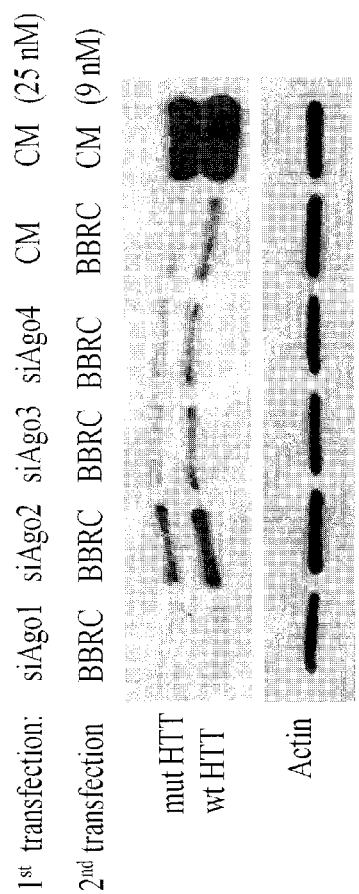
FIG. 2 shows the effects of reducing cellular Argonaute levels on inhibition of HTT expression by siRNA, BBRC.

HTT protein was analyzed by western blot analysis using the method described previously and the results are presented in FIG. 1. As illustrated in FIG. 1, inhibition of Ago2 had the largest effect, partially reversing the allele-selective inhibition of HTT by ISIS 537775. By contrast, silencing AGO1, AGO3, or AGO4 had little effect on allele-selective inhibition of mutant HTT. As expected, inhibition of Ago2 also reversed the effects of anti-HTT siRNA BBRC (FIG. 2). The results from this study identified Ago2 as the best candidate for mediating the action of ssRNAs in inhibition of HTT expression.

TABLE 4

Modified ssRNAs and siRNAs

| RNA | ISIS NO. | Sequence | SEQ ID NO. |
|---|---|---|---|
| ss | 537775 | 5'-Pv-T$_{es}$C$_{fs}$U$_{m}$G$_{fs}$C$_{m}$U$_{fs}$G$_{m}$C$_{fs}$A$_{m}$G$_{fs}$ C$_{m}$U$_{fs}$G$_{m}$C$_{fs}$U$_{ms}$G$_{fs}$C$_{ms}$U$_{fs}$G$_{ms}$A$_{es}$A$_{e}$-3' | 1 |
| siAgo1 | XXXXX1 | 5'-GGAGUUACUUUCAUAGCAUUU-3' | 11 |
| | | 3'-UUCCUCAAUGAAAGUAUCGUA-Po-5' | 12 |
| siAgo2-1 | XXXXX2 | 5'-GCACGGAAGUCCAUCUGAAUU-3' | 13 |
| | | 3'-UUCGUGCCUUCAGGUAGACUU-Po-5' | 14 |
| siAgo2-2 | XXXXX3 | 5'-GCAGGACAAAGAUGUAUUAUU-3' | 15 |
| | | 3'-UUCGUCCUGUUUCUACAUAAU-Po-5' | 16 |
| siAgo2-3 | XXXXX4 | 5'-GGGUCUGUGGUGAUAAAUAUU-3' | 17 |
| | | 3'-UUCCCAGACACCACUAUUUAU-Po-5' | 18 |
| siAgo2-4 | XXXXX5 | 5'-GUAUGAGAACCCAAUGUCAUU-3' | 19 |
| | | 3'-UUCAUACUCUUGGGUUACAGU-Po-5' | 20 |
| siAgo3 | XXXXX6 | 5'-GCAUCAUUAUGCAAUAUGAUU-3' | 21 |
| | | 3'-UUCGUAGUAAUACGUUAUACU-Po-5' | 22 |
| siAgo4 | XXXXX7 | 5'-GGCCAGAACUAAUAGCAAUUU-3' | 23 |
| | | 3'-UUCCGGUCUUGAUUAUCGUUA-Po-5' | 24 |
| si (CM) | XXXXX8 | 5'-GCUAUACCAGCGUCGUCAUAA-3' | 25 |
| | | 3'-TTCGAUAUGGUCGCAGCAGUA-5' | 26 |
| si (BBRC) | XXXXX9 | 5'-CAGACAAUGAUUCACACGGUTT-3' | 27 |
| | | 3'-TTGUCUGUUACUAAGUGUGCCA-5' | 28 |

Example 4

Modified ssRNAs Comprising Mismatches Targeting HTT CAG Repeat Region

Additional ssRNAs were designed by having a 5'-phosphate group and mismatches at various positions throughout the oligonucleotides in an effort to evaluate the effects of mismatches at varied positions on potency and selectivity in inhibition of mutant HTT protein expression levels.

The modified ssRNAs are described in Table 5. A subscript "s" between two nucleosides indicates a phosphorothioate internucleoside linkage (from the 5' to the 3' end). The absence of a subscript "s" between two nucleosides indicates a phosphodiester internucleoside linkage. A "Po" at the 5'-end indicates a 5'-phosphate group, (PO(OH)$_2$—). Nucleosides without a subscript are β-D-2'-deoxyribonucleosides. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. Underlined nucleosides indicate the mismatch position.

The modified ssRNAs were tested in patient-derived fibroblast cell line GM04281 (69 CAG repeats mutant/17 CAG repeats wild-type). Cultured GM04281 cells at a density of 60,000 cells per well were transfected using lipid RNAiMAX (Invitrogen) with 0.2, 0.6, 1.8. 5.6, 16.7, 50 and 100 nM concentrations of ssRNAs. Noncomplementary RNA duplex (CM) was used as a control at 50 nM concentration. Typically 4 μL of lipid per well was used for transfection at 100 nM in accordance to manufacturer's protocol. Media containing RNA and lipid were mixed and allowed to sit for 20 minutes for complex formation, and the lower doses were obtained by way of serial dilution at 1:2 or 1:3-fold. Media was exchanged 1 day after transfection with fresh supplemented MEM. Cells were washed with phosphate-buffered saline and harvested 4 days after transfection for protein analysis.

The mutant and wild-type HTT protein expression levels were analyzed and the IC$_{50}$ along with the selectivity were calculated using methods as described previously. The IC$_{50}$ at which each oligonucleotide inhibits the mutant HTT protein expression is denoted as 'mut IC$_{50}$'. The IC$_{50}$ at which each oligonucleotide inhibits the wild-type HTT protein expression is denoted as 'wt IC$_{50}$'. The results are presented in Table 6.

The modified ssRNAs, ISIS 553819 and ISIS 553822 marked with an asterisk (*) in the table were included in the study as benchmark oligonucleotides against which the potency and selectivity of the modified ssRNAs could be compared. ISIS 553819 was fully complementary to the HTT CAG repeat region and ISIS 553822 contained a single mismatch at position 9.

As illustrated in Table 6, except for ISIS 556888, treatment with modified ssRNAs comprising a 5'-phosphate group and mismatches at various positions showed potency and selectivity in inhibiting mutant HTT protein levels in a similar manner as compared to ISIS 553819, a HTT CAG repeat complement and ISIS 553822 which contained a single mismatch at position 9.

TABLE 5

Modified ssRNAs targeting HTT CAG Repeat Regions

| RNA | ISIS NO | Sequence | Mismatch position(s) | SEQ ID NO |
|---|---|---|---|---|
| ss | 553819* | 5'-Po-T$_{es}$C$_{fs}$U$_m$G$_{fs}$C$_m$U$_{fs}$G$_m$C$_{fs}$U$_m$G$_{fs}$C$_m$ U$_{fs}$G$_m$C$_{fs}$U$_{ms}$G$_{fs}$C$_{ms}$U$_{fs}$G$_{ms}$A$_{es}$A$_e$-3' | Fully complementary | 7 |
| ss | 556886 | 5'-Po-T$_{es}$C$_{fs}$U$_m$G$_{fs}$<u>A$_m$</u>C$_m$U$_{fs}$G$_m$C$_{fs}$U$_m$G$_{fs}$C$_m$ U$_{fs}$G$_m$C$_{fs}$U$_{ms}$G$_{fs}$C$_{ms}$<u>U$_{fs}$</u>G$_{ms}$A$_{es}$A$_e$-3' | 4 | 29 |
| ss | 556887 | 5'-Po-T$_{es}$C$_{fs}$U$_m$G$_{fs}$C$_m$<u>A$_m$</u>U$_{fs}$G$_m$C$_{fs}$U$_m$G$_{fs}$C$_m$ U$_{fs}$G$_m$C$_{fs}$U$_{ms}$G$_{fs}$C$_{ms}$<u>U$_{fs}$</u>G$_{ms}$A$_{es}$A$_e$-3' | 5 | 30 |
| ss | 556888 | 5'-Po-T$_{es}$C$_{fs}$U$_m$G$_{fs}$C$_m$U$_{fs}$<u>A$_m$</u>C$_{fs}$U$_m$G$_{fs}$C$_m$ U$_{fs}$G$_m$C$_{fs}$U$_{ms}$G$_{fs}$C$_{ms}$U$_{fs}$G$_{ms}$<u>A$_{es}$</u>A$_e$-3' | 6 | 31 |
| ss | 556889 | 5'-Po-T$_{es}$C$_{fs}$U$_m$G$_{fs}$C$_m$U$_{fs}$G$_m$<u>A$_m$</u>U$_m$G$_{fs}$C$_m$ U$_{fs}$G$_m$C$_{fs}$U$_{ms}$G$_{fs}$C$_{ms}$U$_{fs}$G$_{ms}$<u>A$_{es}$A$_e$</u>-3' | 7 | 32 |
| ss | 556890 | 5'-Po-T$_{es}$C$_{fs}$U$_m$G$_{fs}$C$_m$U$_{fs}$G$_m$C$_{fs}$<u>A$_m$</u>G$_{fs}$C$_m$ U$_{fs}$G$_m$C$_{fs}$U$_{ms}$G$_{fs}$C$_{ms}$U$_{fs}$G$_{ms}$A$_{es}$A$_e$-3' | 8 | 33 |
| ss | 553822* | 5'-Po-T$_{es}$C$_{fs}$U$_m$G$_{fs}$C$_m$U$_{fs}$G$_m$C$_{fs}$<u>A$_m$</u>G$_{fs}$C$_m$U$_{fs}$ G$_m$C$_{fs}$U$_{ms}$G$_{fs}$C$_{ms}$U$_{fs}$G$_{ms}$A$_{es}$A$_e$-3' | 9 | 1 |
| ss | 553821 | 5'-Po-T$_{es}$C$_{fs}$U$_m$G$_{fs}$C$_m$U$_{fs}$G$_m$C$_{fs}$U$_m$<u>A$_{fs}$</u>C$_m$ U$_{fs}$G$_m$C$_{fs}$U$_{ms}$G$_t$C$_{ms}$U$_{fs}$G$_{ms}$A$_{es}$A$_e$-3' | 10 | 34 |
| ss | 557407 | 5'-Po-T$_{es}$C$_{fs}$U$_m$G$_{fs}$C$_m$U$_{fs}$G$_m$C$_{fs}$U$_m$<u>U$_{fs}$</u>C$_m$ U$_{fs}$G$_m$C$_{fs}$U$_{ms}$G$_{fs}$C$_{ms}$U$_{fs}$G$_{ms}$A$_{es}$A$_e$-3' | 10 | 35 |
| ss | 556891 | 5'-Po-T$_{es}$C$_{fs}$U$_m$G$_{fs}$C$_m$U$_{fs}$G$_m$C$_{fs}$U$_m$G$_{fs}$<u>A$_m$</u> U$_{fs}$G$_m$C$_{fs}$U$_{ms}$G$_{fs}$C$_{ms}$U$_{fs}$G$_{ms}$A$_{es}$A$_e$-3' | 11 | 36 |
| ss | 556892 | 5'-Po-T$_{es}$C$_{fs}$U$_m$G$_{fs}$C$_m$U$_{fs}$G$_m$C$_{fs}$U$_m$G$_{fs}$C$_m$ <u>A$_{fs}$</u>G$_m$C$_{fs}$U$_{ms}$G$_{fs}$C$_{ms}$U$_{fs}$G$_{ms}$A$_{es}$A$_e$-3' | 12 | 37 |
| ss | 557406 | 5'-Po-T$_{es}$C$_{fs}$U$_m$G$_{fs}$C$_m$U$_{fs}$G$_m$C$_{fs}$U$_m$G$_{fs}$C$_m$ U$_{fs}$<u>A$_m$</u>C$_{fs}$U$_{ms}$G$_{fs}$C$_{ms}$U$_{fs}$G$_{ms}$A$_{es}$A$_e$-3' | 13 | 38 |

TABLE 5-continued

Modified ssRNAs targeting HTT CAG Repeat Regions

| RNA | ISIS NO | Sequence | Mismatch position(s) | SEQ ID NO |
|---|---|---|---|---|
| ss | 557408 | 5'-Po-$T_{es}C_{fs}U_mG_{fs}C_mU_{fs}G_mC_{fs}U_mG_{fs}C_m$ $U_{fs}G_mC_{fs}U_{ms}\underline{A_{fs}}C_{ms}U_{fs}G_{ms}A_{es}A_e$-3' | 16 | 39 |
| ss | 557409 | 5'-Po-$T_{es}C_{fs}U_mG_{fs}C_mU_{fs}G_mC_{fs}\underline{A_m}\underline{A_{fs}}C_m$ $U_{fs}G_mC_{fs}U_{ms}G_{fs}C_{ms}U_{fs}G_{ms}A_{es}A_e$-3' | 9, 10 | 40 |
| ss | 557426 | 5'-Po-$T_{es}C_{fs}U_mG_{fs}C_mU_{fs}G_mC_{fs}\underline{A_m}\underline{A_{fs}}\underline{A_m}$ $U_{fs}G_mC_{fs}U_{ms}G_{fs}C_{ms}U_{fs}G_{ms}A_{es}A_e$-3' | 9, 10, 11 | 41 |
| ss | 557427 | 5'-Po-$T_{es}C_{fs}U_mG_{fs}C_mU_{fs}G_m\underline{A_{fs}}\underline{A_m}\underline{A_{fs}}\underline{A_m}$ $U_{fs}G_mC_{fs}U_{ms}G_{fs}C_{ms}U_{fs}G_{ms}A_{es}A_e$-3' | 8, 9, 10, 11 | 42 |
| ss | 557428 | 5'-Po-$T_{es}C_{fs}U_m\underline{A_{fs}}C_mU_{fs}G_mC_{fs}U_m\underline{A_{fs}}C_m$ $U_{fs}G_mC_{fs}U_{ms}\underline{A_{fs}}C_{ms}U_{fs}G_{ms}A_{es}A_e$-3' | 4, 10, 16 | 43 |
| ss | 557429 | 5'-Po-$T_{es}C_{fs}\underline{A_m}G_{fs}C_mU_{fs}G_m\underline{U_{fs}}U_mG_{fs}C_m$ $U_{fs}\underline{A_m}C_{fs}U_{ms}G_{fs}\underline{U_{ms}}U_{fs}G_{ms}A_{es}A_e$-3' | 3, 8, 13, 17 | 44 |
| ss | 557430 | 5'-Po-$T_{es}G_{fs}C_mU_{fs}G_mC_{fs}U_mG_{fs}C_mU_{fs}G_m$ $C_{fs}U_mG_{fs}C_{ms}U_{fs}G_{ms}C_{fs}U_{ms}A_{es}A_e$-3' | Fully complementary | 45 |
| si (CM) | XXXXX8 | 5'-GCU$\underline{AU}$ACCAGCGU$\underline{C}$GUCAU$\underline{A}$A-3' 3'-TTCG$\underline{AU}$AUGGUCGCA$\underline{G}$CAGU$\underline{A}$-5' | 4, 6, 14, 19 6, 8, 16, 21 | 25 26 |

TABLE 6

Selectivity and inhibition of HTT protein levels with modified ssRNAs comprising mismatches at various positions

| RNA | ISIS NO | mut IC$_{50}$ (Nm) | wt IC$_{50}$ (Nm) | Selectivity (wt vs. mut) | Mismatch position(s) | 5'-Chemistry |
|---|---|---|---|---|---|---|
| ss | 553819* | 2 | 30 | 15 | Fully complementary | Phosphate |
| ss | 556886 | 8.8 | 61.1 | 7 | 4 | Phosphate |
| ss | 556887 | 17.2 | >100 | >6 | 5 | Phosphate |
| ss | 556888 | N.I. | N.I. | N/A | 6 | Phosphate |
| ss | 556889 | 11.2 | 51.1 | 5 | 7 | Phosphate |
| ss | 556890 | 4.1 | 29.5 | 7 | 8 | Phosphate |
| ss | 553822* | 4.9 | 90.4 | 18 | 9 | Phosphate |
| ss | 553821 | 17.8 | >100 | >6 | 10 | Phosphate |
| ss | 557407 | 15.3 | >100 | >7 | 10 | Phosphate |
| ss | 556891 | 12.8 | >100 | >8 | 11 | Phosphate |
| ss | 556892 | 3.4 | 72.0 | 21 | 12 | Phosphate |
| ss | 557406 | 4.2 | >100 | >24 | 13 | Phosphate |
| ss | 557408 | 8.1 | 27.3 | 3 | 16 | Phosphate |
| ss | 557409 | 6.3 | >100 | >16 | 9, 10 | Phosphate |
| ss | 557426 | 3.3 | >100 | >30 | 9, 10, 11 | Phosphate |
| ss | 557427 | 11.8 | >100 | >8 | 8, 9, 10, 11 | Phosphate |
| ss | 557428 | 22.3 | >100 | >4 | 4, 10, 16 | Phosphate |
| ss | 557429 | N.I. | N.I. | N/A | 3, 8, 13, 17 | Phosphate |
| ss | 557430 | 19.4 | >100 | >5 | Fully complementary | Phosphate |
| si (CM) | XXXXX8 | N.I. | N.I. | N/A | Non-complementary | OH |

N.I. = No Inhibition;
N/A = Not Available

Example 5

Effect of Modified ssRNAs on Selectivity and Inhibition of HTT Protein Expression Over Time The modified ssRNA from Table 1, ISIS 537775 targeting HTT CAG repeat region was selected and evaluated for inhibition of HTT protein expression levels and selectivity over 14 days using the procedures described herein. The modified ssRNA was tested in patient-derived fibroblast cell line GM04281 (69 CAG repeats mutant/17 CAG repeats wild-type). Cultured GM04281 cells were plated in 6-well plates at a density of 60,000 cells per well in supplemented MEM media two days prior to transfection. 6-well plates were used to provide the number of cells necessary for western analysis. Cells were transfected only once at the beginning of the experiment using lipid RNAiMAX (Invitrogen) with a single dose of ISIS 537775 at 12.5 nM concentration. During this period, cells were allowed to grow, undergoing 3-4 population doublings and diluting out the modified ssRNA available to silencing HTT. HTT protein analysis by Western blot and quantitation relative to non-treated control levels (NT) were performed in the same manner as described previously and the results are presented below.

Figure 3A:
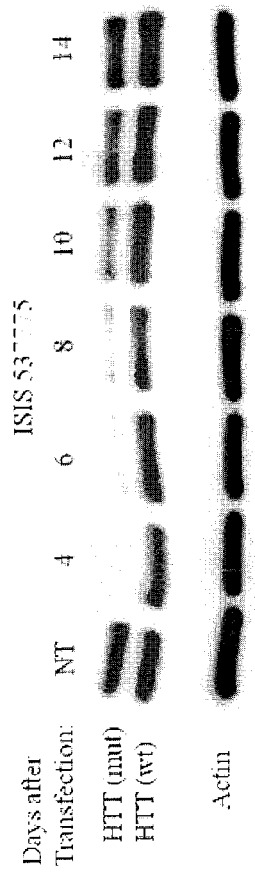
FIG. 3a shows Western analysis of ISIS 537775 on selective inhibition of mut HTT protein expression over 14 days.
Figure 3B:
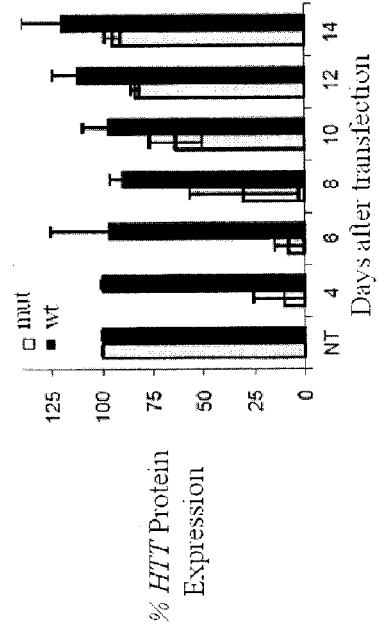
FIG. 3b shows quantitation of Western analysis of HTT protein expression of ISIS 537775 over 14 days.

As illustrated in FIGS. 3a and 3b, selective inhibition of mutant HTT expression was observed for up to 8 days before population doublings gradually diluted out the ssRNA-induced inhibition, returning to original levels after two weeks.

Example 6

Effect of Modified ssRNAs as a Duplex on Selective Inhibition of Mut HTT Protein Expression Targeting HTT CAG Repeat Region To determine the functional necessity of a passenger strand, a duplex was created by annealing the modified ssRNA from Table 1, ISIS 537775 to an unmodified RNA passenger strand. The resulting heteroduplex was tested and evaluated for selective inhibition of mut HTT protein expression. The heteroduplex was tested in patient-derived fibroblast cell line GM04281 (69 CAG repeats mutant/17 CAG repeats wild-type). Cultured GM04281 cells at a density of 60,000 cells per well were transfected using lipid RNAiMAX (Invitrogen) with 0.0, 0.2, 0.6, 1.8. 5.6, 16.7, 50 and 100 nM concentrations of the heteroduplex. Non-complementary RNA duplex denoted as "MM" was used as a control at 50 nM concentration. Typically 4 µl, of lipid per well was used for transfection at 100 nM in accordance to manufacturer's protocol. Media containing RNA and lipid were mixed and allowed to sit for 20 minutes for complex formation, and the lower doses were obtained by way of serial dilution at 1:2 or 1:3-fold. Media was exchanged 1 day after transfection with fresh supplemented MEM. Cells were washed with phosphate-buffered saline and harvested 4 days after transfection for protein analysis. HTT protein analysis by Western blot and $IC_{50}$ calculation were performed in the same manner as described previously and the results are presented below.

The unmodified RNA passenger strand is designated herein as SEQ ID NO: 55, 3'-$C_{rs}G_{rs}A_{rs}C_{rs}G_{rs}A_{rs}C_{rs}G_{rs}A_{rs}C_{rs}G_{rs}A_{rs}C_{rs}G_{rs}A_{rs}C_{rs}G_{rs}A_{rs}C_{rs}G_{rs}A_{rs}C$-5'. A subscript "s" between two nucleosides indicates a phosphorothioate internucleoside linkage (going 3' to 5') and a subscript "r" indicates a ribonucleoside (RNA). Noncomplementary RNA duplex, MM has the same sequence as CM described in Table 4 and designated herein as SEQ ID NO: 25, 26.

Figure 4:
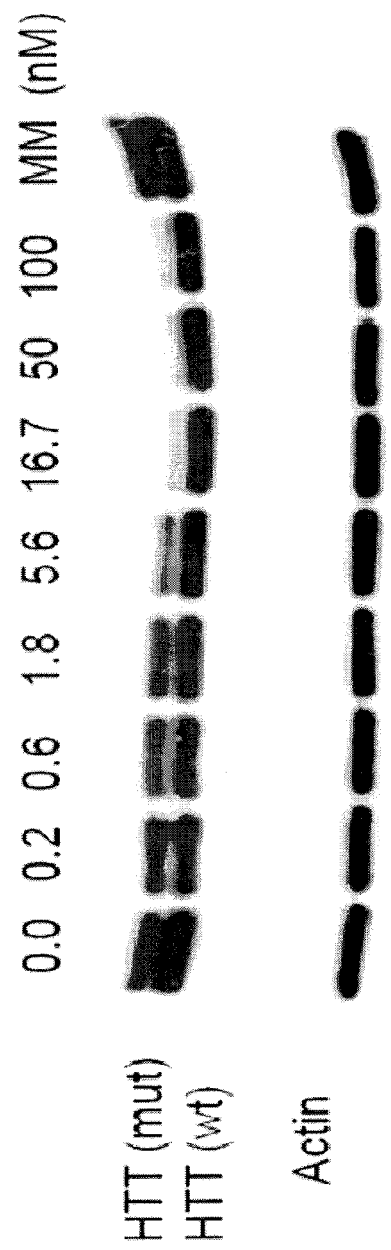
FIG. 4 shows the effect of ISIS 537775 as a duplex on selective inhibition of mut HTT protein expression targeting HTT CAG repeat region.

As illustrated in FIG. 4, the heteroduplex showed selective inhibition of mut HTT expression similar to the modified ssRNA 537775 alone (Table 2) with an $IC_{50}$ of 5.4 nM and a selectivity of greater than 15 fold.

Example 7

Effect of Modified ssRNAs on Selective Inhibition of Mut HTT Protein Expression Targeting HTT CAG Repeats in GM04719 Patient Derived Fibroblast Cells The modified ssRNA from Table 1, ISIS 553822 was tested in patient-derived fibroblast cell line GM04719 obtained from Corielle Institute (44 CAG repeats mutant/15 CAG repeats wild-type). Cultured GM04719 cells at a density of 60,000 cells per well were transfected using lipid RNAiMAX (Invitrogen) with 0.0, 0.2, 0.6, 1.8. 5.6, 16.7, 50 and 100 nM concentrations of ISIS 553822. Typically 4 µl, of lipid per well was used for transfection at 100 nM in accordance to manufacturer's protocol. Media containing RNA and lipid were mixed and allowed to sit for 20 minutes for complex formation, and the lower doses were obtained by way of serial dilution at 1:2 or 1:3-fold. Media was exchanged 1 day after transfection with fresh supplemented MEM. Cells were washed with phosphate-buffered saline and harvested 4 days after transfection for protein analysis. HTT protein analysis by Western blot and $IC_{50}$ calculation were performed in the same manner as described previously and the results are presented below.

Figure 5:
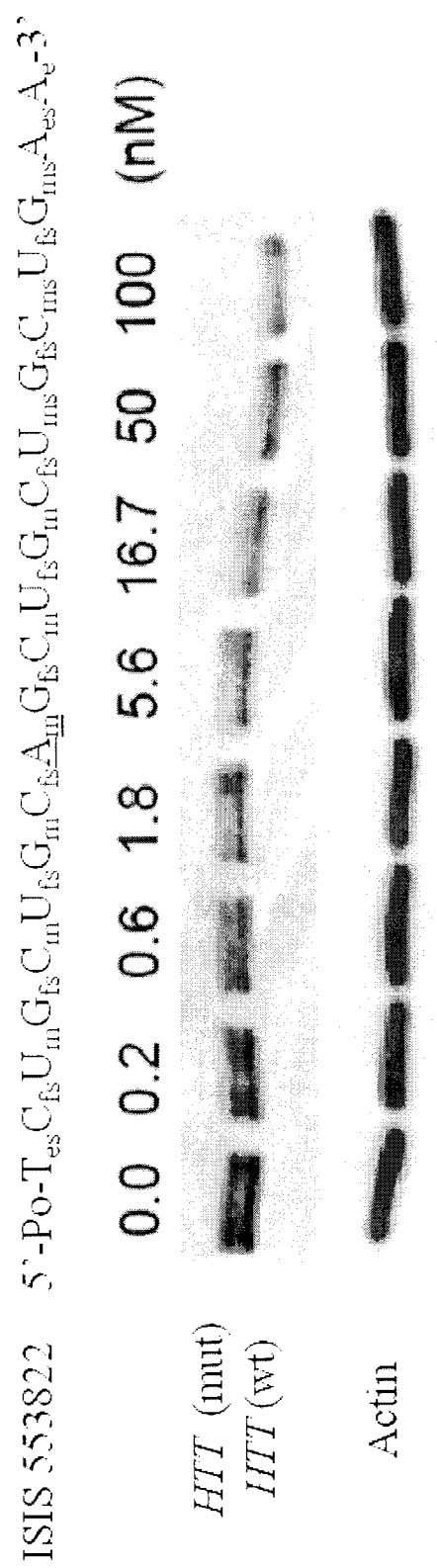
FIG. 5 shows the effect of ISIS 553822 on selectivity and inhibition of HTT protein expression in GM04719 patient derived fibroblast cells.

As illustrated in FIG. 5, the modified ssRNA 553822 comprising a 5'-terminal phosphate group showed selective inhibition of mut HTT expression with an $IC_{50}$ of 0.9 nM and a selectivity of greater than 100 fold. ISIS 553822 demonstrated some inhibition of wild-type HTT expression at high concentrations, however the inhibition of wild-type HTT expression leveled off at approximately 45% (FIG. 5).

Example 8

Effect of Modified ssRNAs on HTT mRNA Levels Targeting HTT CAG Repeat Region The modified ssRNAs from Table 1, ISIS 537775 and 553822 targeting HTT CAG repeat region were selected and evaluated for inhibition of HTT mRNA expression levels in vitro. The modified ssRNAs were tested in patient-derived fibroblast cell line GM04281 (69 CAG repeats mutant/17 CAG repeats wild-type). Cultured GM04281 cells were plated in 6-well plates at a density of 60,000 cells per well in supplemented MEM media two days prior to transfection. 6-well plates were used to provide the number of cells necessary for western analysis. Cells were transfected with 12.5, 25 and 50 nM concentrations of ISIS 537775 or 553822 using lipid RNAiMAX (Invitrogen). BBRC, an siRNA complementary to HTT mRNA outside the CAG repeat was used as a positive control at 50 nM concentration. Noncomplementary RNA duplex (CM) was used as a negative control at 50 nM concentration. Cells were harvested 3 days after transfection for RNA analysis. The sequences for BBRC and CM are described in Table 4.

HTT mRNA expression was analyzed by quantitative PCR (Q-PCR) using the method described herein. Experiments were performed in biological triplicate and error reported as standard deviation. The Q-PCR cycles are as follows: 50° C. for 2 min; 95° C. for 5 min; (95° C. for 15 s; 60° C. for 1 min)×40 cycles. The results are presented below.

Figure 6:
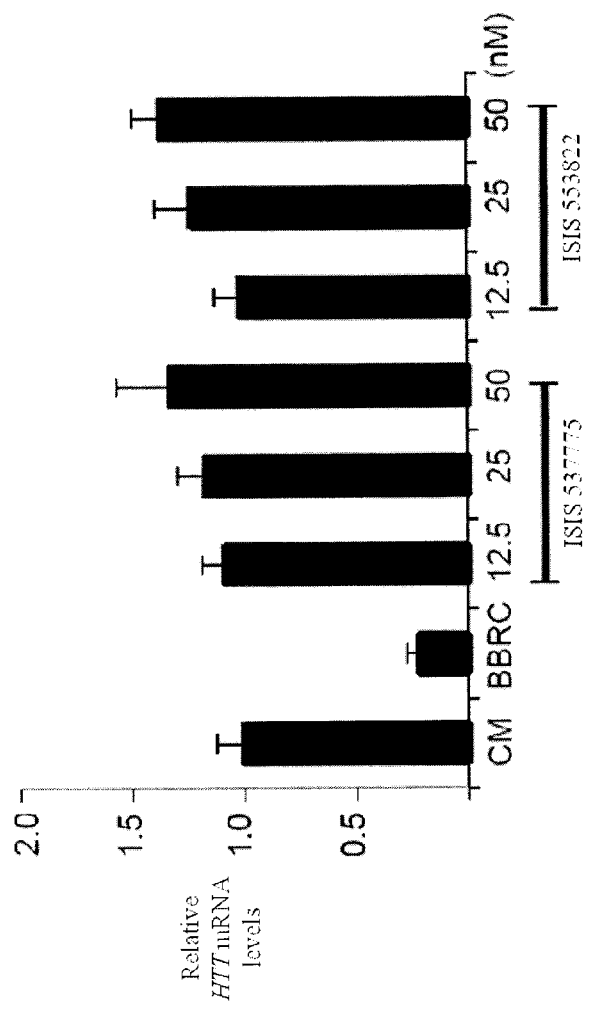
FIG. 6 shows the effect of ISIS 537775 and 553822 on HTT mRNA levels in vitro.

As illustrated in FIG. 6, the duplex siRNA that targets a sequence outside of the CAG repeat region (BBRC) showed reduction in HTT mRNA levels by greater than 80%. In contrast, the modified ssRNAs containing a single mismatch at position 9 having a 5'-terminal vinyl phosphonate, ISIS 537775 or a 5'-terminal phosphate, ISIS 553822 showed no reduction in HTT mRNA levels. This result suggests that the mechanism for allele-selective inhibition of HTT involves in blocking protein translation rather than degradation of mRNA.

Example 9

Effect of Modified ssRNAs on Other Genes Containing Trinucleotide Repeats

Another challenge for agents that target trinucleotide repeats is the existence of other genes that contain repetitive regions (Kozlowski et al., 2010). To evaluate the effect of modified ssRNAs on other genes containing trinucleotide repeats, ISIS 557426 from Table 5 was selected and evaluated in vitro. Such genes include but are not limited to androgen receptor or AR (approximately 20 CAG repeats), AAK-1 (6 CAG repeats), POU3F2 (6 CAG repeats), FOXP2

(40 glutamines encoded by a mix of CAG and CAA trinucleotides) and TATA-box binding protein or TBP (19 CAG repeats). The modified ssRNA was tested in in the same manner as described in Example 1. Cultured GM04281 cells were plated in 6-well plates at a density of 60,000 cells per well in supplemented MEM media two days prior to transfection. 6-well plates were used to provide the number of cells necessary for western analysis. Cells were transfected with 0.0, 0.2, 0.6, 1.8, 5.6, 16.7, 50 and 100 nM concentrations using lipid RNAiMAX (Invitrogen). Non-complementary RNA duplex denoted as "MM" was used as a control at 50 nM concentration. Cells were harvested 4 days after transfection for protein analysis. Protein analysis by Western blot was performed in the same manner as described previously. Inhibition of proteins from genes listed above by modified ssRNA was compared to the inhibition of mutant HTT protein expression and the results are presented below.

Figure 7:
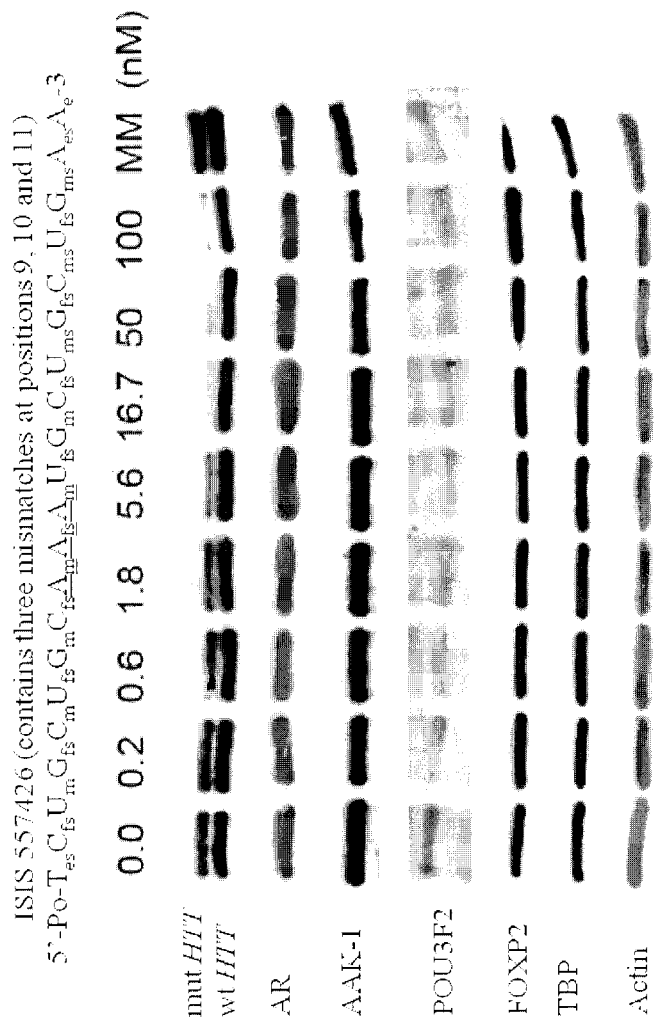
FIG. 7 shows the effect of ISIS 557426 on genes containing trinucleotide repeats in vitro.

As illustrated in FIG. 7, selective inhibition was observed for mutant HTT protein expression by ISIS 557426 while no inhibition was observed for other proteins such as AR, AAK-1, POU3F2, FOXP2 or TBP at concentrations above those needed to achieve selective inhibition of mutant HTT.

Example 10

Evaluation of Modified ssRNAs on Selective Inhibition of Mut HTT Targeting HTT CAG Repeats—In Vivo Study The modified ssRNA from Table 1, ISIS 537775 targeting HTT CAG repeats was selected and evaluated in vivo using the procedures described herein. A nonallele-selective 5-10-5 MOE gapmer, ISIS 387898 was included in the study as a positive control against which only the potency (not selectivity) of the modified ssRNA could be compared since it is complementary to a region outside the CAG repeat and therefore, not expected to be selective against mutant HTT.

The positive control 5-10-5 MOE gapmer, ISIS 387898 is designated herein as SEQ ID NO: 9, 5'-$^mC_{es}T_{es}{}^mC_{es}G_{es}A_{es}{}^mC_{ds}T_{as}A_{ds}A_{ds}A_{ds}G_{as}{}^mC_{ds}A_{ds}G_{as}G_{ds}A_{es}T_{es}T_{es}T_{es}{}^mC_{e}$-3'. A subscript "s" between two nucleosides indicates a phosphorothioate internucleoside linkage (5' to 3'). Nucleosides with subscripts "d" are β-D-2'-deoxyribonucleosides. Nucleosides with subscripts "e" are 2'-O-methoxyethyl (MOE) modified nucleosides. $^{me}C$ indicates a 5-methyl cytosine nucleoside.

Dosing and Surgical Procedure

HdhQ150 heterozygous knockin HD-model mice (Lin et al., 2001) were used in the study. The HdhQ150 heterozygous mice carry one mouse huntingtin allele with 150 CAG repeats knocked into Exon 1 (Q150) and a second allele with a wild-type mouse huntingtin gene (Q7). The two HTT alleles in the HdhQ150/Q7 animals differ only in the length of the CAG repeat, making them ideal for determining whether an ssRNA can discriminate between the expanded and unexpanded huntingtin transcripts in vivo.

The HdhQ150 (CHL2) animals (Lin et al., 2001) were obtained from Jackson laboratories and maintained on the congenic C57BL/6 background. To continuously deliver compounds, osmotic pumps delivering 0.25 µL/hr (Model 2004) were used to deliver 300 µg/day of the modified ssRNA 537775 or phosphate buffered saline (PBS, Sigma Aldrich) for 28 days. Pumps designed to deliver 0.5 µL/hr (Model 2002) were used to deliver 75 µg/day of the positive control MOE gapmer 387898 for 14 days. Pumps (Durect Corporation) were filled with the modified ssRNA 537775 or MOE gapmer 387898 diluted in sterile PBS and then incubated at 37° C. for 24 or 48 hours prior to implantation.

Analysis of HTT Protein Expression

SDS-PAGE (separating gel: 5% acrylamide-bisacrylamide [50:1], 450 mM Tris-acetate pH 8.8; stacking gel 4% acrylamide-bisacrylamide [50:1], 150 mM Tris-acetate pH 6.8) was used to separate wild-type and mutant HTT proteins as described (Hu et al. 2010).

Analysis of HTT mRNA Expression

Quantitative PCR (Q-PCR) was performed as described. Experiments were performed in biological triplicate and error reported as standard deviation. The Q-PCR cycles are as follows: 50° C. for 2 min; 95° C. for 5 min; (95° C. for 15 s; 60° C. for 1 min)×40 cycles.

The modified ssRNA comprising a 5'-terminal vinyl phosphonate, ISIS 537775 was introduced into the cerebral spinal fluid of the right lateral ventricle to achieve distribution throughout the central nervous system, including brain regions implicated in Huntington's Disease (HD) pathology. Mice were treated with modified ssRNA 537775 at 300 µg/day by intracerebroventricular (ICV) infusion for 28 days with a flow rate of 0.25 µL/hr following the method described above. This treatment group consisted of 5 animals. The positive control group received a nonallele-selective MOE gapmer 387898 at 75 µg/day for 14 days at a flow rate of 0.5 µL/hr and consisted of 1 animal. The vehicle control group consisted of 3 animals and received a 0.25 µL/hr infusion of phosphate buffered saline for 28 days.

Mice were anesthetized with 2.5% isofluorane and a midline incision was made at the base of the skull. Using stereotaxic guides, a cannula was implanted into the right lateral ventricle and secured with Loctite adhesive. A catheter attached to an Alzet osmotic mini pump was attached to the cannula and the pump was placed subcutaneously in the midscapular area. The incision was closed with 5.0 nylon sutures. Animals were sacrificed 4 weeks after initiating treatment. Brains were sectioned into 1-2 mm coronal sections and frozen on dry ice and stored at −80. Brain regions were harvested for RNA and biochemical analysis using 2 mm punches. HTT expression by western analysis and Q-PCR were carried out using the method described above. The results are presented below.

Figure 8A:
FIG. 8a shows Western analysis of HTT protein expression on allele-selective inhibition by modified ssRNA 537775 in Q150/Q7 mouse frontal cortex.
Figure 8B:
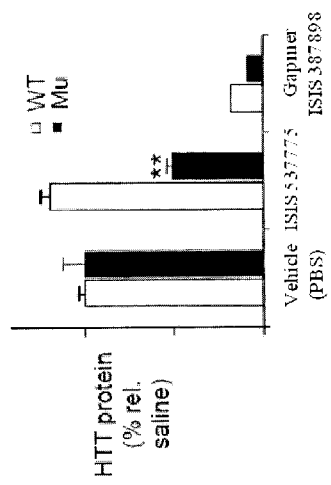
FIG. 8b shows Quantitation of Western analysis of HTT protein expression on allele-selective inhibition by modified ssRNA 537775 in Q150/Q7 mouse frontal cortex.
Figure 8C:
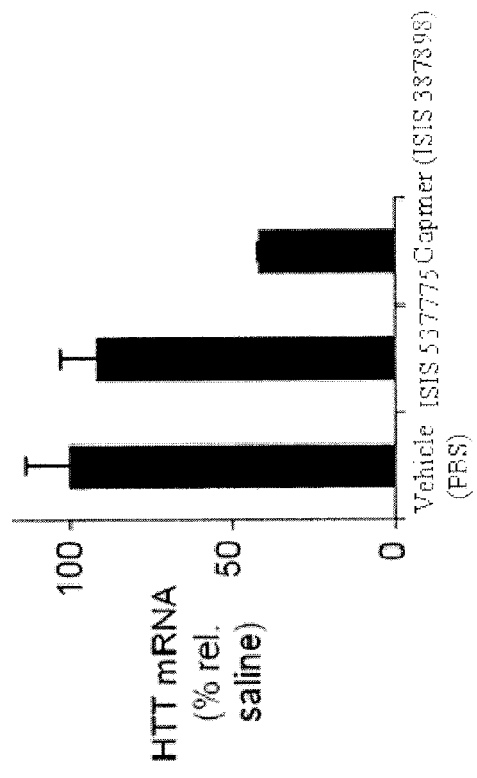
FIG. 8c shows Q-PCR analysis of HTT mRNA levels in Q150/Q7 mouse frontal cortex after treatment with vehicle, modified ssRNA 537775 or control MOE gapmer 387898.

As illustrated in FIGS. 8a and 8b, allele-selective inhibition of HTT protein expression was observed in the frontal cortex of all five mice in the experimental cohort relative to animals treated with saline. Q-PCR showed no reduction in HTT mRNA levels in animals treated with modified ssRNA 537775 (FIG. 8c). This finding is consistent with the results in cultured cells showing inhibition does not result from cleavage of mRNA (FIG. 6).

Figure 8D:
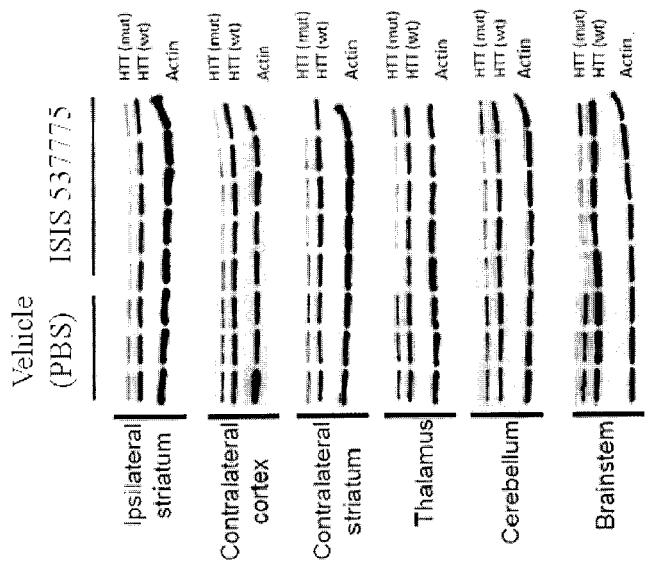
FIG. 8d shows Western analysis of HTT protein expression on allele-selective inhibition by modified ssRNA 537775 in different brain regions of Q150/Q7 mouse.
Figure 8E:
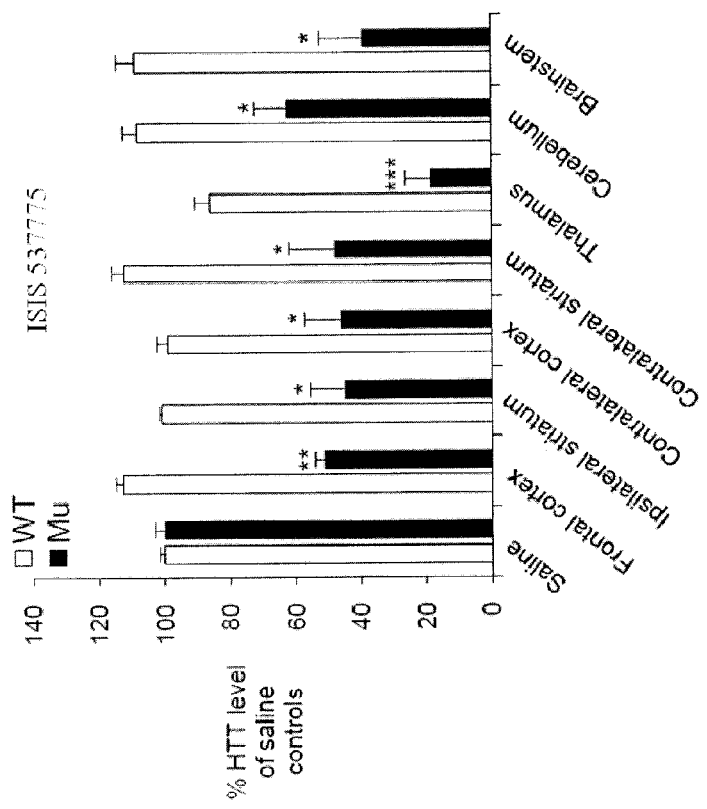
FIG. 8e shows quantitation of Western analysis of HTT protein expression on allele-selective inhibition by modified ssRNA 537775 in different brain regions of Q150/Q7 mouse

Inhibition in other tissues, including contralateral cortex, thalamus, ipsilateral striatum, contralateral striatum, cerebellum, and brainstem was also evaluated. Reduction in mutant HTT protein levels was observed when treated with modified ssRNA 537775 in all tissues evaluated (FIGS. 8d and 8f). Consistent with our results in cultured cells (FIG. 7), injection of ssRNA 537775 did not reduce expression of other proteins containing trinucleotide repeats (FIGS. 9a-f). Results from this study demonstrate that modified ssRNAs can distribute broadly within the central nervous system and inhibit mutant HTT expression.

Example 11

Evaluation of ssRNA Efficacy Targeting HTT CAG Repeat Region—In Vivo Study

The modified ssRNA from Table 1, ISIS 537775 targeting HTT CAG repeat region was selected and evaluated for efficacy study in vivo using the procedures as described herein. Two to four month old HdhQ150 heterozygous mice were used in the study. HdhQ150 mice were generated by Peter Detloff and obtained from Jax labs. HdhQ150 heterozygous mice carry one mouse huntingtin allele with approximately 150 CAG repeats and a second allele with the unmodified mouse huntingtin gene containing 7 CAG repeats (Detloff et al., *Human Molecular Genetics*, 2001, 10, 137-144). The animals were not symptomatic at this age.

Mice were treated with 150 µg/day of ISIS 537775 by intracerebroventricular (ICV) infusion for 28 days using the ALZET 2004 pump with a flow rate of 0.25 µl/hr. This treatment group consisted of 6 animals. The control group consisted of three animals received a 10 µl bolus injection of saline.

Animals were sacrificed at 4 weeks post-treatment initiation. Brains were sectioned into 1-2 mm coronal sections and frozen on dry ice and stored at −80° C. For RNA and biochemical analysis, brain regions were harvested using 2 mm punches.

The HTT protein levels were analyzed by high molecular weight western blot (modified from Invitrogen's NuPAGE Bis-Tris System Protocol). The tissues, cortex and striatum were homogenized in ice cold NP40/DOC lysis buffer. 7 µg of total protein lysate was resolved on a 4-12% bis-tris gel (Invitrogen) in MOPS buffer. Proteins were transferred to a 0.45 mm nitrocellulose membrane, and probed with MAB2166 (1:2000, Millipore). HRP conjugated secondary antibodies were applied (B.D. biosciences, 1:5000) and developed with ECL (Pierce). Approximate quantification was performed in adobe photoshop. Scans of immunoblot films were inverted, then using the selection tool a box was drawn around the largest band present. This same box was used for all analysis and the mean intensity in the histogram function was used as an approximate representation of mutant and normal huntingtin protein levels. All experimental intensities were normalized to background intensity. Background intensity was determined by taking the mean of three randomly selected regions in the background.

The results in Table 7 are presented as the average percent of HTT protein levels for each treatment group, normalized to saline-treated control and is denoted as "% UTC". The percent of mutant HTT protein levels is denoted as "mut". The percent of wild-type HTT protein levels is denoted as "wt".

Due to technical challenges, two animals from ISIS 537775 treatment group failed to receive adequate amounts of oligonucleotide. Selectivity and inhibition of HTT were not observed and therefore, were excluded in the calculation for the average percent protein levels.

As illustrated in Table 7, selectivity for inhibition of mutant HTT protein levels in the cortex and striatum was observed for the modified ssRNA comprising a 5'-vinyphosphonate group, ISIS 537775.

Example 12

Evaluation of the Stability of Modified ssRNAs—In Vivo Study

The stability of modified ssRNAs can be evaluated in vivo using the procedures as described herein. Liver tissues were harvested and collected on ice from BALB/C mice treated with modified ssRNAs. 100-200 mg samples were minced and homogenized in 400 µL homogenization buffer (20 mM Tris, pH 8, 20 mM EDTA, 0.1 M NaCl, 0.5% NP-40). A standard curve ranging from 1 µg-75 µg was prepared for each ssRNA in 500 µL aliquots of control liver homogenate (400 µg/mL) with 10 µg internal standard (SEQ ID NO: 52, Isis NO: 355868, a 27-mer, 2'-O-methoxyethyl-modified phosphorothioate oligonucleotide). Tissue homogenates were then extracted using phenol/chloroform and solid support phase extraction techniques as described below with 300 µL $NH_4OH$ and 8004 phenol/chloroform/isoamyl alcohol used in the phenol/chloroform extraction.

Phenol/Chloroform Extraction

Stability of ssRNAs was evaluated at time points 0, 5, 10, 20, 30, 40 and 60 minutes, except for SEQ ID NO: 53, Isis NO: 408877 which was evaluated at time points 0, 15, 30, 60, 120 and 240 mins; and SEQ ID NO: 54, Isis NO: 409044, at time points 0, 0.5, 1, 2, 4, 8, and 18 hours. An internal standard (SEQ ID NO: 52, Isis NO: 355868, a 27-mer, 2'-O-methoxyethyl-modified phosphorothioate oligonucleotide) with final concentration of 2.5 µM was added to each sample prior to extraction. Samples were extracted with 70 pt of $NH_4OH$ and 240 µL of phenol/chloroform/isoamyl alcohol (25:24:1). The supernatant was removed after centrifugation at 14000 rpm for 2 min. The remaining extractant was vortexed with an additional 500 µL of water and the aqueous layer was removed and combined with the supernatant after centrifugation at 14000 rpm for 2 minutes.

Solid Phase Extraction

Triethylammonium acetate solution at 1M (500 µL) was added to the supernatant. The aqueous layer of the mixture was loaded onto the pre-conditioned Biotage™ Phenyl Solid Phase Extraction Plate (SPE plate) after centrifugation at 9000 rpm for 20 minutes. The SPE plate was washed several times with water. The sample was then eluted with 1.5 mL of 1% TEA in 90% MeOH and filtered through the Protein Precipitation Plate (Phenomenex™). The elutent was evaporated to dryness and diluted to 200 µL with 50% quenching buffer (8 M urea, 50 mM EDTA) and water before sample injection.

LC-MS

An Agilent 1100 Series LC/MSD system was connected in-line to a mass spectrometer. Mass spectrometer was operated in the electrospray negative ionization mode. The nebulizer nitrogen gas was set at 325 psi and the drying nitrogen gas was set at 12 L/min. The drying temperature

TABLE 7

In vivo efficacy of ISIS 537775 targeting HTT by ICV infusion

| ISIS NO | Tissue | Dosage (µg/day) | Route of administration | % UTC mut | wt | 5'-Chemistry |
|---|---|---|---|---|---|---|
| Saline | — | 150 | ICV Bolus | 100 | 100 | — |
| 537775 | Cortex | 150 | ICV infusion | 65.28 | 87.01 | (E)-vinylphosphonate |
| 537775 | Striatum | 150 | ICV infusion | 67.52 | 91.87 | (E)-vinylphosphonate | was 325° C. Samples (25 μL/well) were introduced via an auto sampler and reversed-phase chromatography was carried out with an XBridge OST C18 2.5 μm 2.1 mm×50 mm HPLC column using a flow rate of 300 μL/min at 55° C. The ion pair buffers consisted of A: 5 mM tributylammonium acetate (TBAA) in 20% acetonitrile and B: 5 mM TBAA in 90% acetonitrile and the loading buffer was 25 mM TBAA in 25% Acetonitrile. Separation was performed on a 30% to 70% B in 9 mM and then 80% B in 11 min gradient.

Quantitative analysis of oligonucleotide and internal standard by extracted ion chromatograms of the most abundant ions was performed using MSD ChemStation software.

The internal standard oligonucleotides are described in Table 8. A subscript "s" between two nucleosides indicates a phosphorothioate internucleoside linkage (from the 5' to the 3' end). The absence of a subscript "s" between two nucleosides indicates a phosphodiester internucleoside linkage. A "Po" at the 5'-end indicates a 5'-phosphate group, $(PO(OH)_2-)$. Nucleosides without a subscript are β-D-2'-deoxyribonucleosides. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside. $^{me}C$ indicates a 5-methyl cytosine nucleoside.

TABLE 8

Internal standard oligonucleotides

| ISIS NO | Sequence (5' to 3') | 5'-Chemistry | SEQ ID NO |
|---|---|---|---|
| 355868 | $G_{es}{}^{me}C_{es}G_sT_sT_sT_sG_sC_sT_sC_sT_sC_sT_sT_s{}^{me}C_{es}T_{es}T_{es}G_{es}{}^{me}C_{es}G_{es}T_sT_sT_sT_sT_sT_e$ | OH | 52 |
| 408877 | Po-$U_mU_fG_fU_fC_fU_mC_mU_fG_fG_{ms}U_{ms}C_{fs}C_{fs}U_{fs}U_{fs}A_{fs}C_{ms}U_{ms}U_{ms}T_{es}T_e$ | Phosphate | 53 |
| 409044 | Po-$U_{ms}U_fG_mU_fC_mU_fC_mU_fG_mG_fU_mC_fC_mU_{ms}U_{ms}A_{fs}C_{ms}U_{fs}U_{ms}A_{es}A_e$ | Phosphate | 54 |

Example 13

Modified ssRNAs Targeting PTEN—Multiple Dose In Vivo Study

Six week old BALB/C mice (Jackson Laboratory, Bar Harbor, Me.) were injected subcutaneously twice a day for two days at dosage 25 mg/kg (100 mg total) or twice a day for five days at dosage 30 mg/kg (300 mg total) with the modified single stranded oligomeric compounds targeted to PTEN or with saline control. A 5-10-5 gapped oligomer having 2'-O-MOE modified nucleosides in wings (116847) was also included for comparison.

The modified ssRNAs and the 5-10-5 gapmer are described in Table 9. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH-)$. $^{me}C$ indicates a 5-methyl cytosine nucleoside. Nucleosides followed by a subscript "d" are β-D-2'-deoxyribonucleosides. Nucleosides followed by a subscript "f", "m" or "e" are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside.

The mice were sacrificed 48 hrs following last administration. Liver tissues were homogenized and mRNA levels were quantitated using real-time PCR as described herein for comparison to untreated control levels (% UTC). The results are listed as the average % of PTEN mRNA expression for each treatment group relative to saline-injected control. Additional analysis that were performed in such in vivo studies included plasma chemistries, liver and kidney weights, along with liver, kidney and spleen tissues from animals treated with the modified ssRNAs. Liver transaminase levels, alanine aminotranferase (ALT) and aspartate aminotransferase (AST), in serum were also measured relative to saline injected mice and the results are presented in Table 10.

TABLE 9

Modified ssRNAs targeting PTEN

| ISIS NO. | Sequence (5' to 3') | SEQ ID NO. |
|---|---|---|
| 505739 | Pv-$T_{es}U_{fs}G_mU_{fs}C_mU_{fs}C_mU_{fs}G_{fs}U_mC_{fs}C_mU_{ms}U_{ms}A_{fs}C_{ms}U_{fs}U_{ms}A_{es}A_e$ | 46 |
| 522247 | Pv-$T_{es}U_{fs}A_mU_{fs}C_mU_{fs}A_mU_{fs}A_mA_{fs}U_mG_{fs}A_mU_{fs}C_{ms}A_{fs}G_{ms}G_{fs}U_{ms}A_{es}A_e$ | 47 |
| 522246 | Pv-$T_{es}G_{fs}A_mA_{fs}C_mA_{fs}U_mU_{fs}G_mG_{fs}A_mA_{fs}U_mA_{fs}G_{ms}U_{fs}U_{ms}U_{fs}C_{ms}A_{es}A_e$ | 48 |
| 116847 | $^{me}C_{es}T_{es}G_{es}{}^{me}C_{es}T_{es}A_{ds}G_{ds}{}^{me}C_{ds}{}^{me}C_{ds}T_{ds}{}^{me}C_{ds}T_{ds}G_{ds}G_{ds}A_{ds}T_{es}T_{es}T_{es}G_{es}A_e$ | 49 |

TABLE 10

In vivo multiple dose study with modified ssRNAs targeting PTEN

| ISIS NO. | Dosage (mg/kg total) | UTC (%) | ALT (IU/L) | AST (IU/L) | Chemistry | SEQ ID NO. |
|---|---|---|---|---|---|---|
| saline | 0 | 100 | 22.8 | 53 | — | — |
| 505739 | 300 | 75.4 | 20.8 | 71.5 | 5'-(E)-vinyl phosphonate | 46 |
| 522247 | 300 | 35.8 | 19 | 97 | 5'-(E)-vinyl phosphonate | 47 |
|  | 100 | 63.9 | 21.3 | 102.5 |  |  |
| 522246 | 300 | 44.5 | 32.3 | 98 | 5'-(E)-vinyl phosphonate | 48 |
|  | 100 | 81.2 | 23.3 | 87.3 |  |  |
| 116847 | 100 | 15.3 | 27 | 88.3 | 5-10-5 MOE Gapmer | 49 |

ALT and AST levels and kidney and liver weights were within normal limits for the animals treated with modified single stranded oligomeric compounds relative to saline-treated control. Histopathology report also showed no abnormality from liver, kidney and spleen for the animals treated with the oligomeric compounds.

Example 14

Stability of Modified ssRNAs Targeting PTEN: Multiple Dose In Vivo Study

The modified ssRNAs in Example 13 were evaluated for in vivo stability using the procedures as described in Example 12. Six week old BALB/C mice (Jackson Laboratory, Bar Harbor, Me.) were injected subcutaneously twice a day for two days at dosage 25 mg/kg (100 mg total) or twice a day for five days at dosage 30 mg/kg (300 mg total) with the modified ssRNAs targeted to PTEN shown below. A 5-10-5 gapped oligomer having 2'-O-MOE modified nucleosides in wings (116847) was also included for comparison. The mice were sacrificed 48 hrs following last administration.

Quantitative analysis of the oligonucleotides standard were performed by extracted ion chromatograms in the most abundant charge state (−4) using Chemstation software. The liver concentration (μg/g) of full length modified ssRNAs comprising a 5'-terminal phosphonate group was measured by LC/MS and the results are provided in Table 11.

TABLE 11

In vivo multiple dose stability study with modified ssRNAs targeting PTEN

| ISIS NO. | Dosage (mg/kg total) | Liver conc. of full length ssRNA (μg/g) | Chemistry | SEQ ID NO. |
|---|---|---|---|---|
| 505739 | 300 | 187 | 5'-(E)-vinyl phosphonate | 46 |
| 522247 | 300 | 223 | 5'-(E)-vinyl phosphonate | 47 |
|  | 100 | 145 |  |  |
| 522246 | 300 | 389 | 5'-(E)-vinyl phosphonate | 48 |
|  | 100 | 74 |  |  |
| 116847 | 100 | 190 | 5-10-5 MOE Gapmer | 49 |

Example 15

Modified ssRNAs Targeting PTEN—In Vivo Dose Response Study

Six week old BALB/C mice (Jackson Laboratory, Bar Harbor, Me.) were injected subcutaneously twice a day for one, two, four or six days at dosage 25 mg/kg with the modified single stranded oligomeric compound (522247) targeted to PTEN. A 5-10-5 gapped oligomer having 2'-O-MOE modified nucleosides in wings (116847) was also included for comparison. The mice were sacrificed 48 hrs following last administration. Liver tissues were homogenized and mRNA levels were quantitated using real-time PCR and normalized to RIBOGREEN™ as described herein for comparison to untreated control levels (% UTC). The results are listed as the average % of PTEN mRNA expression for each treatment group relative to saline-injected control. Liver transaminase levels, alanine aminotranferase (ALT), in serum were also measured relative to saline injected mice and the results are presented in Table 12.

TABLE 12

In vivo dose-response study with modified ssRNAs targeting PTEN

| ISIS NO. | Dosage (mg/kg total) | Day (s) | UTC (%) | ALT (IU/L) | Chemistry | SEQ ID NO. |
|---|---|---|---|---|---|---|
| saline | 0 | 0 | 100 | 29.3 | — | — |
| 522247 | 1 | 50 | 64.6 | 30.5 | 5'-(E)-vinyl phosphonate | 47 |
|  | 2 | 100 | 51.1 | 25.8 |  |  |
|  | 4 | 200 | 39.6 | 25.5 |  |  |
|  | 6 | 300 | 36.8 | 30.2 |  |  |
| 116847 | 2 | 100 | 13.82 | 35.5 | 5-10-5 MOE Gapmer | 49 |

ALT levels, liver, kidney, spleen and body weights were within the normal limits in animals treated with the modified single stranded oligomeric compound relative to saline-treated control.

Example 16

Modified ssRNAs Targeting FVII—In Vivo Dose Response and Stability Studies

Six week old BALB/C mice (Jackson Laboratory, Bar Harbor, Me.) were injected subcutaneously with the modified single stranded oligomeric compounds targeted to FVII twice a day for one, two or four days at dosage 25 mg/kg (529100) or 5 mg/kg (457869). The mice were sacrificed 48 hrs following last administration. Liver tissues were homogenized and mRNA levels were quantitated using real-time PCR and normalized to Cyclophilin as described herein for comparison to untreated control levels (% UTC). The results are listed as the average % of PTEN mRNA expression for each treatment group relative to saline-injected control.

The modified ssRNAs are described in Table 13. A subscript "s" between two nucleosides indicates a phosphorothioate internucleoside linkage (going 5' to 3'). The absence of a subscript "s" between two nucleosides indicates a phosphodiester internucleoside linkage. A "Pv" at the 5'-end indicates a 5'-(E)-vinylphosphonate group, $(PO(OH)_2(CH=CH-)$. $^{me}C$ indicates a 5-methyl cytosine nucleoside. Nucleosides followed by a subscript "d" are β-D-2'-deoxyribonucleosides. Nucleosides followed by a subscript f, m or e are sugar modified nucleosides. A subscript "f" indicates a 2'-fluoro modified nucleoside, a subscript "m" indicates a 2'-O-methyl modified nucleoside and a subscript "e" indicates a 2'-O-methoxyethyl (MOE) modified nucleoside.

The modified ssRNAs were also evaluated for in vivo stability using the procedures as described in Example 12. Quantitative analysis of the oligonucleotides standard were performed by extracted ion chromatograms in the most abundant charge state (−4) using Chemstation software. The liver concentration (μg/g) of full length modified ssRNAs comprising a 5'-terminal phosphonate group was measured by LC/MS and the results are provided in Table 14.

TABLE 13

Modified ssRNAs targeting FVII

| ISIS NO. | Sequence (5' to 3') | SEQ ID NO. |
|---|---|---|
| 529100 | Pv-$T_{es}U_{fs}A_mA_{fs}G_mA_{fs}C_mU_{fs}U_mG_{fs}A_mG_{fs}$ $A_mU_{fs}G_{ms}A_{fs}U_{ms}C_{fs}C_{ms}A_{es}A_e$ | 50 |
| 457869 | $G_{es}T_{es}A_{es}{}^{me}C_{es}G_{es}{}^{me}C_{ds}T_{ds}T_{ds}G_{ds}G_{ds}$ $T_{ds}{}^{me}C_{ds}{}^{me}C_{ds}{}^{me}C_{ds}T_{ds}A_{es}{}^{me}C_{es}A_{es}T_{es}G_e$ | 51 |

TABLE 14

In vivo dose-response and stability studies with modified ssRNAs targeting FVII

| ISIS NO. | Dosage (mg/kg total) | UTC (%) | Liver conc. of full length ssRNA (µg/g) | Chemistry | SEQ ID NO. |
|---|---|---|---|---|---|
| Saline | 0 | 100 | — | — | — |
| 529100 | 50 | 96.4 | 61 | 5'-(E)-vinyl phosphonate | 50 |
|  | 100 | 82.9 | 117 |  |  |
|  | 300 | 64.93 | 318 |  |  |
| 457869 | 10 | 59.5 | 39 | 5-10-5 MOE Gapmer | 51 |
|  | 20 | 28 | 88 |  |  |
|  | 40 | 7.0 | 145 |  |  |

The invention claimed is:

1. A compound comprising a single-stranded oligonucleotide consisting of 13 to 30 linked nucleosides and having a nucleobase sequence complementary to a repeat region of an expanded repeat-containing target RNA, wherein the 5'-terminal nucleoside of the single-stranded oligonucleotide comprises a stabilized phosphate moiety and an internucleoside linking group linking the 5'-terminal nucleoside to the remainder of the oligonucleotide; wherein the oligonucleotide comprises a hybridizing region and 0-4 3'-terminal nucleosides, and wherein the hybridizing region has at least one mismatch relative to the repeat region of the expanded repeat-containing target RNA, wherein the 5'-terminal nucleoside of the single-stranded oligonucleotide has Formula I:

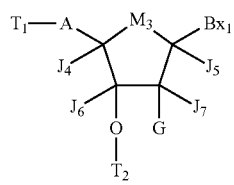

wherein:
$T_1$ is a phosphorus moiety;
$T_2$ is an internucleoside linking group linking the 5'-terminal nucleoside of Formula I to the remainder of the oligonucleotide;
A has a formula selected from among:

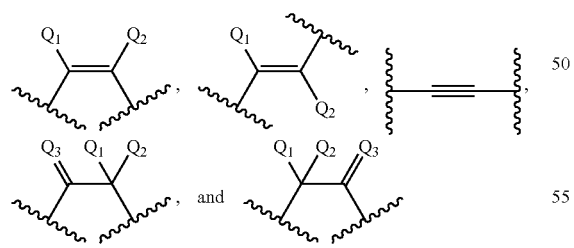

$Q_1$ and $Q_2$ are each independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, substituted $C_2$-$C_6$ alkynyl, and $N(R_3)(R_4)$;
$Q_3$ is selected from among: O, S, $N(R_5)$, and $C(R_6)(R_7)$;
each $R_3$, $R_4$, $R_5$, $R_6$ and $R_7$ is independently selected from among: H, $C_1$-$C_6$ alkyl, substituted $C_1$-$C_6$ alkyl, and $C_1$-$C_6$ alkoxy;

$M_3$ is selected from among: O, S, $NR_{14}$, $C(R_{15})(R_{16})$, $C(R_{15})(R_{16})C(R_{17})(R_{18})$, $C(R_{15})$=$C(R_{17})$, $OC(R_{15})(R_{16})$, and $OC(R_{15})(Bx_2)$;
$R_{14}$ is selected from among: H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;
$R_{15}$, $R_{16}$, $R_{17}$ and $R_{18}$ are each independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;
if $Bx_2$ is present, then $Bx_2$ is a nucleobase and $Bx_1$ is selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;
if $Bx_2$ is not present, then $Bx_1$ is a nucleobase;
either each of $J_4$, $J_5$, $J_6$ and $J_7$ is independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;
or $J_4$ forms a bridge with one of $J_5$ or $J_7$ wherein the bridge comprises from 1 to 3 linked biradical groups selected from O, S, $NR_{19}$, $C(R_{20})(R_{21})$, $C(R_{20})$=$C(R_{21})$, $C[=C(R_{20})(R_{21})]$ and $C(=O)$ and the other two of $J_5$, $J_6$ and $J_7$ are independently selected from among: H, halogen, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl, and substituted $C_2$-$C_6$ alkynyl;
each $R_{19}$, $R_{20}$ and $R_{21}$ is independently selected from among: H, $C_1$-$C_6$ alkyl, substituted $C_1$-$C_6$ alkyl, $C_1$-$C_6$ alkoxy, substituted $C_1$-$C_6$ alkoxy, $C_2$-$C_6$ alkenyl, substituted $C_2$-$C_6$ alkenyl, $C_2$-$C_6$ alkynyl or substituted $C_2$-$C_6$ alkynyl;
G is selected from among: H, OH, halogen, O—[$C(R_8)(R_9)$]$_n$—[$(C=O)_m$—$X_1$]$_j$—Z, and a conjugate group;
each $R_8$ and $R_9$ is independently selected from among: H, halogen, $C_1$-$C_6$ alkyl, and substituted $C_1$-$C_6$ alkyl;
$X_1$ is O, S or $N(E_1)$;
Z is selected from among: H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, substituted $C_2$-$C_6$ alkynyl, and $N(E_2)(E_3)$;
$E_1$, $E_2$ and $E_3$ are each independently selected from among: H, $C_1$-$C_6$ alkyl, and substituted $C_1$-$C_6$ alkyl;
n is from 1 to 6;
m is 0 or 1;
j is 0 or 1;

provided that, if j is 1, then Z is other than halogen or N($E_2$)($E_3$);

each substituted group comprises one or more optionally protected substituent groups independently selected from among: a halogen, $OJ_1$, $N(J_1)(J_2)$, $=NJ_1$, $SJ_1$, $N_3$, CN, $OC(=X_2)J_1$, $OC(=X_2)-N(J_1)(J_2)$, and $C(=X_2)N(J_1)(J_2)$;

$X_2$ is O, S or $NJ_3$; and each $J_1$, $J_2$ and $J_3$ is independently selected from among: H and $C_1$-$C_6$ alkyl.

2. The compound of claim 1, wherein $M_3$ is O.

3. The compound of claim 2, wherein each of $J_4$, $J_5$, $J_6$ and $J_7$ is H.

4. The compound of claim 3, wherein A has the formula:

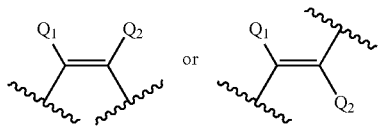

wherein:

$Q_1$ and $Q_2$ are each independently selected from among: H, halogen, $C_1$-$C_6$ alkyl, substituted $C_1$-$C_6$ alkyl, $C_1$-$C_6$ alkoxy, and substituted $C_1$-$C_6$ alkoxy.

5. The compound of claim 4, wherein G is selected from among: a halogen, $OCH_3$, $OCH_2F$, $OCHF_2$, $OCF_3$, $OCH_2CH_3$, $O(CH_2)_2F$, $OCH_2CHF_2$, $OCH_2CF_3$, $OCH_2$—CH=$CH_2$, $O(CH_2)_2$—$OCH_3$, $O(CH_2)_2$—$SCH_3$, $O(CH_2)_2$—$OCF_3$, $O(CH_2)_3$—$N(R_{10})(R_{11})$, $O(CH_2)_2$—$ON(R_{10})(R_{11})$, $O(CH_2)_2$—$O(CH_2)_2$—$N(R_{10})(R_{11})$, $OCH_2C(=O)$—$N(R_{10})(R_{11})$, $OCH_2C(=O)$—$N(R_{12})$—$(CH_2)_2$—$N(R_{10})(R_{11})$, and $O(CH_2)_2$—$N(R_{12})$—$C(=NR_{13})[N(R_{10})(R_{11})]$; wherein $R_{10}$, $R_{11}$, $R_{12}$ and $R_{13}$ are each, independently, H or $C_1$-$C_6$ alkyl.

6. The compound of claim 5, wherein G is selected from among: a halogen, $OCH_3$, $OCF_3$, $OCH_2CH_3$, $OCH_2CF_3$, $OCH_2$—CH=$CH_2$, $O(CH_2)_2$—$OCH_3$, $O(CH_2)_2$—$O(CH_2)_2$—$N(CH_3)_2$, $OCH_2C(=O)$—$N(H)CH_3$, $OCH_2C(=O)$—$N(H)$—$(CH_2)_2$—$N(CH_3)_2$, and $OCH_2$—$N(H)$—$C(=NH)NH_2$.

7. The compound of claim 6, wherein G is selected from among: F, $OCH_3$, and $O(CH_2)_2$—$OCH_3$.

8. The compound of claim 7, wherein the oligonucleotide comprises 1-4 3'-terminal nucleosides.

9. The compound of claim 7, wherein the hybridizing region has one mismatch relative to the repeat region of the expanded repeat-containing target RNA.

10. The compound of claim 7, wherein the hybridizing region has two mismatches relative to the repeat region of the expanded repeat-containing target RNA.

11. The compound of claim 7, wherein the hybridizing region has three mismatches relative to the repeat region of the expanded repeat-containing target RNA.

12. The compound of claim 7, wherein the hybridizing region has four mismatches relative to the repeat region of the expanded repeat-containing target RNA.

13. The compound of claim 11, having a mismatch at the eighth nucleobase from the 5'-end of the hybridizing region.

14. The compound of claim 11, having a mismatch at the ninth nucleobase from the 5'-end of the hybridizing region.

15. The compound of claim 11, having a mismatch at the tenth nucleobase from the 5'-end of the hybridizing region.

16. The compound of claim 7, comprising at least one modified internucleoside linkage.

17. The compound of claim 7, wherein each internucleoside linkage is selected from phosphorothioate and phosphodiester.

18. The compound of claim 7, wherein each of the 6-10 3'-most internucleoside linkages is phosphorothioate linkage.

* * * * *

SEQUENCE LISTING

```
<160> NUMBER OF SEQ ID NOS: 55

<210> SEQ ID NO 1
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 1
tcugcugcag cugcugcuga a                                              21

<210> SEQ ID NO 2
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 2
tcugcugcua cugcugcuga a                                              21

<210> SEQ ID NO 3
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 3
gcugcugcag cugcugcugt t                                              21

<210> SEQ ID NO 4
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 4
```
cagcagcagc ugcagcagct t                                            21

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 5
gcugcugcug cugcugcugt t                                            21

<210> SEQ ID NO 6
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 6
cagcagcagc agcagcagct t                                            21

<210> SEQ ID NO 7
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 7
tcugcugcug cugcugcuga a                                            21

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 8
ttcctggaaa ctgtccctcc                                              20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9
ctcgactaaa gcaggatttc                                              20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

```
<400> SEQUENCE: 10
tctctattgc acattccaag                                              20

<210> SEQ ID NO 11
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 11
ggaguuacuu ucauagcauu u                                            21

<210> SEQ ID NO 12
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 12
augcuaugaa aguaacuccu u                                            21

<210> SEQ ID NO 13
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 13
gcacggaagu ccaucugaau u                                            21

<210> SEQ ID NO 14
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 14
uucagaugga cuuccgugcu u                                            21

<210> SEQ ID NO 15
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 15
gcaggacaaa gauguauuau u                                            21

<210> SEQ ID NO 16
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 16
uaauacaucu uuguccugcu u                                            21

<210> SEQ ID NO 17
<211> LENGTH: 21
```

```
<212> TYPE: RNA
<213> ORGANISM: Artificial Sequence
<220> FEATURE:
<223> OTHER INFORMATION: Synthetic oligonucleotide

<400> SEQUENCE: 17
gggucugugg ugauaaauau u                                              21

<210> SEQ ID NO 18
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 18
uauuuaucac cacagacccu u                                              21

<210> SEQ ID NO 19
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 19
gggucugugg ugauaaauau u                                              21

<210> SEQ ID NO 20
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 20
ugacauuggg uucucauacu u                                              21

<210> SEQ ID NO 21
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 21
gcaucauuau gcaauaugau u                                              21

<210> SEQ ID NO 22
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 22
ucauauugca uaaugaugcu u                                              21

<210> SEQ ID NO 23
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 23
```

```
ggccagaacu aauagcaauu u                                              21

<210> SEQ ID NO 24
<211> LENGTH: 21
<212> TYPE: RNA
<213> ORGANISM: Artificial Sequence
<220> FEATURE:
<223> OTHER INFORMATION: Synthetic oligonucleotide

<400> SEQUENCE: 24
uuuaacgaua aucaagaccg g                                              21

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 25
gcuauaccag cgucgucaut t                                              21

<210> SEQ ID NO 26
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(19)
<223> OTHER INFORMATION: bases at these positions are RNA

<400> SEQUENCE: 26
augacgacgc ugguauagct t                                              21

<210> SEQ ID NO 27
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: bases at these positions are RNA

<400> SEQUENCE: 27
cagacaauga uucacacggu tt                                             22

<210> SEQ ID NO 28
<211> LENGTH: 22
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(20)
<223> OTHER INFORMATION: bases at these positions are RNA

<400> SEQUENCE: 28
accgugugaa ucauugucug tt                                             22
```

```
<210> SEQ ID NO 29
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 29
tcuacugcug cugcugcuga a                                              21

<210> SEQ ID NO 30
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 30
tcugaugcug cugcugcuga a                                              21

<210> SEQ ID NO 31
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 31
tcugcagcug cugcugcuga a                                              21

<210> SEQ ID NO 32
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 32
tcugcuacug cugcugcuga a                                              21

<210> SEQ ID NO 33
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 33
tcugcugaug cugcugcuga a                                              21
```

-continued

<210> SEQ ID NO 34
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 34
tcugcugcua cugcugcuga a                                              21

<210> SEQ ID NO 35
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 35
tcugcugcuu cugcugcuga a                                              21

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 36
tcugcugcug augcugcuga a                                              21

<210> SEQ ID NO 37
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 37
tcugcugcug cagcugcuga a                                              21

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 38
tcugcugcug cuacugcuga a                                              21

<210> SEQ ID NO 39
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 39
tcugcugcug cugcuacuga a                                        21

<210> SEQ ID NO 40
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 40
tcugcugcaa cugcugcuga a                                        21

<210> SEQ ID NO 41
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 41
tcugcugcaa augcugcuga a                                        21

<210> SEQ ID NO 42
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 42
tcugcugaaa augcugcuga a                                        21

<210> SEQ ID NO 43
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 43
tcuacugcua cugcuacuga a                                         21

<210> SEQ ID NO 44
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 44
tcagcuguug cuacuguuga a                                         21

<210> SEQ ID NO 45
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 45
tgcugcugcu gcugcugcua a                                         21

<210> SEQ ID NO 46
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 46
tugucucugg uccuuacuua a                                         21

<210> SEQ ID NO 47
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 47
tuaucuauaa ugaucaggua a                                         21

<210> SEQ ID NO 48
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 48
tgaacauugg aauaguuuca a                              21

<210> SEQ ID NO 49
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 49
ctgctagcct ctggatttga                                20

<210> SEQ ID NO 50
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (2)..(21)
<223> OTHER INFORMATION: bases at these positions are RNA

<400> SEQUENCE: 50
tuaagacuug agaugaucca a                              21

<210> SEQ ID NO 51
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 51
gtacgcttgg tccctacatg                                20

<210> SEQ ID NO 52
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 52
gcgtttgctc ttcttcttgc gtttttt                        27

<210> SEQ ID NO 53
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 53
ttgtctctgg tccttacttt t                              21

<210> SEQ ID NO 54
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 54
ttgtctctgg tccttactta a                              21

```
<210> SEQ ID NO 55
<211> LENGTH: 22
<212> TYPE: RNA
<213> ORGANISM: Artificial Sequence
<220> FEATURE:
<223> OTHER INFORMATION: Synthetic oligonucleotide

<400> SEQUENCE: 55
cgacgacgac gacgacgacg ac                                          22
```